US011633411B2

(12) United States Patent
Ernst et al.

(10) Patent No.: US 11,633,411 B2
(45) Date of Patent: Apr. 25, 2023

(54) METHODS OF TREATING SEPSIS USING ANTI-SEPSIS LIPID A (ASLA) BASED THERAPEUTICS

(71) Applicants: Robert K. Ernst, Silver Spring, MD (US); Erin M. Harberts, Phoenix, MD (US); Alison J. Scott, Silver Spring, MD (US)

(72) Inventors: Robert K. Ernst, Silver Spring, MD (US); Erin M. Harberts, Phoenix, MD (US); Alison J. Scott, Silver Spring, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 16/339,313

(22) PCT Filed: Oct. 4, 2017

(86) PCT No.: PCT/US2017/055186

§ 371 (c)(1),
(2) Date: Apr. 3, 2019

(87) PCT Pub. No.: WO2018/067730

PCT Pub. Date: Apr. 12, 2018

(65) Prior Publication Data

US 2020/0121705 A1 Apr. 23, 2020

Related U.S. Application Data

(60) Provisional application No. 62/403,950, filed on Oct. 4, 2016.

(51) Int. Cl.

| | |
|---|---|
| ***A61K 31/7016*** | (2006.01) |
| ***A61P 31/00*** | (2006.01) |
| ***A61P 29/00*** | (2006.01) |
| ***A61K 9/00*** | (2006.01) |
| ***C07H 13/06*** | (2006.01) |
| ***G01N 33/53*** | (2006.01) |

(52) U.S. Cl.

CPC ........ *A61K 31/7016* (2013.01); *A61K 9/0019* (2013.01); *A61P 29/00* (2018.01); *A61P 31/00* (2018.01); *C07H 13/06* (2013.01); *G01N 33/5308* (2013.01)

(58) Field of Classification Search

CPC ....... A61K 31/7016; A61P 31/00; A61P 29/00
See application file for complete search history.

(56) References Cited

U.S. PATENT DOCUMENTS

| | | | | |
|---|---|---|---|---|
| 4,844,894 | A | 7/1989 | Ribi | |
| 5,612,476 | A | 3/1997 | Christ et al. | |
| 8,722,064 | B2 | 5/2014 | Reed et al. | |
| 10,358,667 | B2 * | 7/2019 | Ernst | A61K 39/099 |
| 2014/0011987 | A1 | 1/2014 | Boons | |
| 2019/0367959 | A1 * | 12/2019 | Ernst | A61K 31/739 |

FOREIGN PATENT DOCUMENTS

| | | | |
|---|---|---|---|
| WO | 2011/080126 | A1 | 7/2011 |
| WO | 2014138696 | A1 | 9/2014 |

OTHER PUBLICATIONS

Renzi et al., Modification of the 1-Phosphate Group during Biosynthesis of Capnocytophaga canimorsus Lipid A, Infection and Immunity, 84:550-561 (2015).
International Search Report from Appl. No.: PCT/US2017/055186, dated Jan. 26, 2018.
Supplementary Partial European Search Report from European U.S. Appl. No. 17/859,134, dated Apr. 15, 2020.
Hawkins et al., Inhibition of Endotoxin Response by Synthetic TLR4 Antagonists, Current Topics in Medicinal Chemistry (2004)4:1147-1171.
Salkowski et al., Pulmonary and Hepatic Gene Expression Following Cecal Ligation and Puncture: Monophosphoryl Lipid A Prophylaxis Attenuates Sepsis-Induced Cytokine and Chemokine Expression and Neutrophil Infiltration, Infection and Immunity, (1998), p. 3569-3578.

* cited by examiner

*Primary Examiner* — Pancham Bakshi
(74) *Attorney, Agent, or Firm* — Nevrivy Patent Law Group P.L.L.C.

(57) ABSTRACT

The present invention provides a method of treating sepsis in a subject, comprising administering to the subject an effective amount of a compound of the formula wherein $R_1$ and $R_2$ may be H, OH, protonated phosphate, a phosphate salt, a sugar phosphonate, or a mono-, di- or poly-saccharide, $R_3$ may be OH or a mono-, di- or poly-saccharide, $R_4$, $R_5$, $R_6$ and $R_7$ may be an alkyl or alkenyl chain of up to 13 carbons (for a chain of 16 carbons), and $R_8$, $R_9$, $R_{10}$ and $R_{11}$ may be H, OH, or an alkyl or alkenyl ester of up to 16 carbons, or a salt thereof.

19 Claims, 43 Drawing Sheets

A *E. coli*

B Eritoran

C ASLA 468

Fig. 12
Fig. 12D
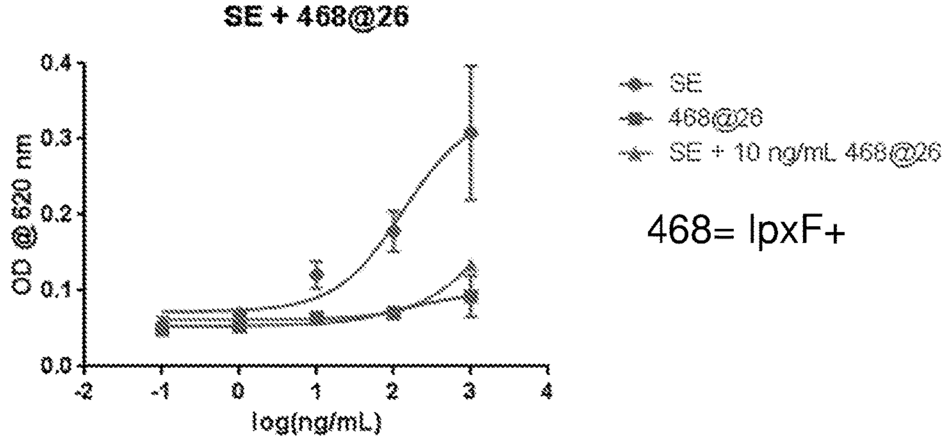
Fig. 12E
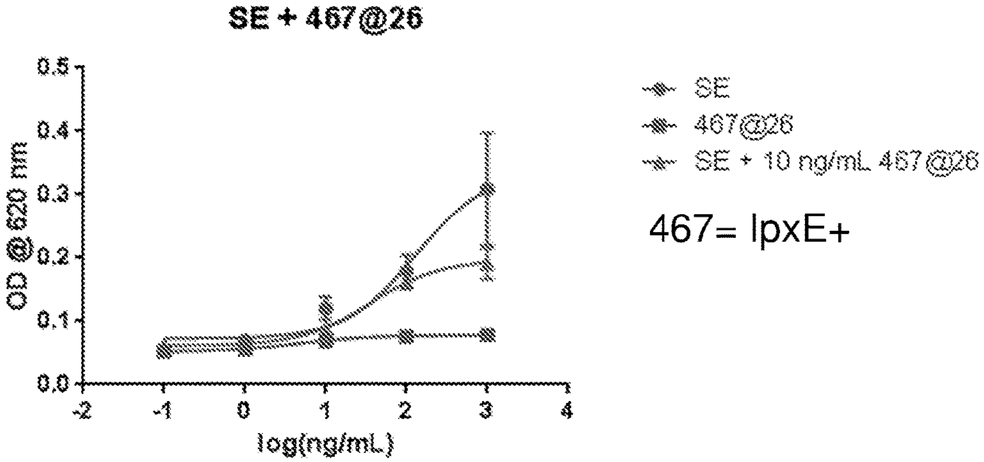
Fig. 12F
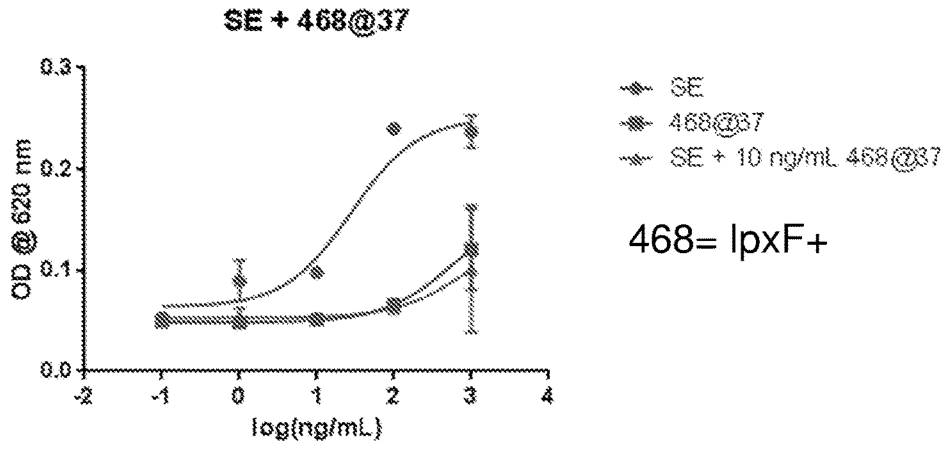

Clinical Scores:

0 – shiny coat, active, responsive to handling

1 – slight lethargy, but still shiny coat

2 – decreased responsiveness to handling, piloerection

3 – decreased activity, ruffled or scruffy coat, hunched posture, rapid shallow breathing 4 – inactive and unresponsive, weak or ataxic 5 - dead

Fig. 15

| Temp | Base Strain | Enzymes ( + or Δ) | Enzyme(s) Function | Stucture/Acylation | *m/z* |
|---|---|---|---|---|---|
| 37°C | *Y. pestis* KIM6- | *ΔpagP* | adds C16 | A (tetra) | 1403.8 |
| 37°C | *Y. pestis* KIM6- | *ΔpagP+* | adds C16 | B (hexa, 2 C16) | 1880.3 |
| 37°C | *Y. pestis* KIM6- | *ΔphoP* | global regulator | A (tetra) | 1403.8 |
| 37°C | *Y. pestis* KIM6- | *ΔphoP pagP+* | global regulator/adds C16 | B (hexa, 2 C16) | 1880.3 |
| 37°C | *Y. pestis* KIM6- | *ΔmsbB* | adds C12 | A (tetra) | 1403.8 |
| 37°C | *Y. pestis* KIM6- | *ΔmsbB pagP+* | adds C12/C16 | B (hexa, 2 C16) | 1880.3 |
| 37°C | *Y. pestis* KIM6- | *ΔlpxP* | adds C16:1 | A (tetra) | 1403.8 |
| 37°C | *Y. pestis* KIM6- | *ΔlpxP pagP+* | adds C16:1/ C16 | B (hexa, 2 C16) | 1880.3 |
| 37°C | *Y. pestis* KIM6- | *ΔmsbB ΔlpxP* | adds C12/ C16:1 | A (tetra) | 1403.8 |
| 37°C | *Y. pestis* KIM6- | *ΔmsbB ΔlpxP pagP+* | adds C12/C16:1 C16 | B (hexa, 2 C16) | 1880.3 |
| 37°C | *Y. pestis* KIM6- | *lpxE+* | removes 1 position Phosphate | H ( tetra, -1P) | 1323.8 |
| 37°C | *Y. pestis* KIM6- | *lpxE+ pagP+* | removes 1 position Phosphate/adds C16 | I ( hexa, C12/C16, -1P) | 1800.3 |
| 37°C | *Y. pestis* KIM6- | *lpxF+* | removes 4' position Phosphate | L ( tetra, -1P) | 1323.8 |
| 37°C | *Y. pestis* KIM6- | *lpxF+ pagP+* | removes 4 'position Phosphate/adds C16 | M ( hexa, C12/C16, -1P) | 1800.3 |

\+ = FUNCTIONAL ENZYME

Δ = LOSS OF ENZYME FUNCTION

STRUCTURE = MAJOR STRUCTURE

ACYLATION = NUMBER OF LIPID A FATTY ACID CHAINS

M/Z = MASS TO CHARGE RATIO

Fig. 16

| Temp | Base Strain | Enzymes ( + or Δ) | Enzyme(s) Function | Stucture/Acylation | *m/z* |
|---|---|---|---|---|---|
| 26°C | *Y. pestis* KIM6- | Δ*pagP* | adds C16 | C (hexa, C12,C16:1) | 1822.2 |
| 26°C | *Y. pestis* KIM6- | Δ*pagP*+ | adds C16 | D (hexa, C12,C16) | 1824.3 |
| | | | | | |
| 26°C | *Y. pestis* KIM6- | Δ*phoP* | global regulator | C (hexa, C12,C16:1) | 1822.2 |
| 26°C | *Y. pestis* KIM6- | Δ*phoP pagP*+ | global regulator/adds C16 | D (hexa, C12,C16) | 1824.3 |
| | | | | | |
| 26°C | *Y. pestis* KIM6- | Δ*msbB* | adds C12 | E (penta, C16:1) | 1640.3 |
| 26°C | *Y. pestis* KIM6- | Δ*msbB pagP*+ | adds C12/C16 | F (hexa, C16:1,C16) | 1878.5 |
| | | | | | |
| 26°C | *Y. pestis* KIM6- | Δ*lpxP* | adds C16:1 | G (penta, C12) | 1586 |
| 26°C | *Y. pestis* KIM6- | Δ*lpxP pagP*+ | adds C16:1/ C16 | D (hexa, C12, C16) | 1824.3 |
| | | | | | |
| 26°C | *Y. pestis* KIM6- | Δ*msbB* Δ*lpxP* | adds C12/ C16:1 | A (tetra) | 1403.8 |
| 26°C | *Y. pestis* KIM6- | Δ*msbB* Δ*lpxP pagP*+ | adds C12/C16:1 C16 | B (hexa 2 C16) | 1880.3 |
| | | | | | |
| 26°C | *Y. pestis* KIM6- | *lpxE*+ | removes 1 position Phosphate | J ( hexa C12,C16:1, -1P) | 1742.3 |
| 26°C | *Y. pestis* KIM6- | *lpxE*+ *pagP*+ | removes 1 position Phosphate/adds C16 | K ( hexa, C12/C16, -1P) | 1744.3 |
| | | | | | |
| 26°C | *Y. pestis* KIM6- | *lpxF*+ | removes 4' position Phosphate | N ( hexa C12,C16:1 -1P) | 1742.3 |
| 26°C | *Y. pestis* KIM6- | *lpxF*+ *pagP*+ | removes 4' position Phosphate/adds C16 | O ( hexa, C12/C16, -1P) | 1744.3 |

+ = FUNCTIONAL ENZYME

Δ = LOSS OF ENZYME FUNCTION

STRUCTURE = MAJOR STRUCTURE

ACYLATION = NUMBER OF LIPID A FATTY ACID CHAINS

M/Z = MASS TO CHARGE RATIO

Fig. 17
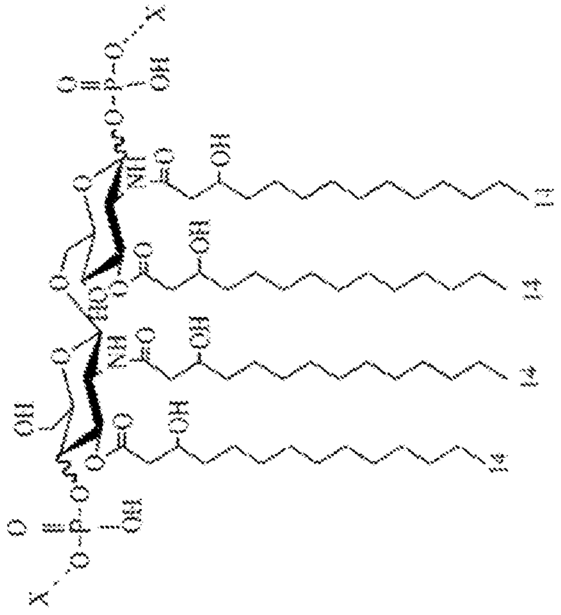
Structure A
**1403.8 *m/z***
del lpxP 37°C
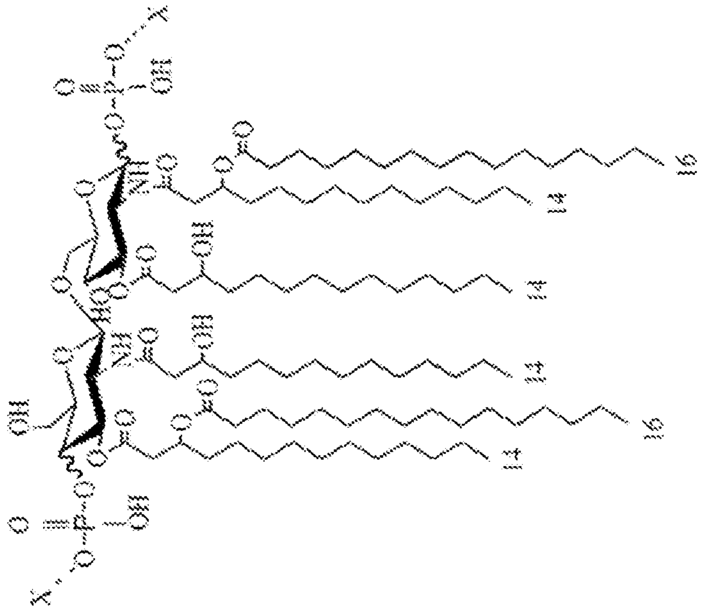
Structure B
**1880.3 *m/z***
del lpxP-pagP+ 37°C del phoP -pagP+ 26°C Chemical Formula: $C_{104}H_{206}N_2O_{25}P_2$
Exact Mass: 1945.44
Molecular Weight: 1946.69
m/z: 1946.44 (100.0%), 1945.44 (85.8%), 1947.45 (57.0%), 1948.45 (26.7%), 1949.45 (9.2%), 1947.44 (5.1%), 1950.46 (1.4%), 1950.45 (1.2%)
Elemental Analysis: C, 64.17; H, 10.67; N, 1.44; O, 20.55; P, 3.18

Structure C1 del phoP -pagP+ 26°C

Chemical Formula: $C_{108}H_{214}N_2O_{25}P_2$
Exact Mass: 2001.50
Molecular Weight: 2002.80
m/z: 2002.50 (100.0%), 2001.50 (85.1%), 2003.51 (65.3%), 2004.51 (29.2%), 2005.51 (9.7%), 2002.51 (2.9%), 2006.52 (2.8%)
Elemental Analysis: C, 64.77; H, 10.77; N, 1.40; O, 19.97; P, 3.09

Structure C2 del phoP -pagP+ 26°C

Structure D1 del phoP -pagP+ 26°C

Chemical Formula: $C_{117}H_{250}N_2O_{25}P_2$
Exact Mass: 2145.78
Molecular Weight: 2147.18
m/z: 2146.79 (100.0%), 2145.78 (76.7%), 2147.79 (68.6%), 2148.79 (31.4%), 2149.80 (8.9%), 2150.80 (3.5%), 2149.79 (3.5%), 2148.80 (1.8%)
Elemental Analysis: C, 65.45; H, 11.74; N, 1.30; O, 18.63; P, 2.89

Structure D2 del phoP -pagP+ 26°C

Chemical Formula: $C_{129}H_{272}N_2O_{25}P_2$
Exact Mass: 2311.95
Molecular Weight: 2313.49
m/z: 2312.96 (100.0%), 2313.96 (75.5%), 2311.95 (69.6%), 2314.97 (33.7%), 2315.97 (15.4%), 2314.96 (5.6%), 2316.97 (5.1%)
Elemental Analysis: C, 66.97; H, 11.85; N, 1.21; O, 17.29; P, 2.68

Structure D3 del phoP -pagP+ 26°C

Chemical Formula: $C_{133}H_{280}N_2O_{25}P_2$
Exact Mass: 2368.02
Molecular Weight: 2369.59
m/z: 2369.02 (100.0%), 2370.02 (73.6%), 2368.02 (67.6%), 2371.03 (40.8%), 2372.03 (16.8%), 2373.03 (5.3%), 2370.03 (4.1%), 2374.04 (1.4%)
Elemental Analysis: C, 67.41; H, 11.91; N, 1.18; O, 16.88; P, 2.61

Structure D4

Fig. 20
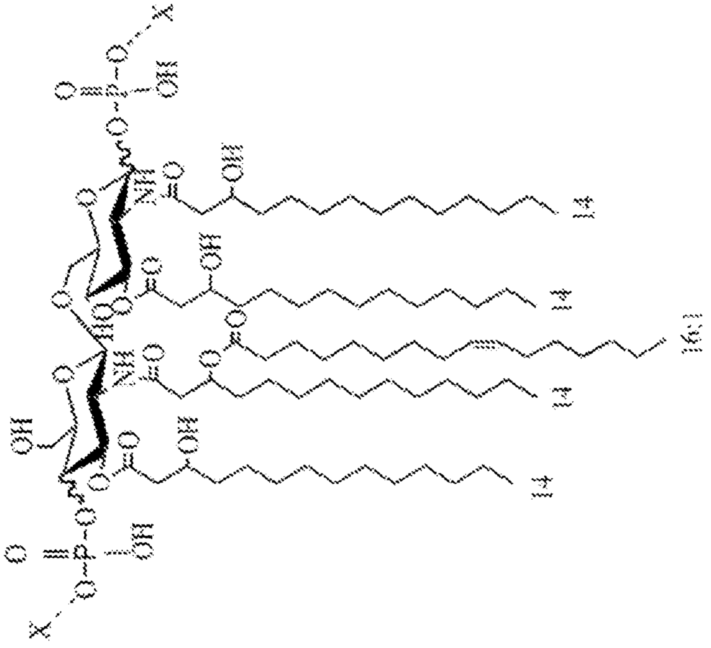
Structure E
**1640.3 *m/z***
del msbB-pagP+ 26°C
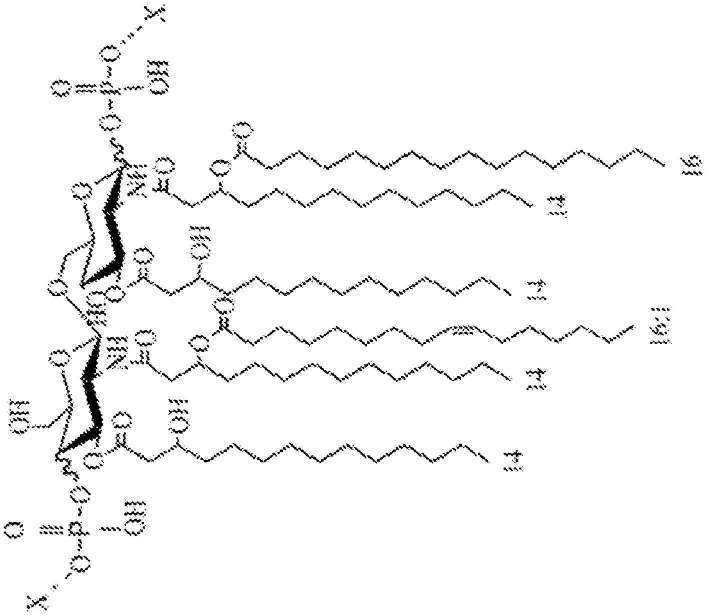
Structure F
**1878.54 *m/z***
del msbB-pagP+ 26°C Fig. 21
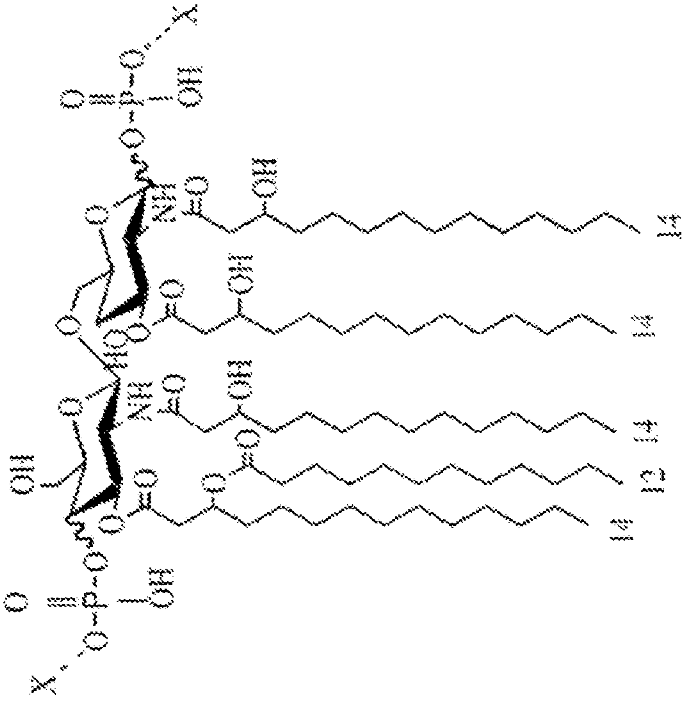
Structure G
1586 *m/z*
del lpxP 37°C
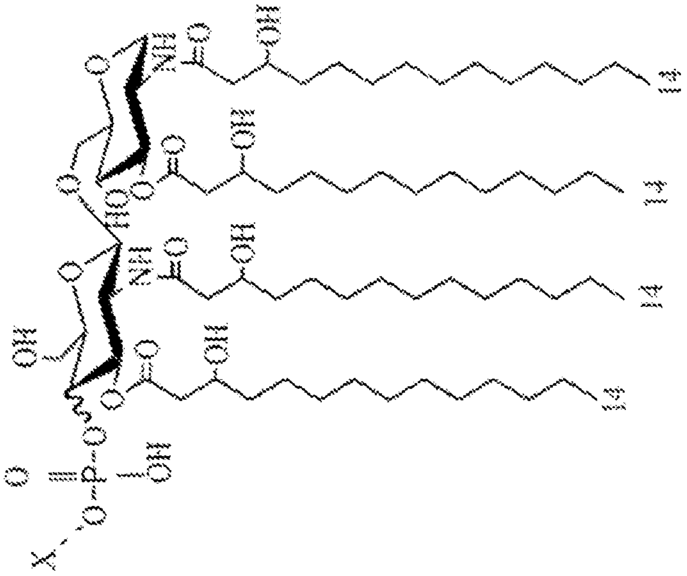
Structure H
1323.8 *m/z*
LpxE KIM637°C Chemical Formula: $C_{105}H_{204}N_2O_{22}P$
Exact Mass: 1876.46
Molecular Weight: 1877.72
m/z: 1877.47 (100.0%), 1876.46 (85.7%), 1878.47 (61.7%), 1879.47 (25.3%), 1880.48 (8.8%), 1881.48 (2.5%), 1879.48 (1.8%)
Elemental Analysis: C, 67.16; H, 10.95; N, 1.49; O, 18.75; P, 1.65

LpxE KIM6-pagP+ 37°C

Structure I

Chemical Formula: $C_{102}H_{198}N_2O_{22}P$
Exact Mass: 1834.42
Molecular Weight: 1835.64
m/z: 1835.42 (100.0%), 1834.42 (88.2%), 1836.42 (58.7%), 1837.43 (20.9%), 1838.43 (8.3%), 1837.42 (4.8%), 1836.43 (2.2%), 1839.43 (2.2%)
Elemental Analysis: C, 66.74; H, 10.87; N, 1.53; O, 19.18; P, 1.69

LpxE KIM6 26°C

Structure J (ASLA 467)

LpxE KIM6 pagP+ 26°C

Chemical Formula: $C_{103}H_{204}N_2O_{22}P$
Exact Mass: 1852.46
Molecular Weight: 1853.70
m/z: 1853.47 (100.0%), 1852.46 (87.3%), 1854.47 (60.7%), 1855.47 (24.5%), 1856.48 (8.4%), 1857.48 (2.3%), 1855.48 (1.7%)
Elemental Analysis: C, 66.74; H, 11.09; N, 1.51; O, 18.99; P, 1.67

Structure K1

LpxE KIM6 pagP+ 26°C

Chemical Formula: $C_{108}H_{214}N_2O_{22}P$
Exact Mass: 1922.54
Molecular Weight: 1923.83
m/z: 1923.55 (100.0%), 1922.54 (83.3%), 1924.55 (63.3%), 1925.55 (26.9%), 1926.56 (6.9%), 1926.55 (2.9%), 1927.56 (2.6%), 1925.56 (1.4%)
Elemental Analysis: C, 67.43; H, 11.21; N, 1.46; O, 18.30; P, 1.61

Structure K2

LpxE KIM6 pagP+ 26°C

Chemical Formula: $C_{120}H_{235}N_2O_{23}P$
Exact Mass: 2103.70
Molecular Weight: 2105.12
m/z: 2104.71 (100.0%), 2103.70 (75.0%), 2105.71 (69.7%), 2106.71 (34.1%), 2107.72 (9.5%), 2108.72 (3.8%), 2107.71 (3.3%)
Elemental Analysis: C, 68.47; H, 11.25; N, 1.33; O, 17.48; P, 1.47

Structure K3

LpxE KIM6 pagP+ 26°C

Chemical Formula: $C_{125}H_{245}N_2O_{23}P$
Exact Mass: 2173.78
Molecular Weight: 2175.26
m/z: 2174.78 (100.0%), 2173.78 (73.1%), 2175.79 (69.9%), 2176.79 (36.7%), 2177.79 (13.6%), 2175.78 (4.2%), 2178.80 (3.0%), 2174.79 (2.1%), 2178.79 (1.6%), 2179.80 (1.1%)
Elemental Analysis: C, 69.02; H, 11.35; N, 1.29; O, 16.92; P, 1.42

Structure K4

LpxF 37°C

Chemical Formula: $C_{68}H_{129}N_2O_{20}P$
Exact Mass: 1324.89
Molecular Weight: 1325.73
m/z: 1324.89 (100.0%), 1325.89 (75.8%), 1326.89 (31.3%), 1327.90 (10.1%), 1328.90 (2.5%), 1326.90 (1.7%)
Elemental Analysis: C, 61.61; H, 9.81; N, 2.11; O, 24.14; P, 2.34

Structure L

LpxF-pagP+ 37°C

Chemical Formula: $C_{101}H_{192}N_2O_{22}P$
Exact Mass: 1816.37
Molecular Weight: 1817.58
m/z: 1817.37 (100.0%), 1816.37 (90.2%), 1818.38 (56.3%), 1819.38 (25.3%), 1820.38 (8.0%), 1818.37 (4.8%), 1817.38 (2.0%), 1821.39 (1.3%), 1821.38 (1.0%)
Elemental Analysis: C, 66.74; H, 10.65; N, 1.54; O, 19.37; P, 1.70

Structure M

LpxF-pagP+ 26°C

Chemical Formula: $C_{98}H_{186}N_2O_{22}P$
Exact Mass: 1774.32
Molecular Weight: 1775.50
m/z: 1775.33 (100.0%), 1774.32 (91.8%), 1776.33 (58.1%), 1777.33 (23.0%), 1778.34 (5.2%), 1778.33 (2.6%), 1779.34 (2.0%), 1777.34 (1.1%)
Elemental Analysis: C, 66.29; H, 10.56; N, 1.58; O, 19.82; P, 1.74

Structure N1

ASLA 468

LpxF-pagP+ 26°C

Chemical Formula: $C_{102}H_{194}N_2O_{22}P$
Exact Mass: 1830.39
Molecular Weight: 1831.61
m/z: 1831.39 (100.0%), 1830.39 (88.2%), 1832.39 (58.7%), 1833.40 (20.9%), 1834.40 (8.2%), 1833.39 (4.9%), 1835.40 (2.2%), 1832.40 (2.2%)
Elemental Analysis: C, 66.89; H, 10.68; N, 1.53; O, 19.22; P, 1.69

Structure N2

ASLA 468 (C16 version)

del phoP -pagP+ 26°C

Chemical Formula: $C_{99}H_{192}N_2O_{22}P$
Exact Mass: 1792.37
Molecular Weight: 1793.56
m/z: 1793.37 (100.0%), 1792.37 (92.0%), 1794.38 (55.2%), 1795.38 (24.5%), 1796.38 (7.7%), 1794.37 (4.9%), 1793.38 (2.0%), 1797.39 (1.2%)
Elemental Analysis: C, 66.30; H, 10.79; N, 1.56; O, 19.63; P, 1.73

Structure O1 del phoP -pagP+ 26°C

Chemical Formula: $C_{103}H_{200}N_2O_{22}P$
Exact Mass: 1848.43
Molecular Weight: 1849.66
m/z: 1849.44 (100.0%), 1848.43 (87.3%), 1850.44 (60.7%), 1851.44 (24.9%), 1852.45 (6.0%), 1852.44 (2.7%), 1853.45 (2.2%), 1851.45 (1.3%)
Elemental Analysis: C, 66.88; H, 10.90; N, 1.51; O, 19.03; P, 1.67

Structure O2 del phoP -pagP+ lpxF 26°C

Chemical Formula: $C_{115}H_{220}N_2O_{23}P$
Exact Mass: 2028.58
Molecular Weight: 2029.95
m/z: 2029.59 (100.0%), 2028.58 (78.3%), 2030.59 (67.1%), 2031.59 (29.7%), 2032.60 (11.2%), 2033.60 (3.3%), 2031.60 (2.1%)
Elemental Analysis: C, 68.04; H, 10.92; N, 1.38; O, 18.13; P, 1.53

Structure O3 del phoP -pagP+ lpxF 26°C

Chemical Formula: $C_{119}H_{228}N_2O_{23}P$
Exact Mass: 2084.65
Molecular Weight: 2086.06
m/z: 2085.65 (100.0%), 2084.65 (75.6%), 2086.65 (67.3%), 2087.66 (28.5%), 2088.66 (12.3%), 2087.65 (5.1%), 2089.66 (3.6%), 2086.66 (2.6%)
Elemental Analysis: C, 68.52; H, 11.02; N, 1.34; O, 17.64; P, 1.48

Structure O4

Fig. 29

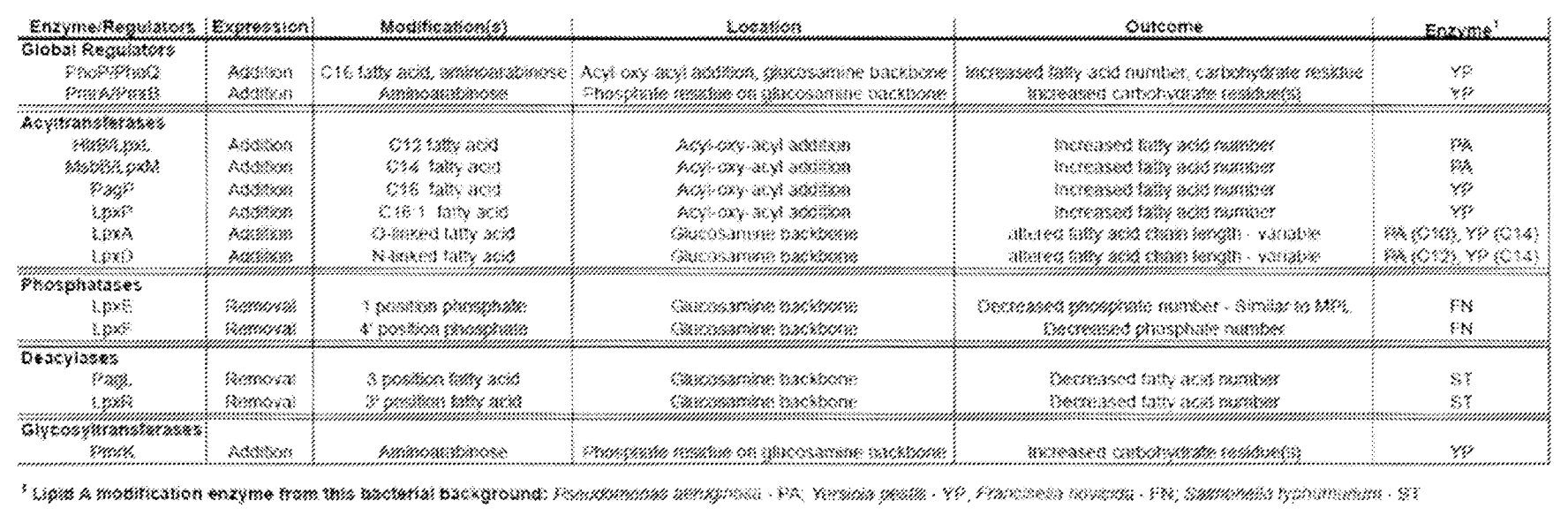

| Enzyme/Regulators | Expression | Modification(s) | Location | Outcome | Enzyme[1] |
|---|---|---|---|---|---|
| **Global Regulators** | | | | | |
| PhoP/PhoQ | Addition | C16 fatty acid, aminoarabinose | Acyl-oxy-acyl addition, glucosamine backbone | Increased fatty acid number, carbohydrate residue | YP |
| PmrA/PmrB | Addition | Aminoarabinose | Phosphate residue on glucosamine backbone | Increased carbohydrate residue(s) | YP |
| **Acyltransferases** | | | | | |
| HtrB/LpxL | Addition | C12 fatty acid | Acyl-oxy-acyl addition | Increased fatty acid number | PA |
| MsbB/LpxM | Addition | C14 fatty acid | Acyl-oxy-acyl addition | Increased fatty acid number | PA |
| PagP | Addition | C16 fatty acid | Acyl-oxy-acyl addition | Increased fatty acid number | YP |
| LpxP | Addition | C16:1 fatty acid | Acyl-oxy-acyl addition | Increased fatty acid number | YP |
| LpxA | Addition | O-linked fatty acid | Glucosamine backbone | altered fatty acid chain length - variable | PA (C10), YP (C14) |
| LpxD | Addition | N-linked fatty acid | Glucosamine backbone | altered fatty acid chain length - variable | PA (C12), YP (C14) |
| **Phosphatases** | | | | | |
| LpxE | Removal | 1 position phosphate | Glucosamine backbone | Decreased phosphate number - Similar to MPL | FN |
| LpxF | Removal | 4' position phosphate | Glucosamine backbone | Decreased phosphate number | FN |
| **Deacylases** | | | | | |
| PagL | Removal | 3 position fatty acid | Glucosamine backbone | Decreased fatty acid number | ST |
| LpxR | Removal | 3' position fatty acid | Glucosamine backbone | Decreased fatty acid number | ST |
| **Glycosyltransferases** | | | | | |
| PmrK | Addition | Aminoarabinose | Phosphate residue on glucosamine backbone | Increased carbohydrate residue(s) | YP |

[1] Lipid A modification enzyme from this bacterial background: *Pseudomonas aeruginosa* - PA; *Yersinia pestis* - YP; *Francisella novicida* - FN; *Salmonella typhimurium* - ST LpxF-pagP+ 26°C

ASLA 470

METHODS OF TREATING SEPSIS USING ANTI-SEPSIS LIPID A (ASLA) BASED THERAPEUTICS

CROSS-REFERENCE TO RELATED APPLICATIONS

This application claims the benefit of U.S. Provisional Appl. No. 62/403,950, filed Oct. 4, 2016, the contents of which are hereby incorporated by reference in their entirety.

STATEMENT OF FEDERALLY SPONSORED RESEARCH AND DEVELOPMENT

This invention was made with government support under Grant Number AI123820 awarded by the National Institutes of Health. The government has certain rights in the invention.

FIELD OF THE INVENTION

The invention relates to infectious disease, in particular to methods of treating and preventing sepsis.

BACKGROUND OF THE INVENTION

Sepsis, the condition of having a systemic blood-borne bacterial infection, annually affects over a million people in the United States with a risk of death from sepsis being as high as 30%, severe sepsis as high as 50%, and septic shock as high as 80%. *Sepsis Fact Sheet*. (http://www.nigms.nih.gov/Education/Pages/factsheet/factsheet_sepsis.aspx) NIGMS. Accessed 2016. Treatment for sepsis is listed as the most expensive condition treated in U.S. hospitals, costing more than $20 billion in 2011. Torio et al., Healthcare Cost and Utilization Project (HCUP) *Statistical Brief*, #160, 2013, 1-12. With more than 258,000 lives being lost yearly, sepsis ranks as the third leading cause of death in the U.S. after heart disease and cancer. Subsequently, survivors often face long-term effects post-sepsis, including amputations, anxiety, memory loss, chronic pain and fatigue, and worsened cognitive function.

Sepsis results from the overproduction of inflammatory mediators as a consequence of the interaction of the immune system with bacteria and bacterial wall constituents. Lipopolysaccharide (LPS), also known as endotoxin and the major outer membrane component of Gram-negative bacteria is one of the causative agents known to trigger an adverse immune response.

Dissemination of bacteria in the blood results in a cytokine storm, which converts a healthy immune system, which normally functions to control blood-borne infections into a liability for the patient.

Sepsis caused by Gram-negative bacteria is, in part, dependent on stimulation of Toll-like receptor 4 (TLR4) by the bacterial membrane component lipopolysaccharide (LPS). The minimal component of LPS necessary for TLR4 stimulation is lipid A, the membrane anchor component of LPS. Disease causing pro-inflammatory forms of LPS bind to toll-like receptor 4 (TLR4) on host cell membranes and initiate a cascade of inflammatory signaling throughout the body that leads to a wide range of symptoms eventually including hemorrhage of vital organs and, if not controlled effectively, death. Cohen, J. *Nature* 2002, 420, 885-891. Due to the multifaceted nature of symptoms observed, it has proven difficult to treat septic patients. Synthetically manufactured treatments have had some success in ameliorating short-term symptoms of acute sepsis, however they were not successful at decreasing the mortality rate of septic patients. Hotchkiss et al., *Nat. Rev. Immunol.* 2006, 6, 813-822. This ineffectiveness has been attributed, in part, to the inability of synthetically created molecules to mimic naturally occurring disease causing LPS interactions within the host.

The inflammatory potential associated with systemic LPS exposure is dependent on the structure of the molecule and its ability to tightly bind the MD2/TLR4 complex. The innate immune system is the first line of defense in mammals against microbial infections and involves inflammatory cascades mediated by the pathogen recognition receptor (PRR), TLR4. Medzhitov, R. *Nat. Rev. Immunol.* 2001, 1, 135-145. The Gram-negative bacterial outer membrane glycolipid component LPS consists of three distinct regions: hydrophilic O-antigen, core linking sugars, and heavily acylated lipid A. Raetz et al., *Annu. Rev. Biochem.* 2002, 71, 635-700. The structure of LPS is variable and can be altered by LPS biosynthetic enzymes that specifically add, trim, or remove side chains from the lipid A portion of LPS. Raetz et al., *J. Lipid Res.* 2009, 50 Suppl, S103-108; Needham et al., *Nature Reviews Microbiology* 2013, 11, 467-481. Lipid A structure is a determinant of TLR4 recognition and activation. Ernst et al., *Science* 1999, 286, 1561-1565; Miller et al., *Nature Reviews Microbiology* 2005, 3, 36-46; Siegemund et al., *Nat Immunol* 2012, 13, 1031-1033; Rietschel et al., *FASEB J.* 1994, 8, 217-225. LPS-binding protein (LBP) and CD-14 cooperate to transfer bacterial lipid A (pro-inflammatory structure) to the serum protein MD-2, which then loads into the TLR4 loop resulting in MD2/TLR4 assembly and dimerization, and subsequently intracellular signaling. Akashi et al., *J. Exp. Med.* 2003, 198, 1035-1042; Shimazu, R.; Akashi et al., *The Journal of Exp. Medicine* 1999, 86, 973-983. MD2/TLR4-LPS complex recruits downstream mediators of inflammation, signaling through a MyD88-mediated pathway converging on the canonical pro-inflammatory transcription factor, NF-kB. The MD2/TLR4 complex has higher affinity for LPS than MD2 alone, suggesting cooperative LPS binding. Moreover, MD2/TLR4 heterodimer also has complex ligand specificity, therefore even subtle variations in lipid A scaffold can abolish the endotoxic response. Balk et al., *Molecular Immunology* 2015, 63, 134-142; Oblak, A.; Jerala, R. *PLoS ONE* 2014, 9, e107520. The total number of acyl chains (fatty acids) attached to the diglucosamine lipid A backbone is one of the major factors that determines strength of immune response in humans. Ohio et al., *Proc. Natl. Acad. Sci. U.S.A* 2012, 109, 7421-7426; Ohto et al., *Science* 2007, 316, 1632-1634. For example, hexa-acetylated lipid as found in *E. coli* (Ec) and *S. enterica* (Se) elicit a strong pro-inflammatory response, whereas penta-acylated lipid A is 100-fold less potent *R. sphaeroides* (Rs) lipid A with tetra-acylated lipid A structures (like Eritoran) acts as TLR4 antagonists. Lohmann et al., *J. Endotoxin Res.* 2003, 9, 33-37; Lohmann et al., *J. Endotoxin Res.* 2007, 13, 235-242. Endotoxic activity is also dramatically reduced (~100 fold) if either of the two terminal phosphate groups are removed, as observed with the adjuvant molecule monophosphoryl lipid A (MPL).

Structurally, the MD2/TLR4-LPS complex adopts symmetric monomeric or dimeric structures, without perturbing the overall assembly of TLR4 and MD2. Kim et al., *Cell* 2007, 130, 906-917; Park, B. S.; Song et al., *Nature* 2009, 458, 1191-1195. TLR4 has characteristic horseshoe-like shape, whereas MD2 has a large cup-like hydrophobic pocket for lipid-A binding composed of two antiparallel-β sheets connected by loops. Ohto et al., *Science* 2007, 316, 1632-1634. Phenyalanine-126 present in βG and βH strands of MD2 dynamically switches between activator and inhibitor modes by protruding into or away from the solvent area. Ohto et al., *Proc. Natl. Acad. Sci. U.S.A* 2012, 109, 7421-7426; Ohto et al., *Science* 2007, 316, 1632-1634; Kim et al., *Cell* 2007, 130, 906-917; Park et al., *Nature* 2009, 458, 1191-1195. Crystal structures of MD2 bound to Ec LPS shows interactions within the large hydrophobic pocket where five of the six lipid chains of LPS are buried deep inside the pocket and the remaining chain is exposed to the surface of MD2. This interaction displaces the phosphorylated glucosamine backbone by ~5 Å towards the solvent area, thereby facilitating the MD2/TRL4-LPS dimerization. Ohto et al., *Science* 2007, 316, 1632-1634; Kim et al., *Cell* 2007, 130, 906-917; Park et al., *Nature* 2009, 458, 1191-1195. In contrast, the tetra-acylated antagonist Eritoran sits completely within the hydrophobic pocket of MD2 but is rotated by 180° in comparison to Ec LPS resulting in an antagonistic response. *Sepsis Fact Sheet.* (http://www.nigms.nih.gov/Education/Pages/factsheet/factsheet_sepsis.aspx) NIGMS. Accessed 2016; Park et al., *Nature* 2009, 458, 1191-1195. Eritoran (or E5564) is a synthetic molecule derived from the lipid A structure of the nonpathogenic LPS of Rs. Despite many excellent structural studies in recent years, the SAR of lipid A and MD2/TLR4 complex binding and discrimination is far from clear. In the case of sepsis, overproduction of pro-inflammatory cytokines can result in fatal tissue hemorrhage and organ failure. Therefore, even modest advances in treating sepsis will lead to improvements in patient outcomes and reduce the cost burden on the healthcare system.

There is a significant need to develop new therapeutics and methods to treat and prevent sepsis in patients.

This background information is provided for informational purposes only. No admission is necessarily intended, nor should it be construed, that any of the preceding information constitutes prior art against the present invention.

SUMMARY

It is to be understood that both the foregoing general description of the embodiments and the following detailed description are exemplary, and thus do not restrict the scope of the embodiments.

The present invention is directed to anti-sepsis lipid A (ASLA) based therapeutic compounds, therapeutic compositions and methods of using the same. In some embodiments, the therapeutic compositions are useful to treat and prevent sepsis in a subject.

In one aspect, the invention provides a compound of the formula:

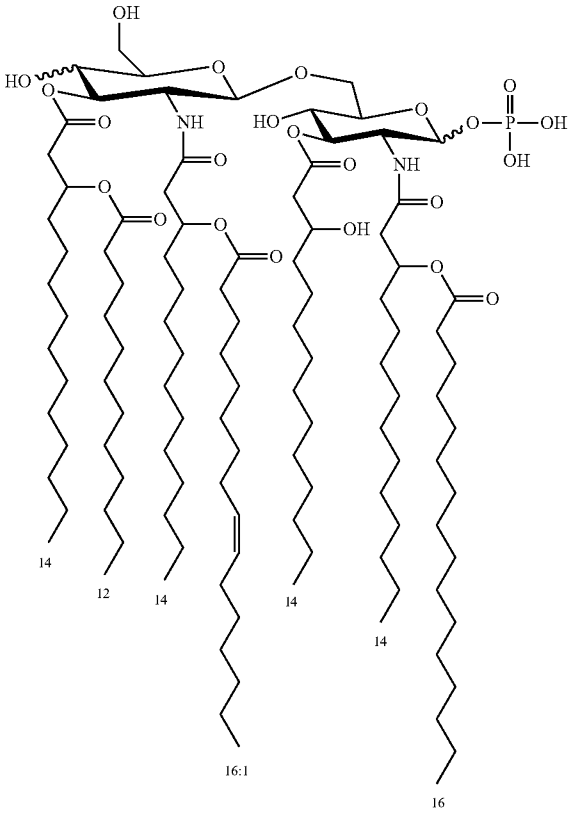

In another aspect, the invention provides a compound of the formula:

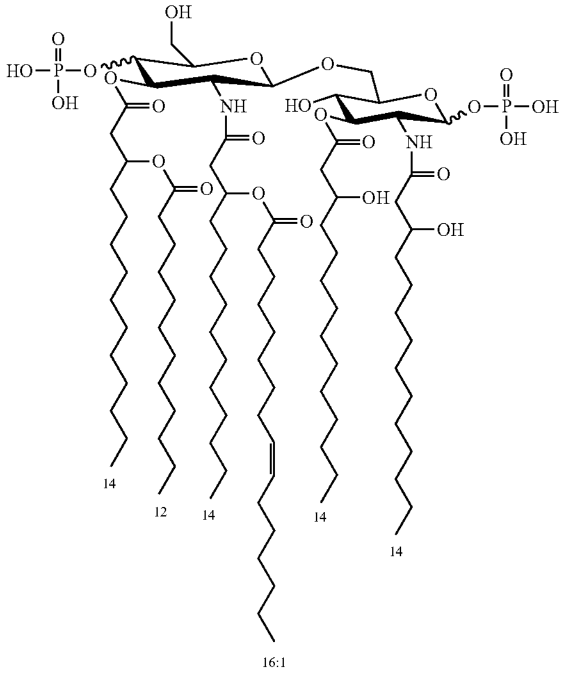

In another aspect, the invention provides a compound of the formula:
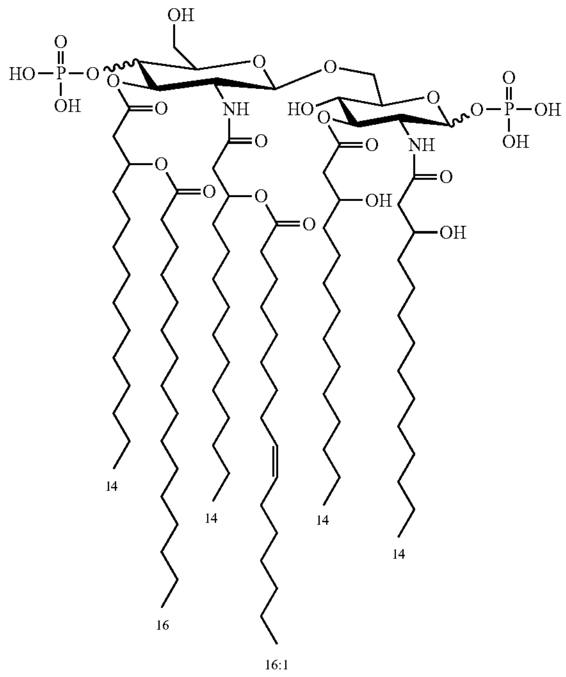
In another aspect, the invention provides a compound of the formula:
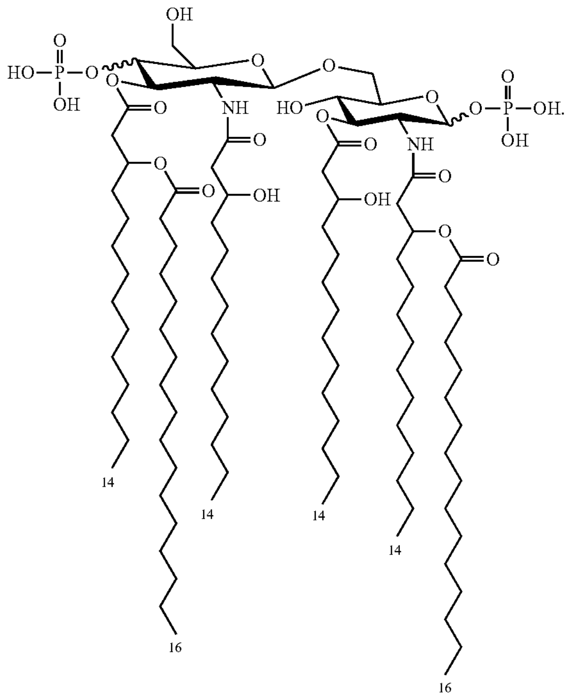
In another aspect, the invention provides a compound of the formula:
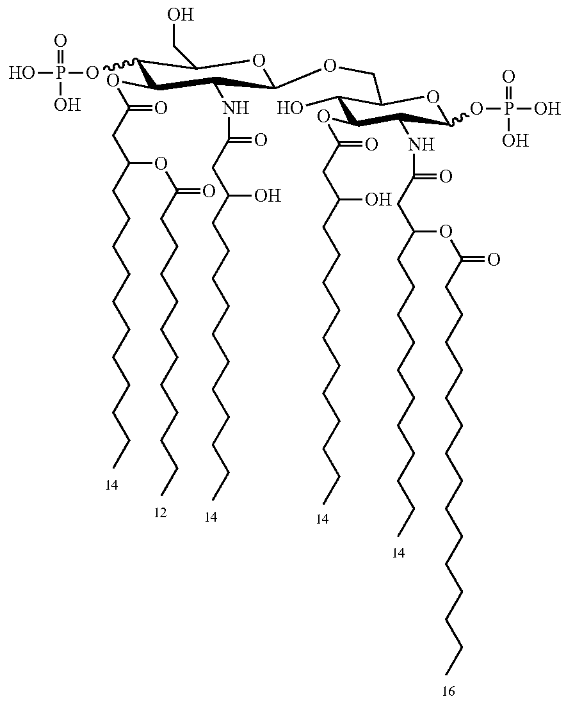
In another aspect, the invention provides a compound of the formula:
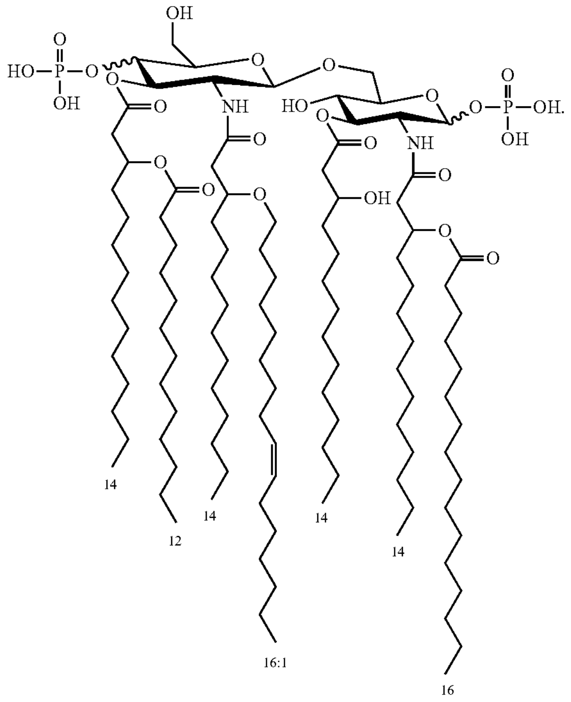

In another aspect, the invention provides a compound of the formula:
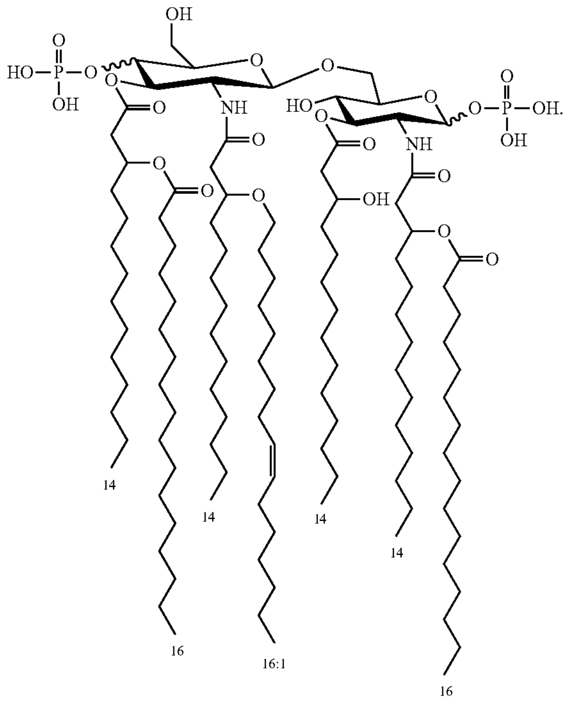
In another aspect, the invention provides a compound of the formula:
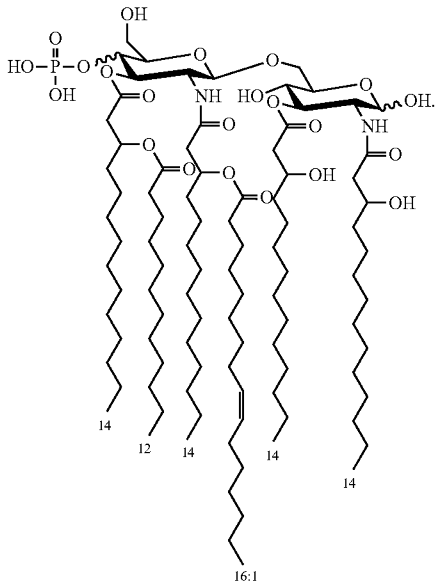
In another aspect, the invention provides a compound of the formula:
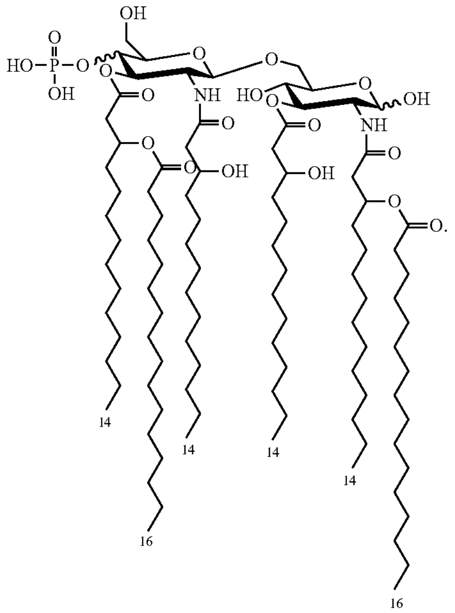
In another aspect, the invention provides a compound of the formula:
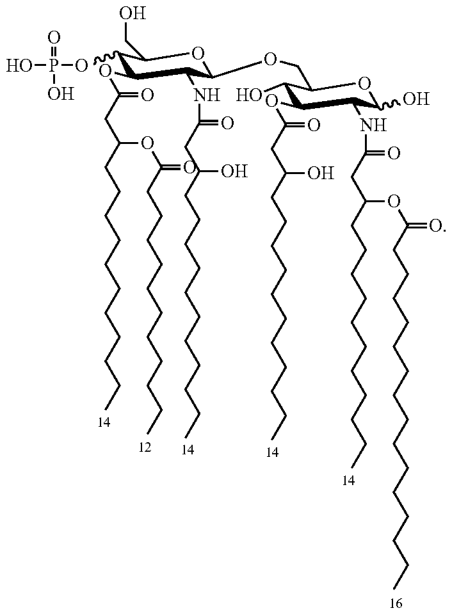

In another aspect, the invention provides a compound of the formula:
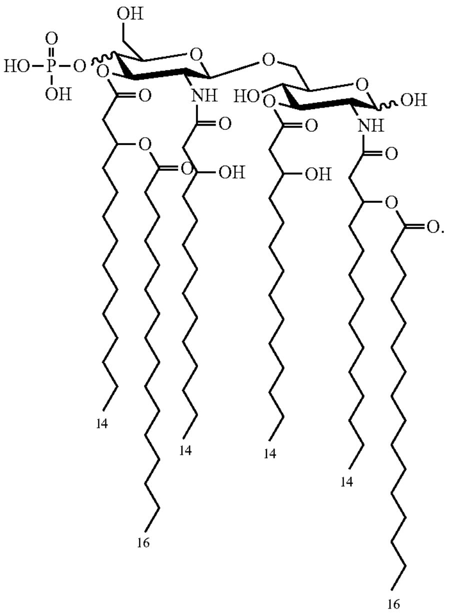
In another aspect, the invention provides a compound of the formula:
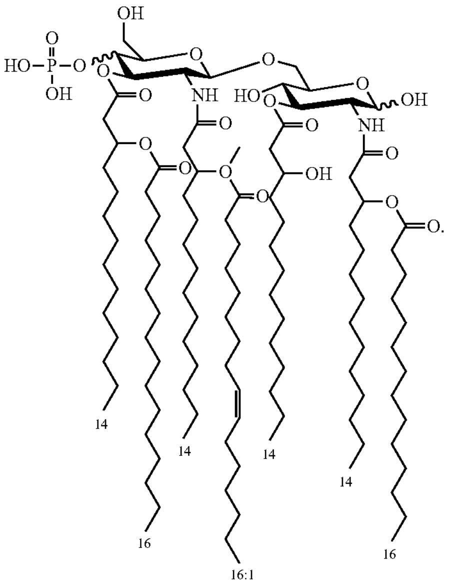
In another aspect, the invention provides a compound of the formula:
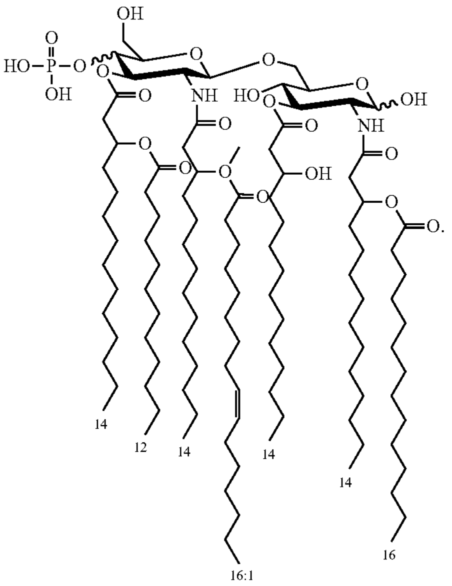
In another aspect, the invention provides a compound of the formula:
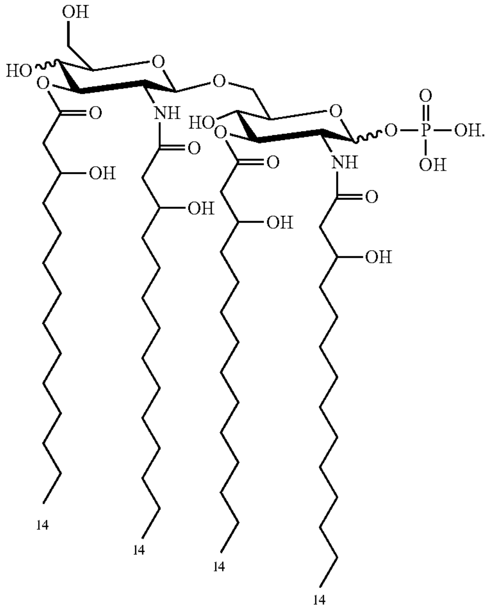

In another aspect, the invention provides a compound of the formula:
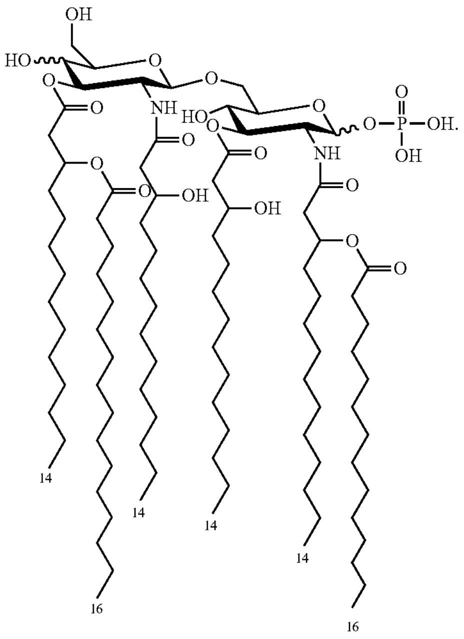
In another aspect, the invention provides a compound of the formula:
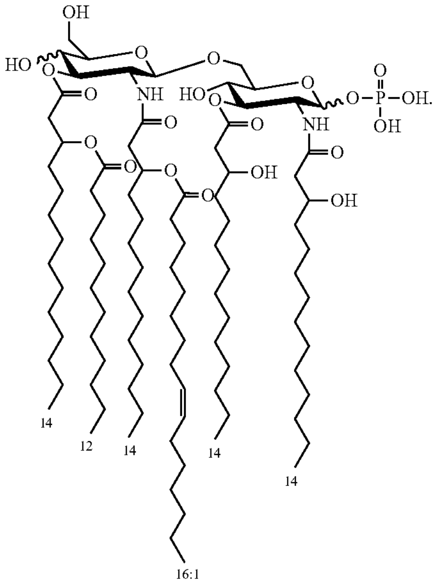
In another aspect, the invention provides a compound of the formula:
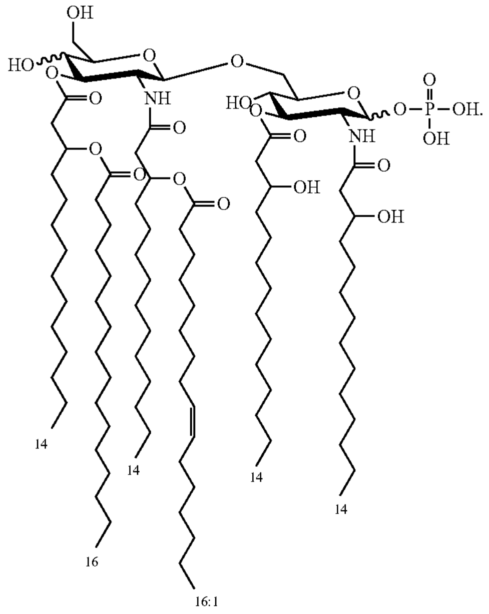
In another aspect, the invention provides a compound of the formula:
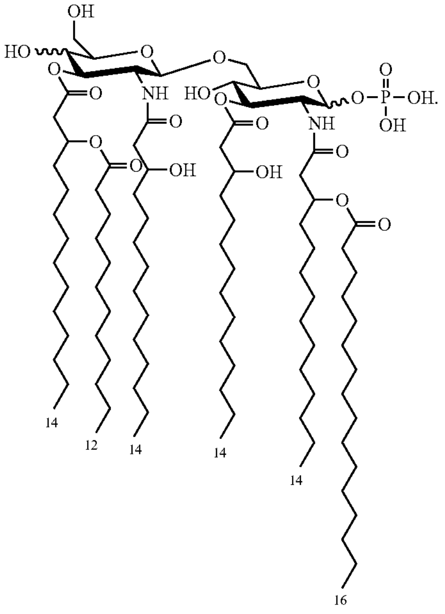

In another aspect, the invention provides a compound of the formula:

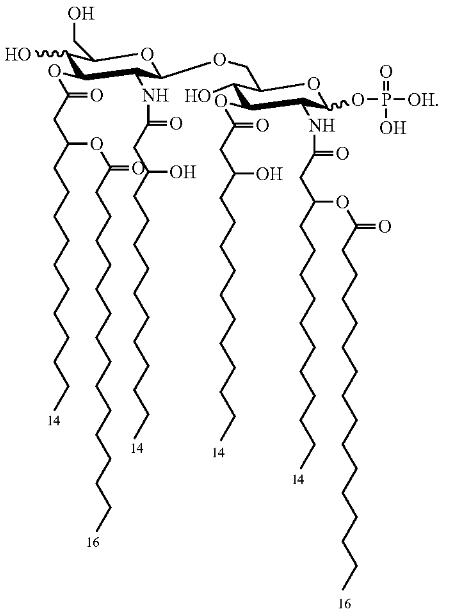

In another aspect, the invention provides a compound of the formula:

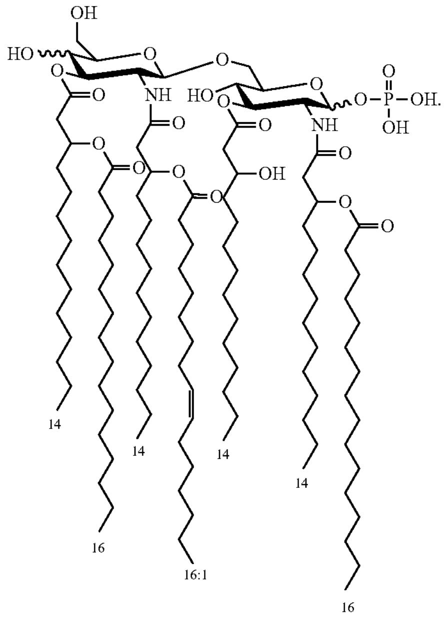

In another aspect, the invention provides a compound of the formula:

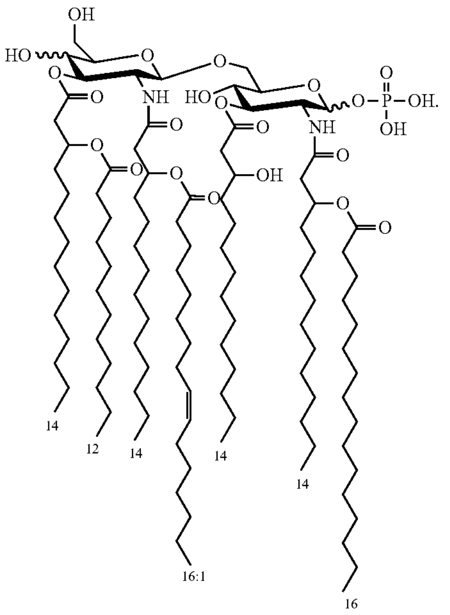

In another aspect, the invention comprises a pharmaceutical composition of any of the compounds or combination thereof in combination with a pharmaceutically acceptable carrier.

In another aspect, the invention provides a method of treating or preventing sepsis in a subject, comprising administering to the subject an effective amount of an anti-sepsis lipid A (ASLA) based therapeutic compound of the formula

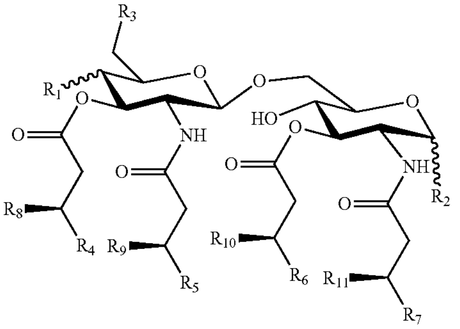

wherein $R_1$ and $R_2$ may be H, OH, protonated phosphate, a phosphate salt, a sugar phosphonate, or a mono-, di- or poly-saccharide, $R_3$ may be OH or a mono-, di- or poly-saccharide, $R_4$, $R_5$, $R_6$ and $R_7$ may be an alkyl or alkenyl chain of up to 13 carbons (for a chain of 16 carbons), and $R_8$, $R_9$, $R_{10}$ and $R_{11}$ may be H, OH, or an alkyl or alkenyl ester of up to 16 carbons, or a salt thereof.

In another embodiment, the invention provides a method of screening a molecule for anti-sepsis activity, comprising i) genetically engineering a Gram-negative microorganism to produce a lipid A mimetic;

ii) isolating the lipid A mimetic from the microorganism; and iii) assaying the lipid A mimetic for anti-sepsis activity.

In some embodiments, the lipid A mimetic has the following formula

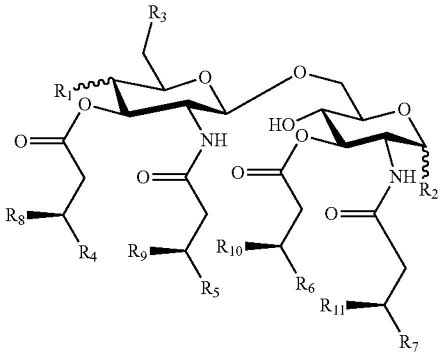

wherein $R_1$ and $R_2$ may be H, OH, protonated phosphate, a phosphate salt, a sugar phosphonate, or a mono-, di- or poly-saccharide, $R_3$ may be OH or a mono-, di- or poly-saccharide, $R_4$, $R_5$, $R_6$ and $R_7$ may be an alkyl or alkenyl chain of up to 13 carbons (for a chain of 16 carbons), and $R_8$, $R_9$, $R_{10}$ and $R_{11}$ may be H, OH, or an alkyl or alkenyl ester of up to 16 carbons.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

FIG. 15 provides a description of individual strains generated, structure of the resultant lipid A, and mass at 37° C.

FIG. 16 provides description of individual strains generated, structure of the resultant lipid A, and mass when the *Y. pestis* strain was grown at 26° C.

FIG. 17 demonstrates the structure of exemplary LPS molecules generated by methods of the disclosure using an engineered *Y. pestis*.

FIG. 20 demonstrates the structure of exemplary LPS molecules generated by methods of the disclosure using an engineered *Y. pestis*.

FIG. 21 demonstrates the structure of exemplary LPS molecules generated by methods of the disclosure using an engineered *Y. pestis*.

FIG. 29 provides a description and heterologous sources of LOS/Lipid A modifying enzymes for BECC, illustrating examples of modifying enzymes that may be used to generate *Y. pestis* or other strains with modified LOS.

DETAILED DESCRIPTION OF THE INVENTION

Figure 1:
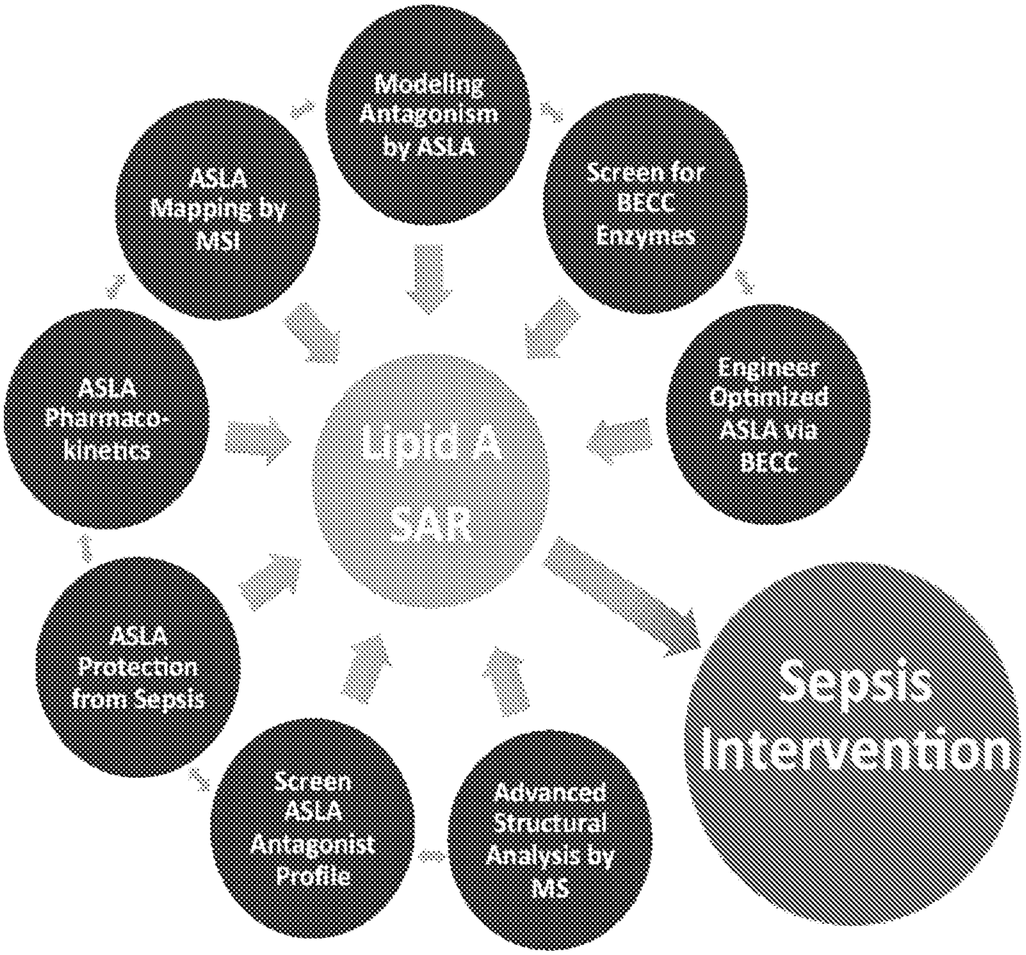
FIG. 1. Multi-faceted approach to lipid A structure activity relationship (SAR). Innovation, rational design, and complementary approaches will result in unprecedented definition of the lipid A:TLR4 SAR, resulting in novel molecules for sepsis intervention. ASLA—anti-septic lipid A.

The present invention is based on the discovery of lipid A based therapeutics that are useful to treat and prevent sepsis in subjects. To inhibit TLR4 signaling at the 'trigger' event, anti-sepsis lipid A (ASLA) based therapeutic(s) were developed using a lipid A:TLR4 structure-activity relationship (SAR) as a guide. As provided herein, the invention relates to methods of treating or preventing sepsis using the molecules that compete with pro-inflammatory lipid A resulting in protection from lethal sepsis, both prophylactically and therapeutically. Without being bound by theory, the anti-sepsis lipid A (ASLA) based therapeutic interferes with TLR4:lipid A binding events.

Reference will now be made in detail to the presently preferred embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

In some embodiments, the practice of the present invention employs various techniques of molecular biology (including recombinant techniques), microbiology, cell biology, biochemistry and immunology. See, e.g., Sambrook et al. *Molecular Cloning: A Laboratory Manual, 2$^{nd}$* edition (1989); *Current Protocols in Molecular Biology* (F. M. Ausubel et al. eds. (1987)); the series *Methods in Enzymology* (Academic Press, Inc.); *PCR: A Practical Approach* (M. MacPherson et al. IRL Press at Oxford University Press (1991)); *PCR* 2: *A Practical Approach* (M. J. MacPherson, B. D. Hames and G. R. Taylor eds. (1995)); *Antibodies, A Laboratory Manual* (Harlow and Lane eds. (1988)); *Using Antibodies, A Laboratory Manual* (Harlow and Lane eds. (1999)); and *Animal Cell Culture* (R. I. Freshney ed. (1987)).

Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341).

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. As used in the specification and claims, the singular form "a," "an" and "the" include plural references unless the context clearly dictates otherwise. For example, the term "an antibody" includes a plurality of antibodies, including mixtures thereof. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" means plus or minus 10% of the numerical value of the number with which it is being used.

The term "anti-sepsis lipid A (ASLA) based therapeutic" as used herein refers to a compound that acts on Toll-like receptor 4 (TLR4) complex and is useful to treat and/or prevent sepsis in a subject, either alone or in combination with other therapies.

Embodiments of the disclosure include anti-sepsis lipid A (ASLA) based therapeutics and methods of making and using the same. In some embodiments, the anti-sepsis lipid A (ASLA) based therapeutics are produced by bacteria, including genetically engineered bacteria. In some embodiments, the compositions comprise one or more anti-sepsis lipid A (ASLA) based therapeutics, and they may be used alone as an anti-sepsis composition or with another compound/composition to elicit a desired anti-sepsis response in a subject. Embodiments include methods of generating the molecules/compositions, and methods of using the compositions for administering to a subject for treating or preventing sepsis, as well as methods of screening for anti-sepsis compounds.

In one embodiment, the invention provides a compound of the formula:

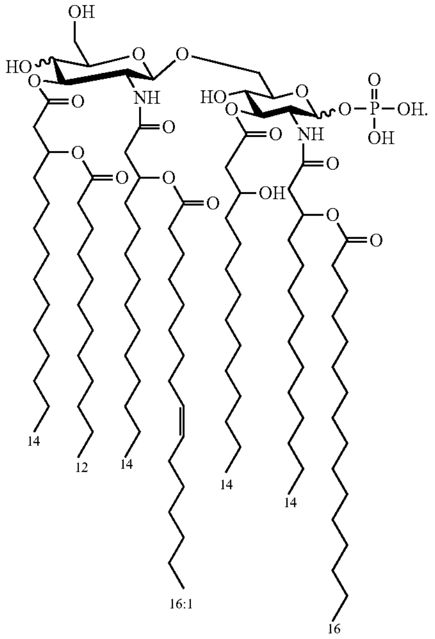

In another embodiment, the invention provides a compound of the formula:

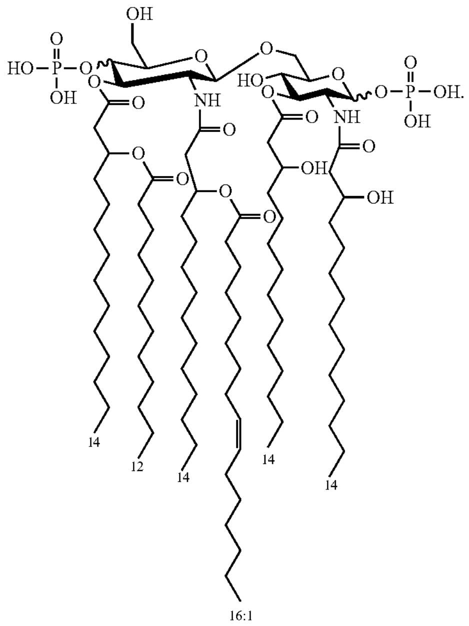

In another embodiment, the invention provides a compound of the formula:

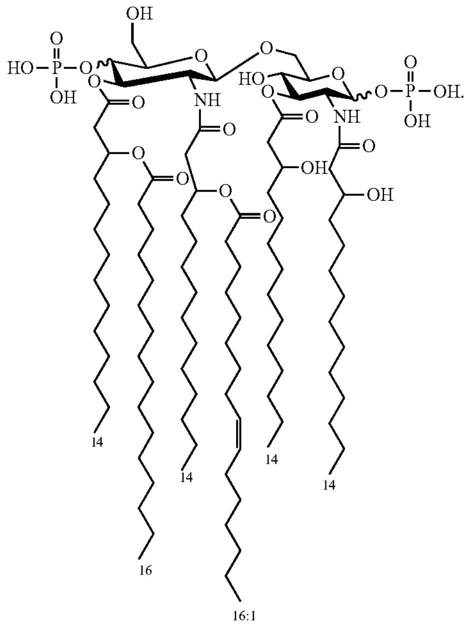

In another embodiment, the invention provides a compound of the formula:
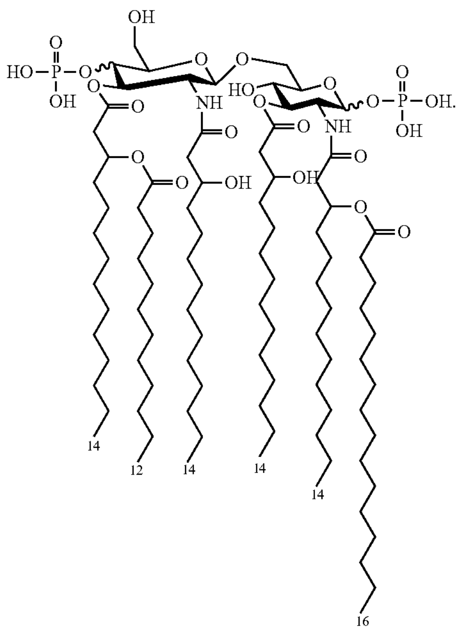
In another embodiment, the invention provides a compound of the formula:
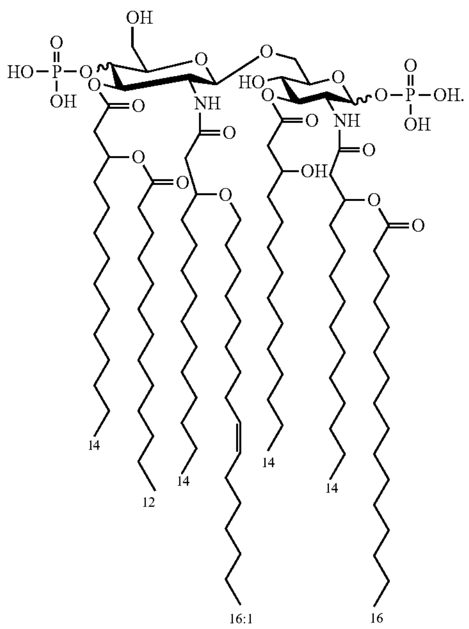
In another embodiment, the invention provides a compound of the formula:
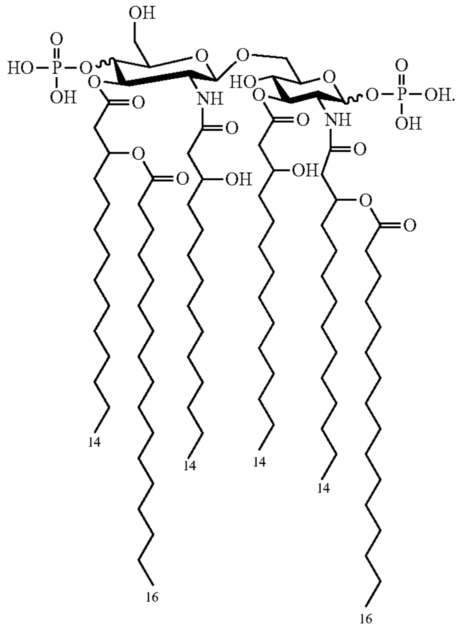
In another embodiment, the invention provides a compound of the formula:
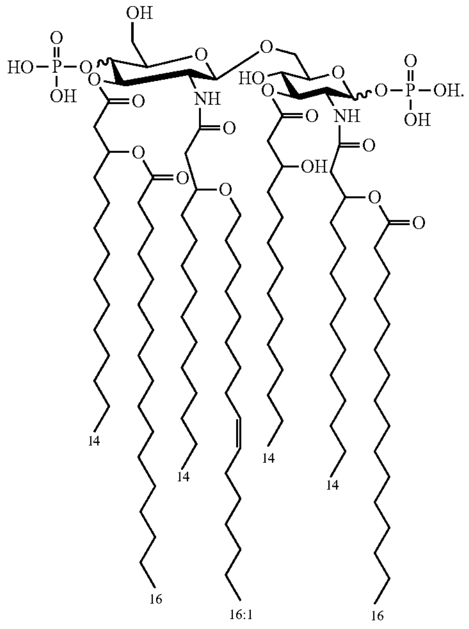

In another embodiment, the invention provides a compound of the formula:
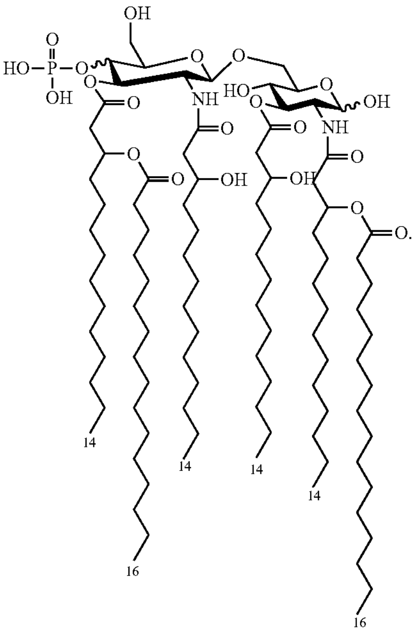
In another embodiment, the invention provides a compound of the formula:
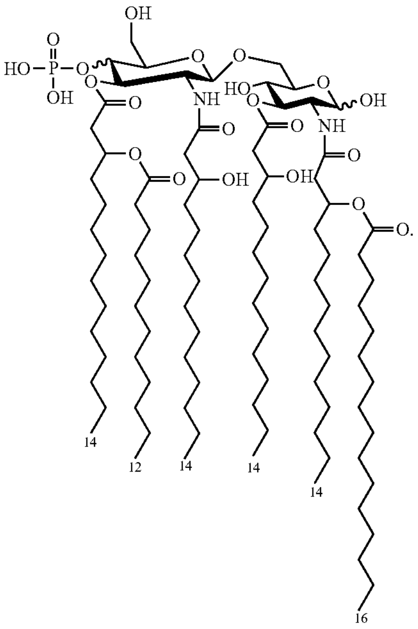
In another embodiment, the invention provides a compound of the formula:
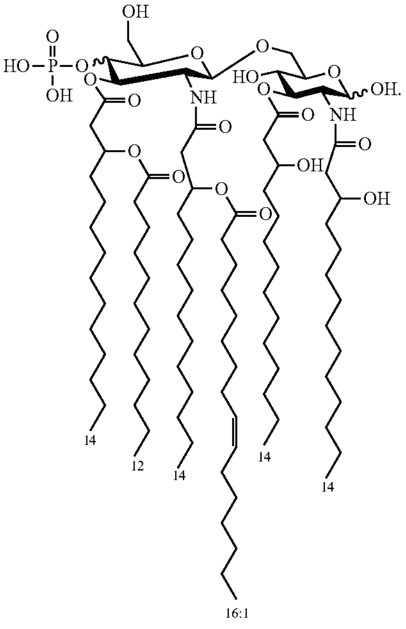
In another embodiment, the invention provides a compound of the formula:
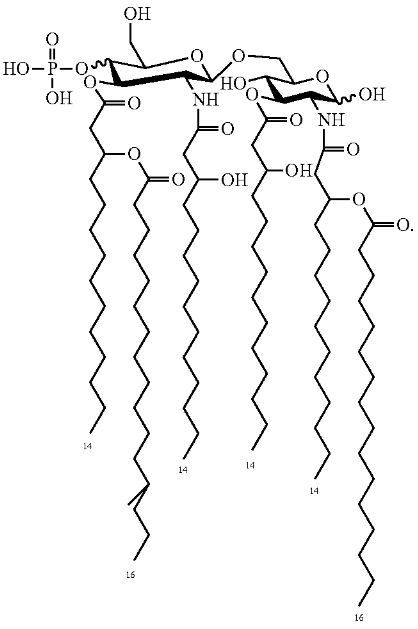

In another embodiment, the invention provides a compound of the formula:
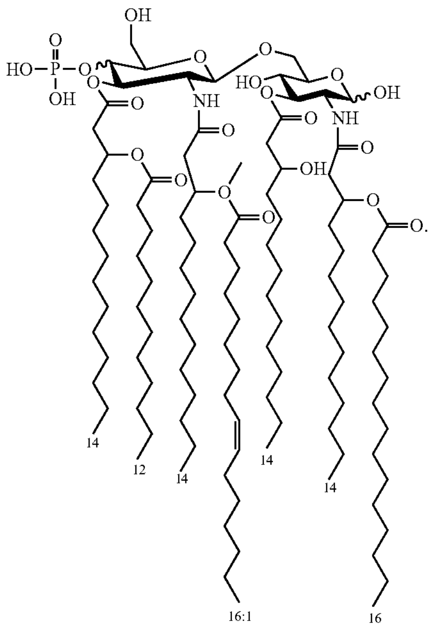
In another embodiment, the invention provides a compound of the formula:
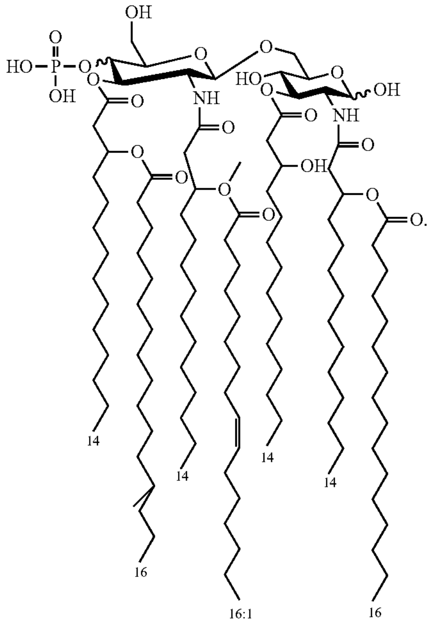
In another embodiment, the invention provides a compound of the formula:
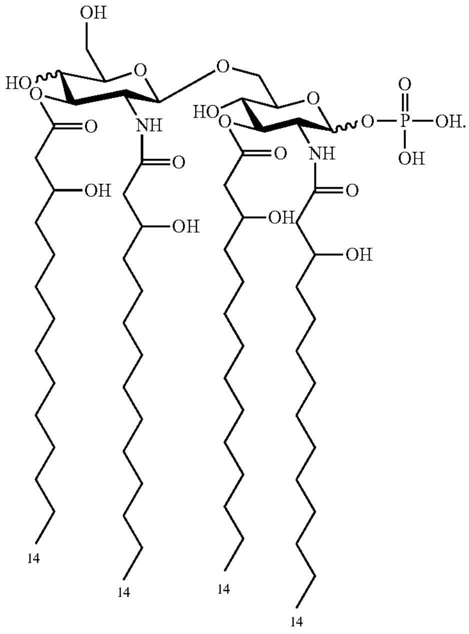
In another embodiment, the invention provides a compound of the formula:
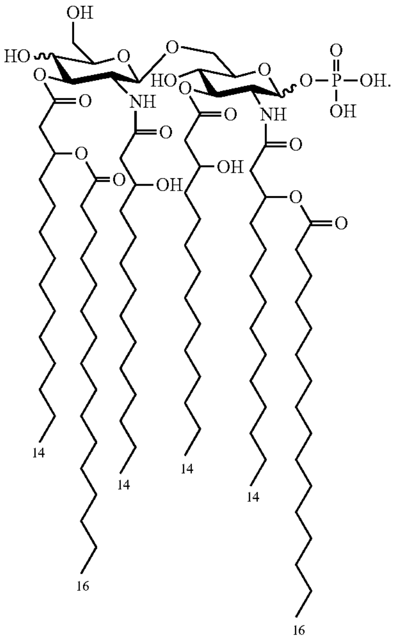

In another embodiment, the invention provides a compound of the formula:
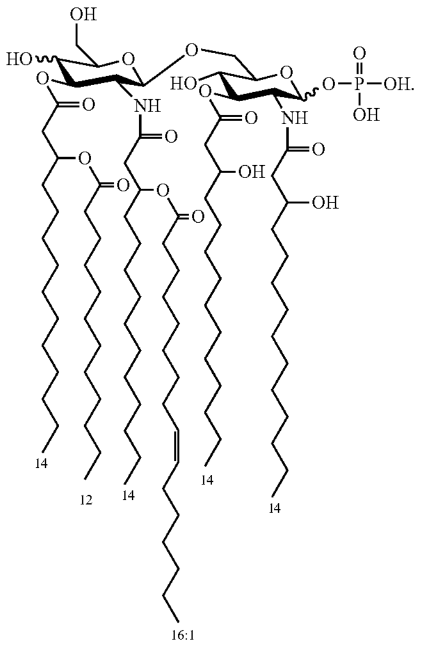
In another embodiment, the invention provides a compound of the formula:
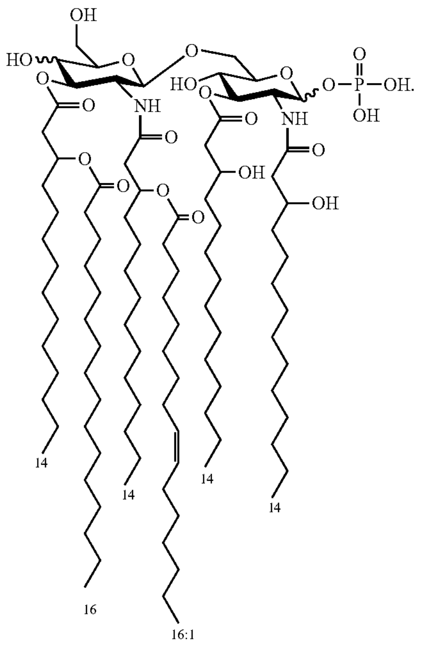
In another embodiment, the invention provides a compound of the formula:
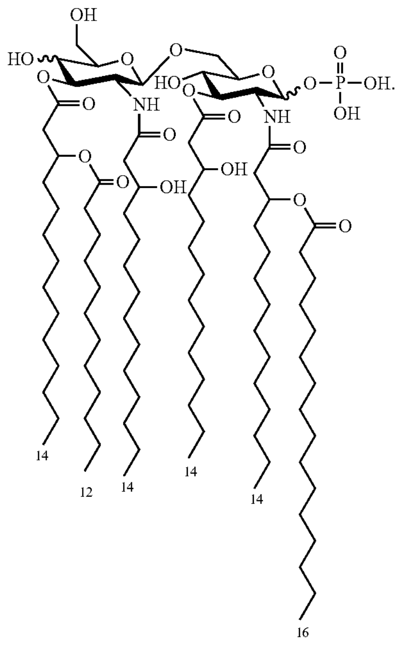
In another embodiment, the invention provides a compound of the formula:
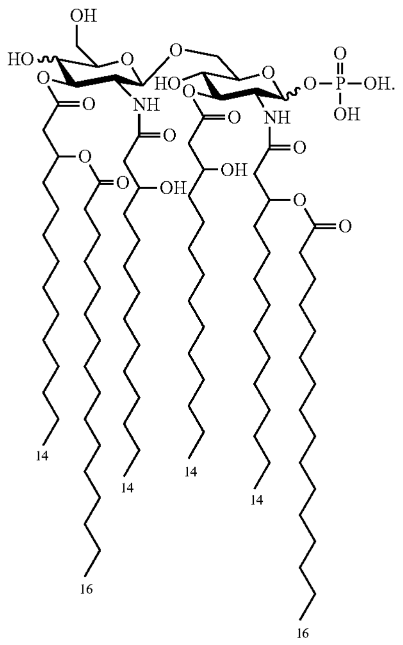

In another embodiment, the invention provides a compound of the formula:

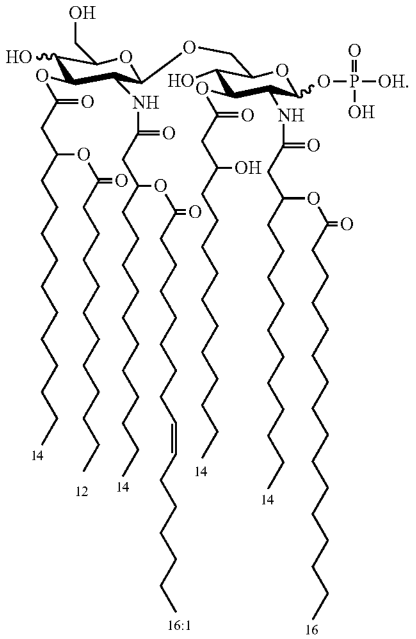

In another embodiment, the invention provides a compound of the formula:

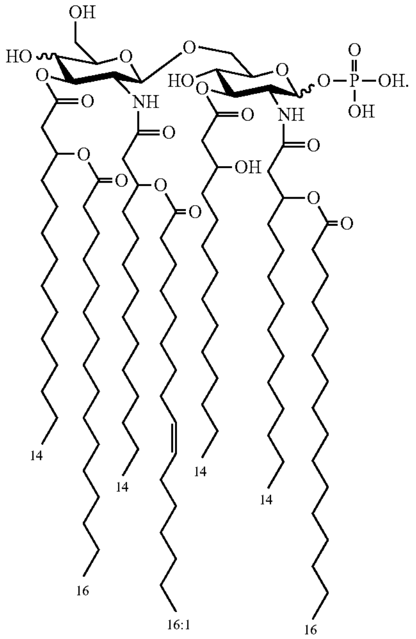

Pharmaceutically acceptable derivatives, such as prodrugs, and salts of the above-mentioned compounds are also contemplated by the present disclosure.

In another embodiment, the invention comprises a pharmaceutical composition of any of the compounds or combination thereof in combination with a pharmaceutically acceptable carrier.

In another embodiment, the invention provides a method of treating or preventing sepsis in a subject, comprising administering to the subject an effective amount of an anti-sepsis lipid A (ASLA) based therapeutic of the formula

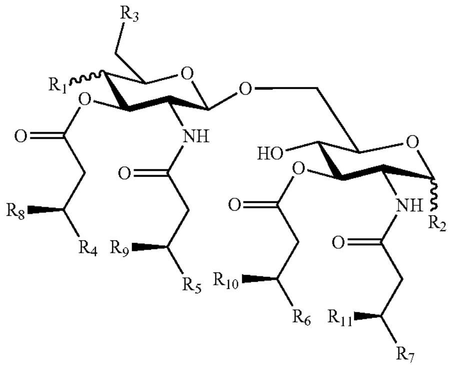

wherein $R_1$ and $R_2$ may be H, OH, protonated phosphate, a phosphate salt, a sugar phosphonate, or a mono-, di- or poly-saccharide, $R_3$ may be OH or a mono-, di- or poly-saccharide, $R_4$, $R_5$, $R_6$ and $R_7$ may be an alkyl or alkenyl chain of up to 13 carbons (for a chain of 16 carbons), and $R_8$, $R_9$, $R_{10}$ and $R_{11}$ may be H, OH, or an alkyl or alkenyl ester of up to 16 carbons, or a salt thereof.

Sepsis is characterized by the body's response to an infection. An infection is caused by microorganisms or bacteria invading the body and can be limited to a particular body region or can be widespread in the bloodstream. Sepsis is often a life threatening clinical syndrome that arises through the innate response to infection. Sepsis is regarded as a severe systemic inflammatory response syndrome (SIRS) caused by bacterial infection such as wounds, puerperium, and diseases. The character of the SIRS is hypercytokinemia, and the blood pressure is decreased by dilation of the blood vessels caused by inflammatory materials, e.g., cytokines, and toxins secreted by infected bacteria. A significant progress of hypotension causes a lack of blood flow in each site of the body to increase a risk of causing dysfunction of each organ. In order to avoid multiple organ failure, the heart increases the heart rate to increase the blood flow. This overload on the heart causes cardiac hypofunction, which can lead to a chronic lack of blood supply to important organs to cause a septic shock state, resulting in "multiple organ failure." The body may develop this inflammatory response by the immune system to microbes in the blood, urine, lungs, skin, or other tissues. Severe sepsis can be characterized by the systemic inflammatory response, plus infection, plus the presence of organ dysfunction. Sepsis can lead to multiple organ dysfunction syndrome (MODS) (formerly known as multiple organ failure), and death. Organ dysfunction may result from local changes in blood flow, from sepsis-induced hypotension (<90 mmHg or a reduction of ≥40 mmHg from baseline) and from diffuse intravascular coagulation.

Bacteremia is the presence of viable bacteria in the bloodstream. Likewise, the terms viremia and fungemia simply refer to viruses and fungi in the bloodstream. These terms say nothing about the consequences this has for the body. For example, bacteria can be introduced into the bloodstream during toothbrushing. This form of bacteremia almost never causes problems in normal individuals. However, bacteremia associated with certain dental procedures can cause bacterial infection of the heart valves (known as endocarditis) in high-risk patients. Conversely, a systemic inflammatory response syndrome can occur in patients without the presence of infection, for example in those with burns, polytrauma, or the initial state in pancreatitis and chemical pneumonitis.

In addition to symptoms related to the provoking infection, sepsis is characterized by presence of acute inflammation present throughout the entire body, and is, therefore, frequently associated with fever and elevated white blood cell count (leukocytosis) or low white blood cell count and lower-than-average temperature, and vomiting. The current concept of sepsis is that the host's immune response to the infection causes most of the symptoms of sepsis, resulting in hemodynamic consequences and damage to organs. This host response has been termed systemic inflammatory response syndrome (SIRS) and is characterized by an elevated heart rate (above 90 beats per minute), high respiratory rate (above 20 breaths per minute or a partial pressure of carbon dioxide in the blood of less than 32), abnormal white blood cell count (above 12,000, lower than 4,000, or greater than 10% band forms) and elevated or lowered body temperature, i.e. under 36° C. (97° F.) or over 38° C. (100° F.). Sepsis is differentiated from SIRS by the presence of a known or suspected pathogen. For example, SIRS and a positive blood culture for a pathogen indicates the presence of sepsis. However, in many cases of sepsis no specific pathogen is identified. As used herein, treatment or prevention of "sepsis" encompasses treatment or prevention of sepsis, severe sepsis, septic shock, SIRS and/or MODS.

As used herein, the terms "treatment" or "treating" relate to any treatment of a condition of interest (e.g., sepsis), including but not limited to therapeutic treatment, which can include inhibiting the progression of a condition of interest; arresting or preventing the further development of a condition of interest; reducing the severity of a condition of interest; ameliorating or relieving symptoms associated with a condition of interest; and causing a regression of a condition of interest or one or more of the symptoms associated with a condition of interest.

In some embodiments, the anti-sepsis lipid A (ASLA) based therapeutic is used for prophylactic treatment which can include preventing a condition such as sepsis. The degree of prevention achieved can be total or partial. In some embodiments, the treatment includes inhibiting the development of sepsis. In some embodiments, the treatment reduces the severity of sepsis that develops in the subject.

In some embodiments, administering the anti-sepsis lipid A (ASLA) based therapeutic reduces one or more of the symptoms associated with or the causes of sepsis. For example, in some embodiments, administering the anti-sepsis lipid A (ASLA) based therapeutic normalizes a body temperature of the subject, reduces an amount of blood urea nitrogen in the subject, increases arterial oxygen levels in the subject, improves diaphragm contractility in the subject, or a combination thereof. In further embodiments, administering the anti-sepsis lipid A (ASLA) based therapeutic decreases an amount of mitogen activated protein kinase (MAPK) signaling in a cell of the subject, decreases an amount of signal transducer and activation of transcription (stat) signaling in a cell of the subject, decreases an amount of NF-κB activation in a cell of the subject, or a combination thereof. In still further embodiments, administering the anti-sepsis lipid A (ASLA) based therapeutic reduces an amount of an inflammatory marker in the subject, including, in some embodiments, a reduction in the amount of protein nitrosylation, glutathione S-transferase, myeloperoxidase, leukemia inhibitory factor, interferon gamma, interleukin 6, macrophage inflammatory protein, monocyte chemotactic protein, and tumor necrosis factor alpha, or combinations thereof. In some embodiments, administering the anti-sepsis lipid A (ASLA) based therapeutic increases an amount of P-selectin and/or vascular cell adhesion molecule (VCAM) expression in a cell of the subject Various methods known to those skilled in the art can be used to determine a reduction in the amount of a marker or symptom associated with sepsis, or other disease or disorder, in a subject. For example, in some embodiments, the amounts of expression of an inflammatory marker in a subject can be determined by probing for mRNA of the gene encoding the inflammatory marker in a biological sample obtained from the subject (e.g., a tissue sample, a urine sample, a saliva sample, a blood sample, a serum sample, a plasma sample, or sub-fractions thereof) using any RNA identification assay known to those skilled in the art. Briefly, RNA can be extracted from the sample, amplified, converted to cDNA, labeled, and allowed to hybridize with probes of a known sequence, such as known RNA hybridization probes immobilized on a substrate, e.g., array, or microarray, or quantitated by real time PCR (e.g., quantitative real-time PCR, such as available from Bio-Rad Laboratories, Hercules, Calif.). Because the probes to which the nucleic acid molecules of the sample are bound are known, the molecules in the sample can be identified. In this regard, DNA probes for one or more of the mRNAs encoded by the inflammatory genes can be immobilized on a substrate and provided for use in practicing a method in accordance with the presently-disclosed subject matter.

In some embodiments, mass spectrometry and/or immunoassay devices and methods can also be used to measure the inflammatory cytokines in samples, although other methods can also be used and are well known to those skilled in the art. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Any suitable immunoassay can be utilized, for example, enzyme-linked immunoassays (ELISA), radioimmunoassays (RIAs), competitive binding assays, and the like. Specific immunological binding of the antibody to the inflammatory molecule can be detected directly or indirectly. Direct labels include fluorescent or luminescent tags, metals, dyes, radionucleotides, and the like, attached to the antibody. Indirect labels include various enzymes well known in the art, such as alkaline phosphatase, horseradish peroxidase and the like.

The use of immobilized antibodies or fragments thereof specific for the inflammatory molecules is also contemplated by the present invention. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

Mass spectrometry (MS) analysis can be used, either alone or in combination with other methods (e.g., immunoassays), to determine the presence and/or quantity of an inflammatory molecule in a subject. Exemplary MS analyses that can be used in accordance with the present invention include, but are not limited to: liquid chromatography-mass spectrometry (LC-MS); matrix-assisted laser desorption/ionization time-of-flight MS analysis (MALDI-TOF-MS), such as for example direct-spot MALDI-TOF or liquid chromatography MALDI-TOF mass spectrometry analysis; electrospray ionization MS (ESI-MS), such as for example liquid chromatography (LC) ESI-MS; and surface enhanced laser desorption/ionization time-of-flight mass spectrometry analysis (SELDI-TOF-MS). Each of these types of MS analysis can be accomplished using commercially-available spectrometers, such as, for example, triple quadropole mass spectrometers. Methods for utilizing MS analysis to detect the presence and quantity of peptides, such as inflammatory cytokines, in biological samples are known in the art. See, e.g., U.S. Pat. Nos. 6,925,389; 6,989,100; and 6,890,763 for further guidance, each of which are incorporated herein by this reference.

In some embodiments, a qualitative assessment is performed, e.g., detecting the presence or absence of the expression of an inflammatory marker in a subject. In some embodiments, a quantitative assessment is performed, e.g., determining an amount of decrease in the level of an inflammatory marker in a subject. Such quantitative assessments can be made, for example, using one of the above-mentioned methods, as will be understood by those skilled in the art.

In some embodiments, measuring a reduction in the amount of a certain feature (e.g., cytokine levels) or an improvement in a certain feature (e.g., inflammation) in a subject can be performed by a statistical analysis. For example, a reduction in an amount of inflammatory markers in a subject can be compared to control levels of inflammatory markers, and an amount of inflammatory markers of less than or equal to the control level can be indicative of a reduction in the amount of inflammatory markers, as evidenced by a level of statistical significance. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. In some embodiments, confidence intervals are 90%, 95%, 97.5%, 98%, 99%, 99.5%, 99.9% and 99.99%, while in some embodiments, p values are selected from 0.1, 0.05, 0.025, 0.02, 0.01, 0.005, 0.001, and 0.0001.

The sepsis to be treated or prevented can be attributed to an infection or a risk thereof in the subject by a Gram-negative microorganism. The Gram-negative microorganism is not particularly limiting. Exemplary Gram-negative microorganisms include species in any of genera *Escherichia, Shigella, Neisseria, Moraxella, Bordetella, Borrelia, Brucella, Chlamydia, Haemophilus, Legionella, Pseudomonas, Yersinia, Helicobacter, Salmonella*, and *Vibrio*. In some embodiments, the Gram-negative microorganism is selected from *Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri*; Bacillaceae, such as *Bacillus anthracis, Bacillus subtilis, Bacillus thuringiensis, Bacillus stearothermophilus* and *Bacillus cereus*; Enterobacteriaceae, such as *Escherichia coli, Enterobacter* (e.g. *Enterobacter aerogenes, Enterobacter agglomerans* and *Enterobacter cloacae*), *Citrobacter* (such as *Citrob. freundii* and *Citrob. divernis*), *Hafnia* (e.g. *Hafnia alvei*), *Erwinia* (e.g. *Erwinia persicinus*), *Morganella morganii, Salmonella* (*Salmonella enterica* and *Salmonella typhi*), *Shigella* (e.g. *Shigella dysenteriae, Shigella flexneri, Shigella boydii* and *Shigella sonnei*), *Klebsiella* (e.g. *Klebs. pneumoniae, Klebs. oxytoca, Klebs. ornitholytica, Klebs. planticola, Klebs. ozaenae, Klebs. terrigena, Klebs. granulomatis* (*Calymmatobacterium granulomatis*) and *Klebs. rhinoscleromatis*), *Proteus* (e.g. *Pr. mirabilis, Pr. rettgeri* and *Pr. vulgaris*), *Providencia* (e.g. *Providencia alcalifaciens, Providencia rettgeri* and *Providencia stuartii*), *Serratia* (e.g. *Serratia marcescens* and *Serratia liquifaciens*), and *Yersinia* (e.g. *Yersinia enterocolitica, Yersinia pestis* and *Yersinia pseudotuberculosis*); Enterococci (e.g. *Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus* and *Enterococcus solitarius*); *Helicobacter* (e.g. *Helicobacter pylori, Helicobacter cinaedi* and *Helicobacter fennelliae*); *Acinetobacter* (e.g. *A. baumanii, A. calcoaceticus, A. haemolyticus, A. johnsonii, A. junii, A. Iwoffi* and *A. radioresistens*); *Pseudomonas* (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzeri*); *Bacteriodes fragilis; Peptococcus* (e.g. *Peptococcus niger*); *Peptostreptococcus; Clostridium* (e.g. *C. perfringens, C. difficile, C. botulinum, C. tetani, C. absonum, C. argentinense, C. baratii, C. bifermentans, C. beijerinckii, C. butyricum, C. cadaveris, C. camis, C. celatum, C. clostridioforme, C. cochlearium, C. cocleatum, C. fallax, C. ghonii, C. glycolicum, C. haemolyticum, C. hastiforme, C. histolyticum, C. indolis, C. innocuum, C. irregulare, C. leptum, C. limosum, C. malenominatum, C. novyi, C. oroticum, C. paraputrificum, C. piliforme, C. putrefasciens, C. ramosum, C. septicum, C. sordelii, C. sphenoides, C. sporogenes, C. subterminale, C. symbiosum* and *C. tertium*); *Mycoplasma* (e.g. *M. pneumoniae, M. hominis, M. genitalium* and *M. urealyticum*); Mycobacteria (e.g. *Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celatum, Mycobacterium chubense, Mycobacterium confluentis, Mycobacterium conspicuum, Mycobacterium cookii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium microgenicum, Mycobacterium microti, Mycobacterium mucogenicum, Mycobacterium neoaurum, Mycobacterium nonchromogenicum, Mycobacterium peregrinum, Mycobac-*

*terium phlei, Mycobacterium scrofulaceum, Mycobacterium shimoidei, Mycobacterium simiae, Mycobacterium szulgai, Mycobacterium terrae, Mycobacterium thermoresistabile, Mycobacterium triplex, Mycobacterium triviale, Mycobacterium tusciae, Mycobacterium ulcerans, Mycobacterium vaccae, Mycobacterium wolinskyi* and *Mycobacterium xenopi*); *Haemophilus* (e.g. *Haemophilus influenzae, Haemophilus ducreyi, Haemophilus aegyptius, Haemophilus parainfluenzae, Haemophilus haemolyticus* and *Haemophilus parahaemolyticus*); *Actinobacillus* (e.g. *Actinobacillus actinomycetemcomitans, Actinobacillus equuli, Actinobacillus hominis, Actinobacillus lignieresii, Actinobacillus suis* and *Actinobacillus ureae*); *Actinomyces* (e.g. *Actinomyces israelii*); *Brucella* (e.g. *Brucella abortus, Brucella canis, Brucella melintensis* and *Brucella suis*); *Campylobacter* (e.g. *Campylobacter jejuni, Campylobacter coli, Campylobacter lari* and *Campylobacter fetus*); *Listeria monocytogenes; Vibrio* (e.g. *Vibrio cholerae* and *Vibrio parahaemolyticus, Vibrio alginolyticus, Vibrio carchariae, Vibrio fluvialis, Vibrio furnissii, Vibrio hollisae, Vibrio metschnikovii, Vibrio mimicus* and *Vibrio vulnificus*); *Erysipelothrix rhusopathiae*; Corynebacteriaceae (e.g. *Corynebacterium diphtheriae, Corynebacterium jeikeum* and *Corynebacterium urealyticum*); Spirochaetaceae, such as *Borrelia* (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and *Treponema* (*Treponema pallidum* ssp. *pallidum, Treponema pallidum* ssp. *endemicum, Treponema pallidum* ssp. *pertenue* and *Treponema carateum*); *Pasteurella* (e.g. *Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica* and *Pasteurella stomatis*); *Bordetella* (e.g. *Bordetella bronchiseptica, Bordetella hinzii, Bordetella holmseii, Bordetella parapertussis, Bordetella pertussis* and *Bordetella trematum*); Nocardiaceae, such as *Nocardia* (e.g. *Nocardia asteroides* and *Nocardia brasiliensis*); *Rickettsia* (e.g. *Ricksettsii* or *Coxiella burnetii*); *Legionella* (e.g. *Legionalla anisa, Legionalla birminghamensis, Legionalla bozemanii, Legionalla cincinnatiensis, Legionalla dumoffii, Legionalla feeleii, Legionalla gormanii, Legionalla hackeliae, Legionalla israelensis, Legionalla jordanis, Legionalla lansingensis, Legionalla longbeachae, Legionalla maceachemii, Legionalla micdadei, Legionalla oakridgensis, Legionalla pneumophila, Legionalla sainthelensi, Legionalla tucsonensis* and *Legionalla wadsworthii*); *Moraxella catarrhalis; Cyclospora cayetanensis; Entamoeba histolytica; Giardia lamblia; Trichomonas vaginalis; Toxoplasma gondii; Stenotrophomonas maltophilia; Burkholderia cepacia; Burkholderia mallei* and *Burkholderia pseudomallei; Francisella tularensis; Gardnerella* (e.g. *Gardneralla vaginalis* and *Gardneralla mobiluncus*); *Streptobacillus moniliformis*; Flavobacteriaceae, such as *Capnocytophaga* (e.g. *Capnocytophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*); *Bartonella* (*Bartonella bacilliformis, Bartonella clarridgeiae, Bartonella elizabethae, Bartonella henselae, Bartonella quintana* and *Bartonella vinsonii arupensis*); *Leptospira* (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*); *Spirillium* (e.g. *Spirillum minus*); *Baceteroides* (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*); *Prevotella* (e.g. *Prevotella bivia, Prevotella buccae, Prevotella corporis, Prevotella dentalis* (*Mitsuokella dentalis*), *Prevotella denticola, Prevotella disiens, Prevotella enoeca, Prevotella heparinolytica, Prevotella intermedia, Prevotella loeschii, Prevotella melaninogenica, Prevotella nigrescens, Prevotella oxalis, Prevotella oris, Prevotella oulora, Prevotella tannerae, Prevotella venoralis* and *Prevotella zoogleoformans*); *Porphyromonas* (e.g. *Porphyromonas asaccharolytica, Porphyromonas cangingivalis, Porphyromonas canons, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levii* and *Porphyromonas macacae*); *Fusobacterium* (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*); *Chlamydia* (e.g. *Chlamydia trachomatis*); *Cryptosporidium* (e.g. *C. parvum, C. hominis, C. canis, C. felis, C. meleagridis* and *C. muris*); *Chlamydophila* (e.g. *Chlamydophila abortus* (*Chlamydia psittaci*), *Chlamydophila pneumoniae* (*Chlamydia pneumoniae*) and *Chlamydophila psittaci* (*Chlamydia psittaci*)); *Leuconostoc* (e.g. *Leuconostoc citreum, Leuconostoc cremoris, Leuconostoc dextranicum, Leuconostoc lactis, Leuconostoc mesenteroides* and *Leuconostoc pseudomesenteroides*); *Gemella* (e.g. *Gemella bergeri, Gemella haemolysans, Gemella morbillorum* and *Gemella sanguinis*); and *Ureaplasma* (e.g. *Ureaplasma parvum* and *Ureaplasma urealyticum*).

In some embodiments, the Gram-negative microorganism is selected from the group consisting of *Escherichia coli, Neisseria meningitidis, Klebsiella pneumoniae, Pseudomonas aeruginosa*, and *Acinetobacter baumannii.*

As used herein, the term "subject" includes both human and animal subjects. The term "subject" includes a human or other animal at risk of developing or suffering from sepsis, severe sepsis, septic shock, SIRS and/or MODS. Veterinary therapeutic uses are also provided. Examples of non-human mammals include, but are not limited to, cats, dogs, swine, including pigs, hogs, and wild boars, ruminants and/or ungulates such as cattle, oxen, sheep, giraffes, deer, goats, bison, and camels, and horses. Also provided is the treatment of birds as well as fowl, and more particularly domesticated fowl, i.e., poultry, such as turkeys, chickens, ducks, geese, guinea fowl, and the like.

In some embodiments, the anti-sepsis lipid A (ASLA) based therapeutic is provided to a subject having sepsis. In some embodiments, the anti-sepsis lipid A (ASLA) based therapeutic is provided to a subject who does not have sepsis, but who is at risk of developing sepsis. A person at risk of developing sepsis can be a person infected with a Gram-negative microorganism, for example. In some embodiments, the anti-sepsis lipid A (ASLA) based therapeutic is provided to a subject suspected of having sepsis. In some embodiments, the anti-sepsis lipid A (ASLA) based therapeutic is provided to a subject infected with a Gram-negative microorganism. In some embodiments, the subject can be at risk for developing an infection and subsequent sepsis, e.g., by having an open wound and/or an open fracture. In some embodiments, the subject can be a soldier who is in an active combat situation or who has recently been wounded. In some embodiments, the subject is administered the anti-sepsis lipid A (ASLA) based therapeutic before, during and/or after a surgical procedure, which can present a risk for the subject of developing an infection and later sepsis. In some embodiments, the subject has an infection and is administered one or more antibiotics/drugs, which can create a risk of releasing a sepsis inducing compound from the microorganism during treatment.

In some embodiments, the anti-sepsis lipid A (ASLA) based therapeutic administered is selected from the group consisting of

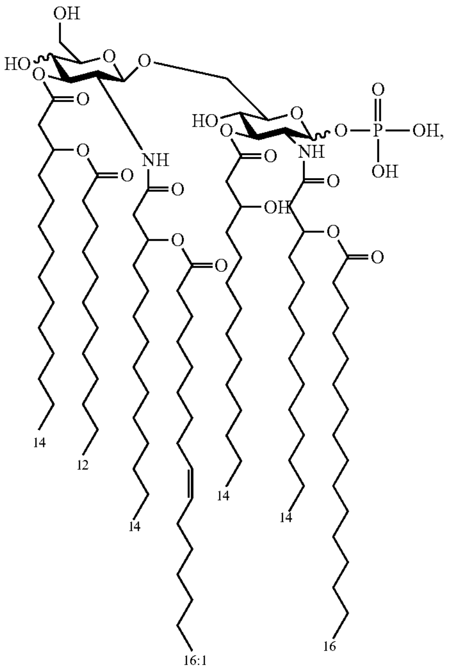

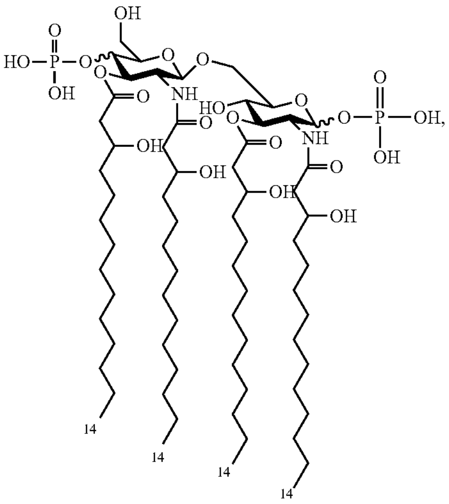

-continued

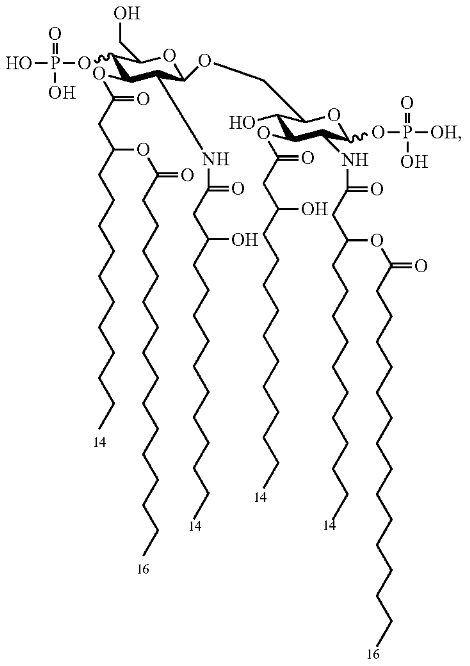

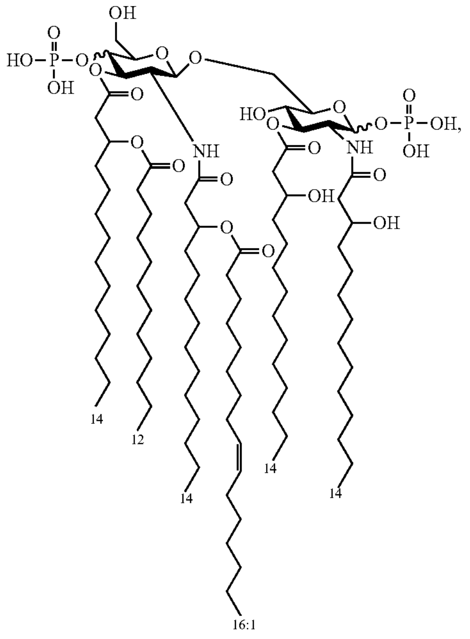

-continued
-continued
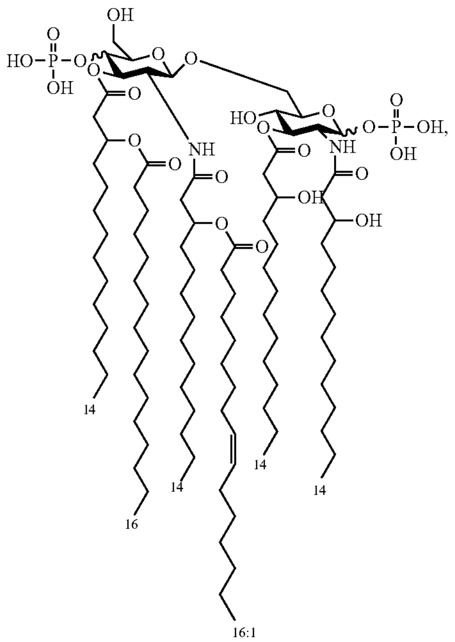
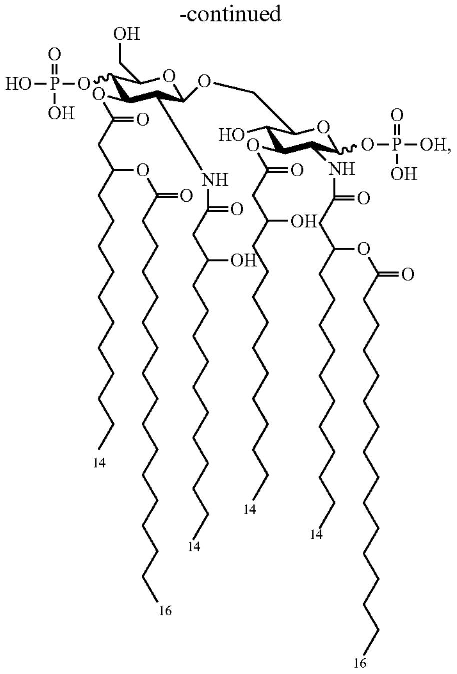
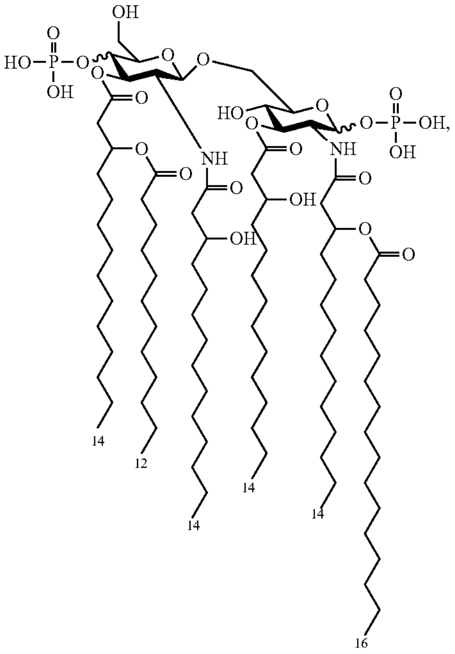
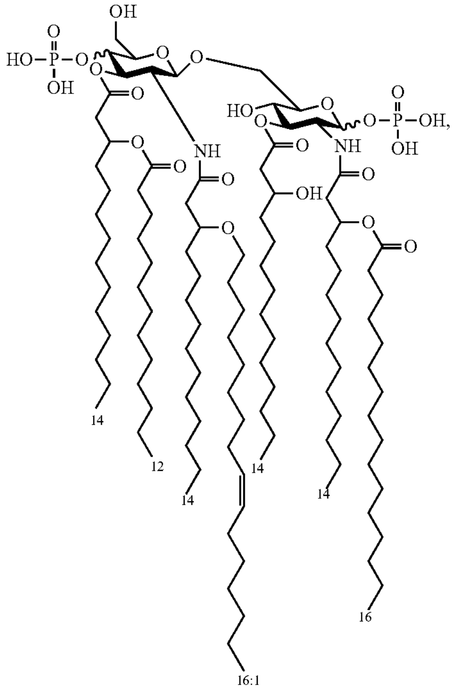

-continued
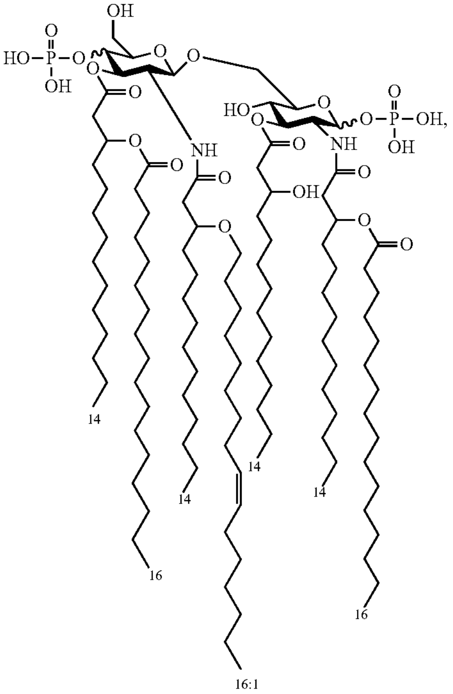
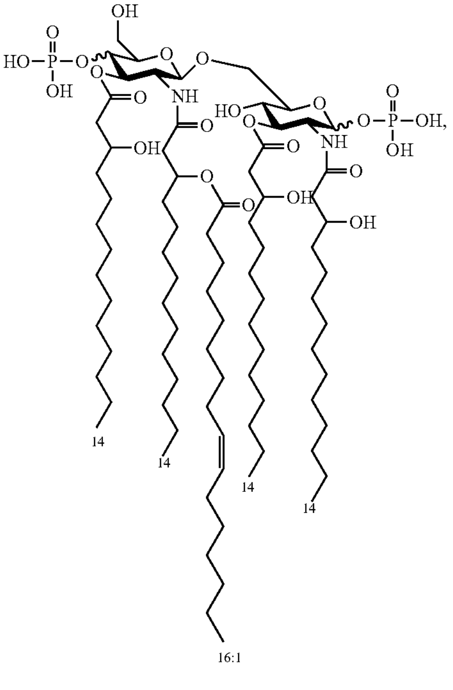
-continued
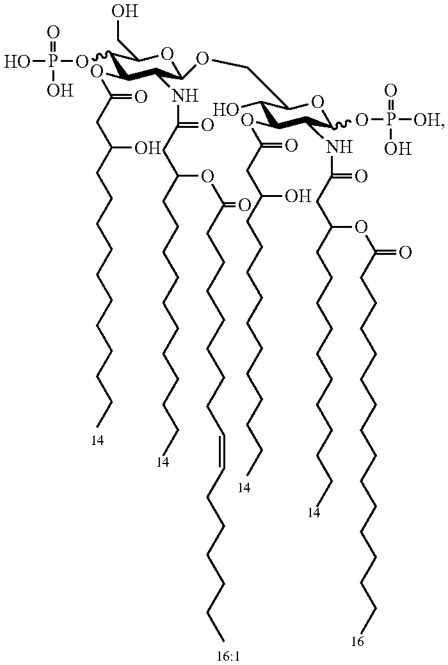
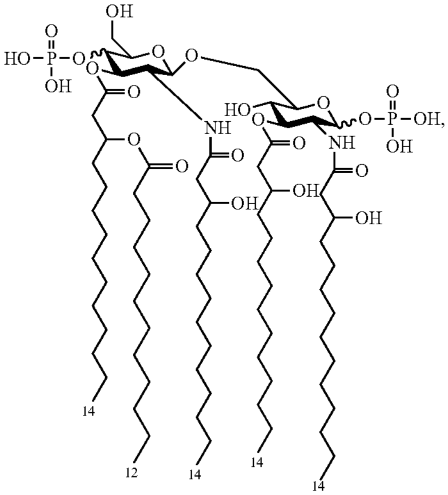
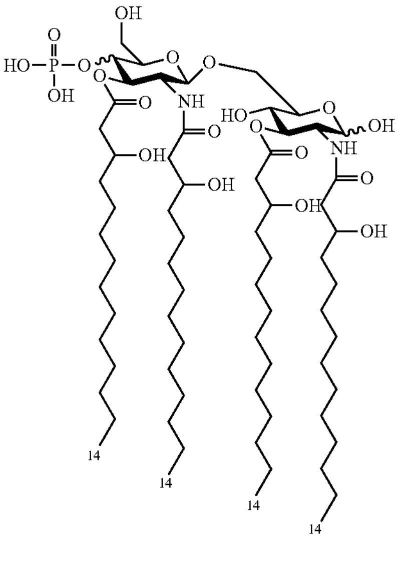

-continued
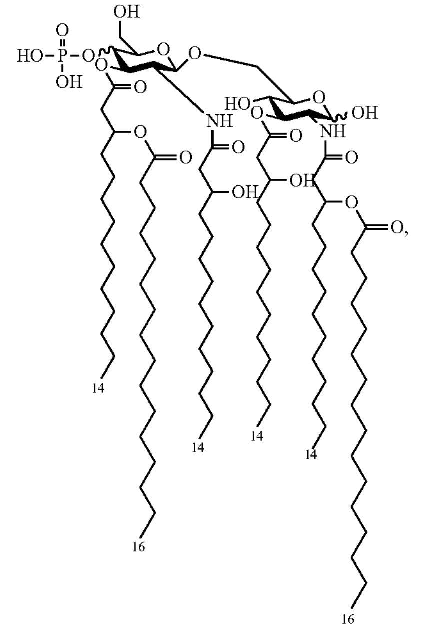
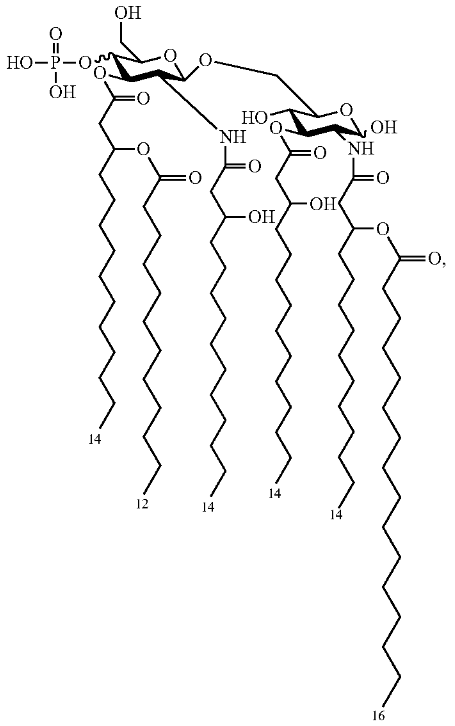
-continued
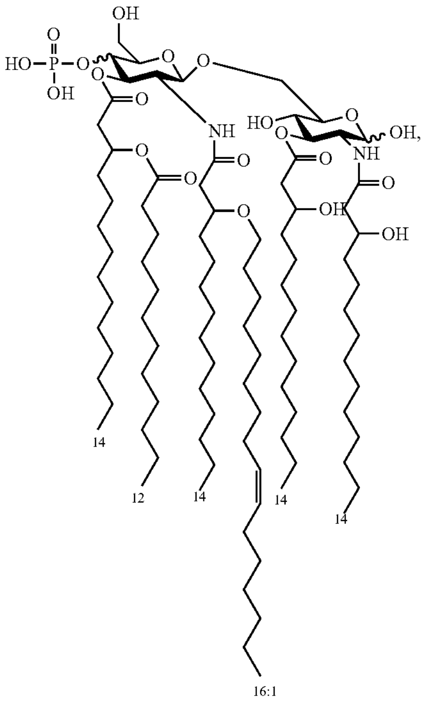
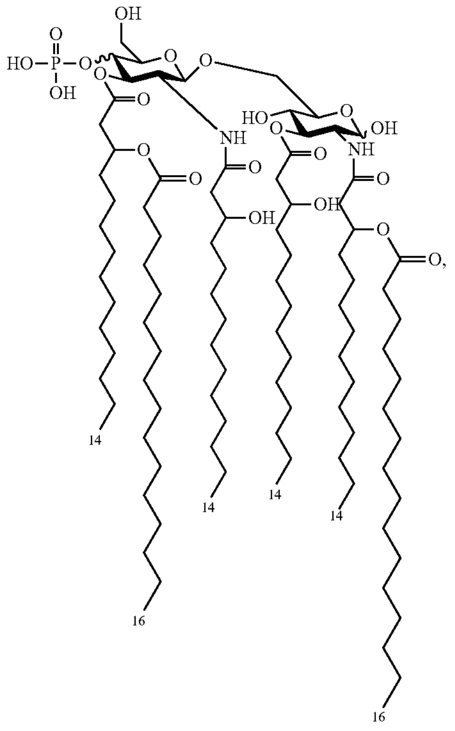

-continued
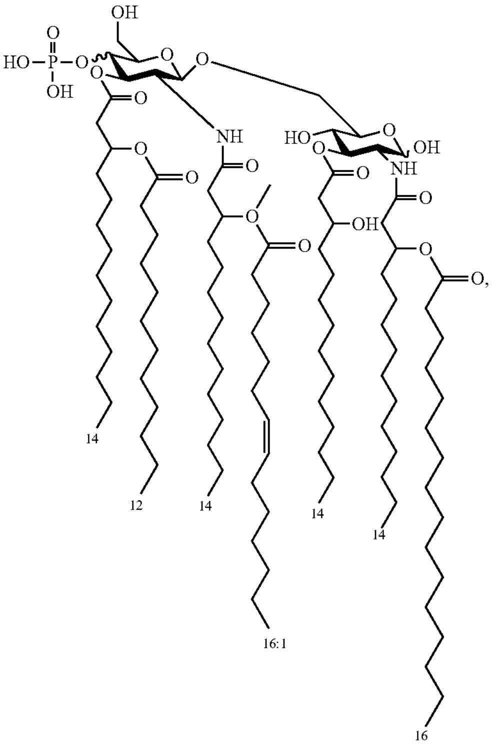
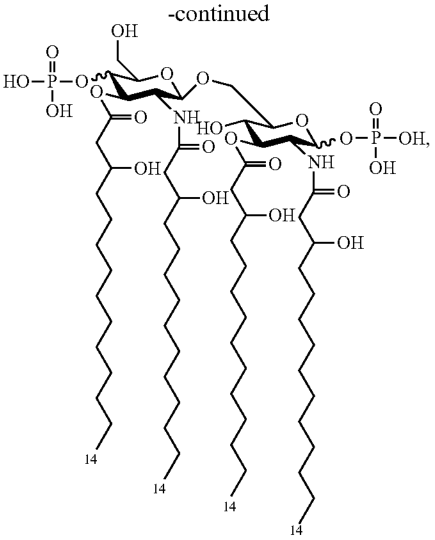
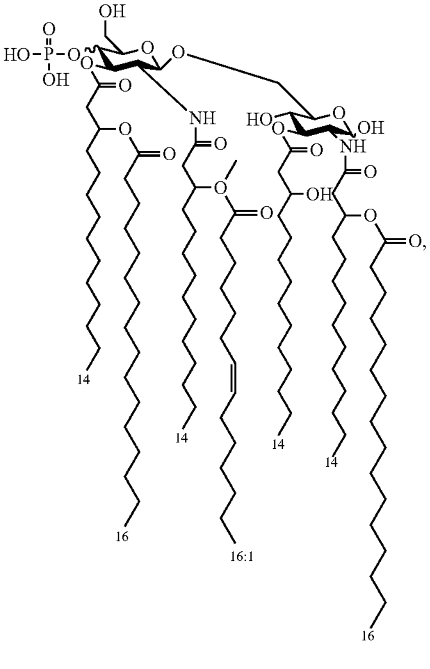
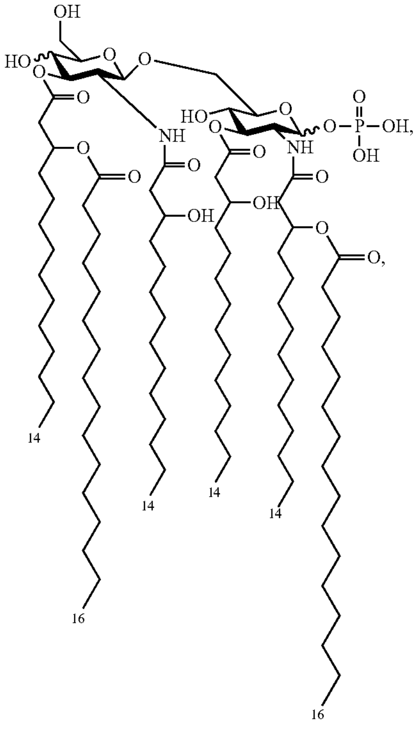

-continued
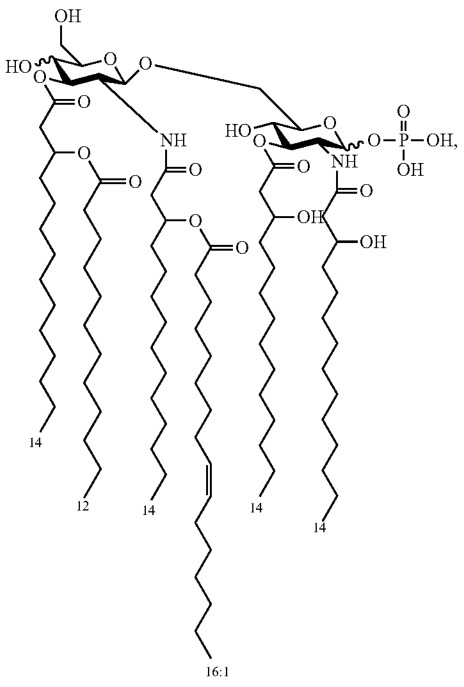
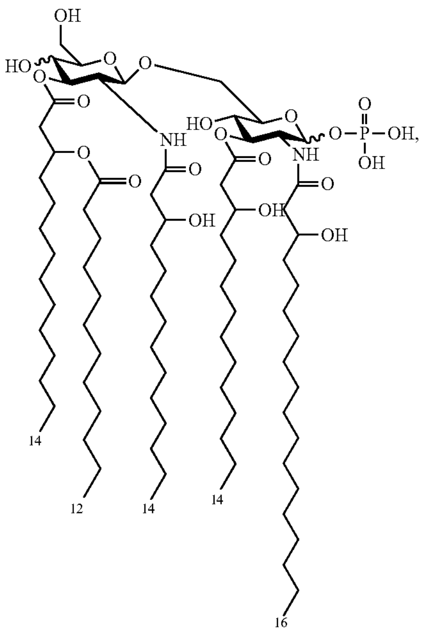
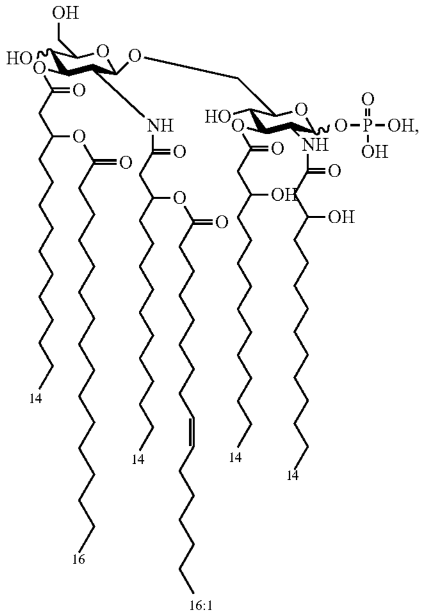
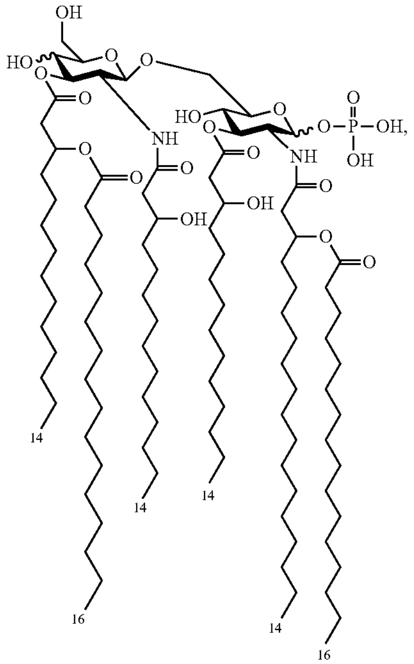

-continued

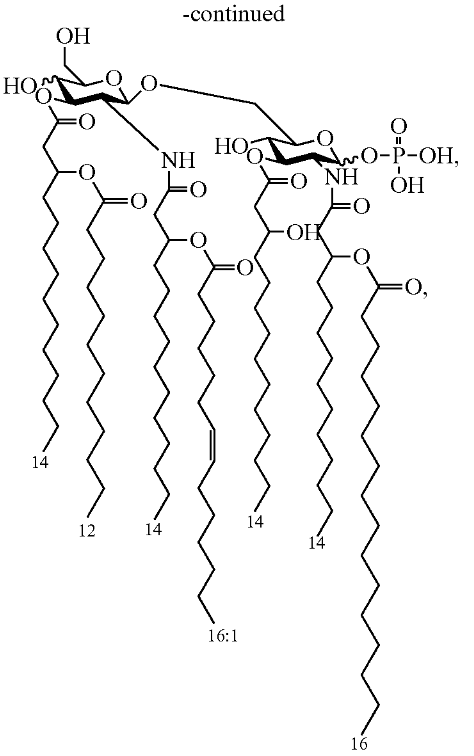

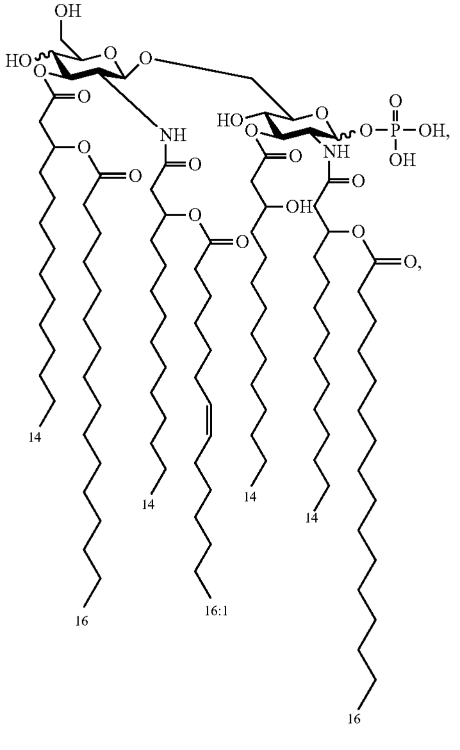

and combinations thereof.

The manner of administration of the therapeutic composition may be varied widely. Any of the conventional methods for administration are applicable. For example, the composition may be conventionally administered intravenously, intradermally, intraarterially, intraperitoneally, intralesionally, intracranially, intraarticularly, intraprostaticaly, intrapleurally, intratracheally, intranasally, intravitreally, intravaginally, intratumorally, intramuscularly, intraperitoneally, subcutaneously, intravesicularly, mucosally, intrapericardially, orally, rectally, nasally, topically, in eye drops, locally, using aerosol, injection, infusion, continuous infusion, localized perfusion, via a catheter, via a lavage, in creams, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

Regardless of the route of administration, the anti-sepsis lipid A (ASLA) based therapeutic used in accordance with the invention is typically administered in an amount effective to achieve the desired response. As such, the term "effective amount" is used herein to refer to an amount that is of sufficient quality and quantity to neutralize, ameliorate, modulate, or reduce the cause of or effect of lipopolysaccharide caused sepsis or inflammation. By "ameliorate," "modulate," or "reduce" is meant a lessening or reduction or prophylactic prevention of the detrimental effect of the disorder in the subject receiving the therapy, thereby resulting in "protecting" the subject. A "sufficient amount" or "effective amount" or "therapeutically effective amount" of an administered composition is that volume or concentration which causes or produces a measurable change from the pre-administration state in the cell or patient. The subject of the invention is preferably a human subject, however, it can be envisioned that any animal with endotoxemia or sepsis or at risk thereof can be treated in a method of the present invention.

Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. In some embodiments, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

A dosing schedule may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art. In some embodiments, the anti-sepsis lipid A (ASLA) based therapeutic is administered in a dose of between about 0.01 mg/kg to about 100 mg/kg body weight. In some embodiments, the dose administered is about 1-50 mg/kg body weight of the subject. In some embodiments, the dose administered is about 5-25 mg/kg body weight of the subject. In some embodiments, the dose administered is about 10 mg/kg body weight of the subject.

In some embodiments, the methods of the invention reduce sepsis or risk of sepsis by at least 20%, more preferably by at least 50%, even more preferably by 80% or greater, and also preferably, in a dose-dependent manner.

The form of the anti-sepsis lipid A (ASLA) based therapeutic is not particularly limiting. For example, the anti-sepsis lipid A (ASLA) based therapeutics can be in the form of a pharmaceutically acceptable salt. Mixtures of different forms, and compositions that include mixtures of forms are possible. In some embodiments, the anti-sepsis lipid A (ASLA) based therapeutics may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Non-limiting examples of pharmaceutically acceptable salts include sodium, potassium, lithium, calcium, magnesium, iron, zinc, hydrochloride, hydrobromide, hydroiodide, acetate, citrate, tartrate and maleate salts, and the like. Combinations of different salt forms are possible.

In some embodiments, the anti-sepsis lipid A (ASLA) based therapeutic is administered in combination with one or more additional therapies to treat sepsis.

In some embodiments, the additional therapy is administration of an antibiotic. In some embodiments, the antibiotic is selected from Amikacin, Gentamicin, Kanamycin, Neomycin, Netilmicin, Tobramycin, Paromycin, Streptomycin, Spectinomycin, Rifaximin, Ertapenem, Doripenem, Cilastatin, Meropenen, Cefadroxil, Cefazolin, Cefalexin, Cefaclor, Cefamandole, Cefoxitin, Cefoperazone, Cefotaxime, Ceftazidime, Ceftibuten, Cefepime, Ceftaroline fosamil, Ceftibiprole, Teicoplanin, Vancomycin, Telavancin, Dalbavancin, Clindamycin, Lincomycin, Daptomycin, Azithromycin, Clarithtomycin, Erythromycin, Roxithromycin, Telithromycin, Aztreonam, Furazolidone, Penicillin, Amoxicillin, Ampicillin, Piperacillin, Tazobactam, Tiracillin, Bacitracin, Colistin, Polymixin B, Ciprofloxacin, Enoxacin, Vancocin, Claforan, Ceftriaxone, Gentamicin, Gatifloxacin, Gemifloxacin, Lefofloxacin, Nalidixic acid, Norfloxacin, Ofloxacin, Mafenide, Sulfacetamide, Sulfadiazine, Sulfadimethoxine, Sulfamethoxazole, Sulfasalazine, Sulfisoxazole, Demeclocycline, Doxcycline, Mupirocin, Tigecycline, Minocycline, Oxytetracycline, Tetracycline, Clofazimine, Dapsone, Capreomycin, Cycloserine, Ethambutol, Isoniazid, Rifabutin, Thiamphenicol, Trimethoprim, Metranidzole and combinations thereof.

In some embodiments, the additional therapy is selected from a vasosupressor/vasoactive agents, Norepinephrine, Epinephrine, Vasopressin, Dopamine, Phenylephrine, Dobutamine, Midodrine, Levosimendan, Corticosteroids, and combinations thereof.

In some embodiments, more than one lipid A mimetic is employed in a therapeutic composition, including two, three, or more lipid A mimetics. The lipid A mimetic can be formulated for use as a pharmaceutical composition, including having an appropriate carrier excipient. A therapeutically effective amount of the composition(s) is employed, and the proper amount may be determined by any suitable method in the art. The composition can be delivered to the individual by any appropriate means, including by injection or orally. Multiple deliveries of the anti-sepsis lipid A (ASLA) based therapeutic(s) may be employed.

The delivery of the lipid A mimetic in a therapeutic composition can occur prior to exposure of the individual to a Gram-negative microorganism and/or following exposure of the individual to a Gram-negative microorganism.

In some embodiments, the compositions of the present invention are prepared to be pharmacologically acceptable. Pharmaceutical compositions of the present invention comprise an effective amount of one or more anti-sepsis lipid A (ASLA) based therapeutics dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The means of preparation of a pharmaceutical composition that contains at least one anti-sepsis lipid A (ASLA) based therapeutics or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The compositions may comprise different types of carriers depending on whether it is to be administered in solid, liquid or aerosol form, and whether it need to be sterile for such routes of administration as injection. Except insofar as any conventional carrier is incompatible with the active ingredient, its use in the therapeutic or pharmaceutical compositions is contemplated.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The composition may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the composition is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assailable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

In some embodiments, the composition must be stable under the conditions of manufacture and storage, and preserved against the contaminating action of microorganisms, such as bacteria and fungi.

In particular embodiments, prolonged absorption of an injectable composition can be brought about by the use in the compositions of agents delaying absorption, such as, for example, aluminum monostearate, gelatin or combinations thereof.

In some embodiments, it will be desirable to have multiple administrations of the composition. In some embodiments, the composition is administered 1, 2, 3, 4, 5, 6, 7, 8, 9 or at least 10 times to the subject.

Methods of Making the Anti-Sepsis Lipid A (ASLA) Based Therapeutics

The method for making the compounds is not limiting. For example, the compounds can be made by organic synthesis or with microorganisms. In some embodiments, the anti-sepsis lipid A (ASLA) based therapeutics can be produced by genetically engineering microorganisms. In some embodiments, the invention provides an approach of using Bacterial Enzymatic Combinatorial Chemistry (BECC) to make rationally-designed lipid A structures by modifying the lipid A structure of a lipopolysaccharide (LPS) or lipooligosaccharide (LOS) from a Gram-negative bacteria (such as an attenuated (BSL-2 approved) *Yersinia pestis* (Yp) strain). In some embodiments, this approach uses the lipid A structure present in LPS/LOS synthesized in bacteria as a lead molecule or structure to be modified by heterologous in trans expression of lipid A biosynthesis enzymes. These enzymes can be obtained from a wide variety of bacterial backgrounds with specificities for the removal or addition of fatty acid chain, phosphates moieties, and carbohydrates to the lipid A backbone. In some embodiments, one approach uses the non-stimulatory, hypoacylated, and bisphosphorylated lipid A structure present in LOS synthesized by a *Yersinia pestis* strain. As such, methods of the disclosure allow for the safe, cost effective, and efficient design of molecules with anti-sepsis activity. In some embodiments, the invention further provides a method of screening anti-sepsis molecules. The anti-sepsis capability of the molecules can be tested in vitro and in vivo.

In some embodiments, the invention provides a method of making an anti-sepsis lipid A (ASLA) based therapeutics of the formula

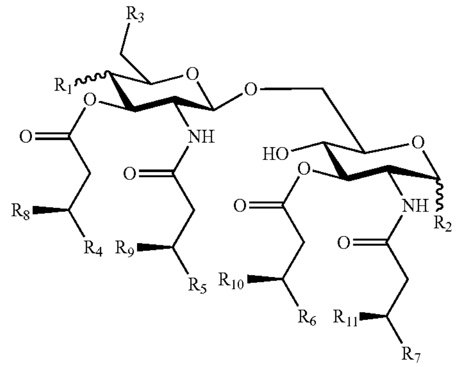

wherein $R_1$ and $R_2$ may be H, OH, protonated phosphate, a phosphate salt, a sugar phosphonate, or a mono-, di- or poly-saccharide, $R_3$ may be OH or a mono-, di- or poly-saccharide, $R_4$, $R_5$, $R_6$ and $R_7$ may be an alkyl or alkenyl chain of up to 13 carbons (for a chain of 16 carbons), and $R_8$, $R_9$, $R_{10}$ and $R_{11}$ may be H, OH, or an alkyl or alkenyl ester of up to 16 carbons, or a salt thereof, wherein the method comprises genetically engineering a Gram-negative microorganism to produce the anti-sepsis lipid A (ASLA) based therapeutic, and isolating the anti-sepsis lipid A (ASLA) based therapeutic from the microorganism. In some embodiments, the microorganism is cultured at a temperature ranging from about 12-28° C., e.g., about 26° C., while in other embodiments, the microorganism is cultured at a temperature ranging from about 30-39° C., e.g., about 37° C. In some embodiments, the structure of the produced ASLA compound can vary depending on which temperature the microorganism is cultured at.

In some embodiments, the invention provides modifications of LPS, the major component of the Gram-negative bacterial envelope, from *P. aeruginosa, Francisella subspecies, Bordetella* subspecies, *S. typhimurium, Acinetobacter baumannii, Burkholderia*, and *Yersiniae* subspecies, and in specific aspects the lipid A component of LPS is altered in one or more of these bacteria using methods of the disclosure. The modifications in the anti-sepsis lipid A (ASLA) based therapeutics may be of any kind, including modifications to the fatty acid content and/or number, the number of phosphates and/or modification thereof, and the number or type of sugar. In certain embodiments, the construction of new BECC-synthesized molecules concern altering the terminal phosphates on the glucosamine backbone of lipid A. In some embodiments, the bacteria used to produce the molecules is an Archaebacteria. In some embodiments, the bacteria is an extremophile, including an Acidophile; Alkaliphile; Anaerobe; Cryptoendolith; Halophile; Hyperthermophile; Hypolith; Lithoautotroph; Metallotolerant; Oligotroph; Osmophile; Piezophile; Polyextremophile; Psychrophile/Cryophile; Radioresistant; Thermoacidophile; or Xerophile, for example. In some embodiments, the bacteria in which the anti-sepsis lipid A (ASLA) based therapeutics are generated is an avirulent *Y. pestis* strain, such as one that has lost one or more virulence plasmids. In some embodiments, the strain is wild-type *Y. pestis* KIM6, although any number of the modified KIM6 strains may be employed (e.g., KIM6 ΔPhoP (regulator) could be made with LpxF+ (expressing a phosphatase) or KIM6 ΔLpxD (acyltransferase) could be made with a ΔPmrK (which would not add aminoarabinose).

In one embodiment, there is a method of generating an anti-sepsis lipid A (ASLA) based therapeutic, comprising the steps of obtaining a bacterial strain that has one or more of the following modifications: expresses one or more non-endogenous lipid A biosynthesis enzymes; expresses one or more endogenous lipid biosynthesis enzymes, wherein the enzyme is modified; and/or has modified regulation of one or more endogenous lipid biosynthesis enzymes; and subjecting the strain to conditions suitable for production of the lipooligosaccharide/lipid A composition. In some embodiments, the obtaining step is further defined as engineering the bacterial strain to have one or more of the modifications. In some cases, the engineering step comprises one or more of delivering a vector into the bacteria; and/or bacterial conjugation. In specific embodiments, the engineering step comprises delivering a vector into the bacteria, wherein the vector comprises sequence that encodes one or more non-endogenous lipid A biosynthesis enzymes. In specific embodiments, the one or more non-endogenous lipid A biosynthesis enzymes is an acyltransferase, deacylase, phosphatase, glycosyltransferase, or a mixture thereof, from another bacterial strain. In particular embodiments, the engineering step comprises modifying the bacteria to express a modified endogenous lipid biosynthesis enzyme. In some cases, the modified endogenous lipid biosynthesis enzyme comprises a mutation in the enzyme. In certain embodiments, the one or more modified endogenous lipid biosynthesis enzymes is an acyltransferase, deacylase, phosphatase, or glycosyltransferase. In some cases, the engineering step comprises modifying the bacteria to have modified regulation of expression of one or more endogenous lipid A biosynthesis enzymes. In specific embodiments, modifying the bacteria to have modified regulation of expression of one or more endogenous lipid biosynthesis enzymes is further defined as mutating a gene in the bacteria that is a regulatory gene for lipid A biosynthesis in the bacteria, including one defined as a sensor kinase, a response regulator, or both of a two-component regulatory system in the bacteria. In certain cases, the regulatory gene for lipid A biosynthesis is histidine kinase. In some cases, the one or more endogenous lipid biosynthesis enzymes is an acyltransferase, deacylase, phosphatase, or glycosyltransferase. In particular embodiments, the subjecting step comprises particular temperature conditions suitable for production of the lipooligosaccharide/lipid A composition.

In some embodiments of methods of generating an anti-sepsis lipid A (ASLA) based therapeutic, the anti-sepsis lipid A (ASLA) based therapeutic produced by the method has a modified level and/or content of fatty acid compared to the endogenous bacterial lipid A molecule or a reference lipid A molecule. In some embodiments, the anti-sepsis lipid A (ASLA) based therapeutic produced by the method has a modified number of phosphates compared to the endogenous bacterial lipid A molecule or a reference lipid A molecule. In some embodiments, the anti-sepsis lipid A (ASLA) based therapeutic produced by the method has modified phosphates compared to the endogenous bacterial lipid A molecule or a reference lipid A molecule. In particular aspect, the modified phosphates are further defined as having only one sugar (simple and aminosugars) or having an additional sugar linked to the phosphate or ethanolamine. In specific aspects, the anti-sepsis lipid A (ASLA) based therapeutic produced by the method has a modified sugar number and/or content compared to the endogenous bacterial lipid A molecule or a reference lipid A molecule. In some cases, the anti-sepsis lipid A (ASLA) based therapeutic comprises one or three or more sugars. The anti-sepsis lipid A (ASLA)

based therapeutic may comprise modified sugars selected from the group consisting of aminoarabinose, glucosamine, and galactosamine. In some cases, the method further comprises the step of analyzing extracts from the bacteria for the structure, function, or both of the anti-sepsis lipid A (ASLA) based therapeutic.

In some embodiments, the analyzing step comprises analyzing the structure of the anti-sepsis lipid A (ASLA) based therapeutic by performing one or more types of mass spectrometry, gas chromatography, or a combination thereof. In some cases, the analyzing step comprises analyzing the function of the anti-sepsis lipid A (ASLA) based therapeutic by measuring an anti-sepsis response of the anti-sepsis lipid A (ASLA) based therapeutic. In particular embodiments, the anti-sepsis response is conducted in vivo in an animal model for sepsis.

The bacterial strain to be utilized ideally is an avirulent strain. The skilled artisan recognizes that any naturally virulent bacteria may be genetically engineered to be avirulent or otherwise rendered to be avirulent by any means, including loss of one or more virulence factors, such as loss of at least one virulence plasmid and/or bacteriophage. In some cases, a naturally occurring avirulent version of a normally virulent bacteria may be employed.

In one aspect of this disclosure, one can "harness" the normal bacterial lipid A biosynthesis pathways present in all Gram-negative bacteria to synthesize structures based on the presence or absence of specific phosphate, acyl, and carbohydrate groups (for example). These structures can be produced efficiently, rapidly, and in sufficient quantities for use as stand-alone anti-sepsis molecules. Thus, in some embodiments, bacteria utilized in the methods of the disclosure act as factories to supersede the extensive multidisciplinary efforts normally used to synthesize desired molecules.

In some embodiments, the anti-sepsis lipid A (ASLA) based therapeutics are produced by Gram-negative bacterial strains. The Gram-negative bacteria may be of any kind, including from *Acetobacter, Borrelia, Bordetella, Burkholderia, Campylobacter, Chlamydia, Enterobacter, Eshcerichia, Fusobacterium, Helicobacter, hemophilus, Klebsiella, Legionella, Leptospiria, Neisseria, Nitrobacter, Proteus, Pseudomonas, Ricketsia, Salmonella, Serratia, Shigella, Thiobacter, Treponema, Vibrio*, or *Yersinia*. In specific embodiments, one or more of the following bacteria are utilized to produce the anti-sepsis lipid A (ASLA) based therapeutic: Acetic acid bacteria, *Acinetobacter baumannii, Agrobacterium tumefaciens, Anaerobiospirillum, Arcobacter, Arcobacter skirrowii, Armatimonas rosea, Bacteroides, Bacteroides fragilis, Bacteroides ruber, Bartonella taylorii, Bdellovibrio, Brachyspira, Cardiobacterium hominis, Chthonomonas calidirosea, Coxiella burnetii, Cyanobacteria, Cytophaga, Dialister, Enterobacter, Enterobacter cloacae, Enterobacter cowanii, Enterobacteriaceae, Enterobacteriales, Escherichia, Escherichia coli, Escherichia fergusonii, Fimbriimonas ginsengisoli, Fusobacterium necrophorum, Fusobacterium nucleatum, Fusobacterium polymorphum, Haemophilus haemolyticus, Haemophilus influenzae, Helicobacter, Helicobacter pylor, Klebsiella pneumoniae, Legionella, Legionella pneumophila, Leptotrichia buccalis, Escherichia coli, Luteimonas aestuarii, Luteimonas aquatica, Luteimonas composti, Luteimonas lutimaris, Luteimonas marina, Luteimonas mephitis, Luteimonas vadosa, Megamonas, Megasphaera, Meiothermus, Methylobacterium fujisawaense, Morax-Axenfeld diplobacilli, Moraxella, Moraxella bovis, Moraxella osloensis, Morganella morganii, Negativicutes, Neisseria cinerea, Neisseria gonorrhoeae, Neisseria meningitidis, Neisseria sicca, Nitrosomonas eutropha, Nitrosomonas halophila, Nitrosomonas oligotropha, Pectinatus, Pelosinus*, Pontiac fever, *Propionispora, Proteobacteria, Proteus mirabilis, Proteus penneri, Pseudomonas, Pseudomonas aeruginosa, Pseudomonas, Pseudomonas luteola, Pseudoxanthomonas broegbernensis, Pseudoxanthomonas japonensis, Rickettsia rickettsii, Salmonella, Salmonella bongori, Salmonella enterica, Salmonella enterica* subsp. *enterica, Selenomonadales, Serratia marcescens, Shigella, Sorangium cellulosum, Sphaerotilus, Spirochaeta, Spirochaetaceae, Sporomusa, Stenotrophomonas, Stenotrophomonas nitritireducens, Thermotoga neapolitana, Trimeric autotransporter adhesin, Vampirococcus, Verminephrobacter, Vibrio adaptatus, Vibrio azasii, Vibrio campbellii, Vibrio cholerae, Vitreoscilla, Wolbachia*, or *Zymophilus.*

In some embodiments of methods of generating an anti-sepsis lipid A (ASLA) based therapeutic, the bacterial strain used is *Yersinia pestis, Pseudomonas*, an Archaebacteria or an extremophile. In specific embodiments, the one or more non-endogenous lipid A biosynthesis enzymes is from *Yersinia pestis, Pseudomonas aeruginosa, Acinetobacter baumannii, Francisella novicida, E. coli, Bordetella* subspecies, *Helicobacter pylori, Leptospira interrogans* or *Salmonella typhimurium.*

In some embodiments, the anti-sepsis lipid A (ASLA) based therapeutics are produced by Gram-negative microorganism *Yersinia pestis*. In some embodiments, the Gram-negative microorganism is *Yersinia pestis* KIM6 strain.

In some embodiments, the molecules can be created by heterologous expression from plasmids or the chromosome of single or combinations of acyltransferase, deacylases, phosphatase and/or glycosyltransferases enzymes or through mutation of global regulatory genes required for regulating lipid A biosynthesis in a microorganism, such as an attenuated (BSL2-safe) hypo-acylated *Y. pestis*. This exemplary strain when grown at mammalian temperatures produces a bisphosphorylated tetra-acylated structure that does not elicit proinflammatory responses in a variety of in vitro and in vivo assays. In some embodiments, the enzymes can be used from a wide variety of bacterial backgrounds, as shown in Table 1. These enzymes have specificities for fatty acid chain length additions either on the diglucosamine backbone of lipid A or acyl-oxy-acyl on these primary fatty acids, the removal of specific fatty acids or phosphate residues from the diglucosamine backbone, or more global changes due to directed mutations in either the sensor kinase or response regulator of various two-component regulatory systems, for example. Individually modified, rationally-designed lipid A structures can be characterized using a variety of mass spectrometry and gas chromatography-based methodologies (as examples) to confirm the overall structure of the lipid A in the disclosed strains to generate using bacterial enzymatic combinatorial chemistries (BECC).

In some embodiments, there is custom synthesis of LOS/lipid A molecules using heterologous expression of bacterial enzymes required for LPS biosynthesis (acyltransferases, glycosyltransferases, phosphatases, and/or kinases, for example), and through manipulation of global regulatory or biosynthesis genes in an attenuated *Yersinia pestis* background (as an example of a background). A variety of mass spectrometry and gas chromatography-based methodologies can be used to verify that the correct lipid A modifications have been synthesized.

In some embodiments, anti-sepsis lipid A (ASLA) based therapeutics can be produced using any of the three BECC *Yersinia pestis* strains when grown at 37° C., mammalian host temperature as shown in Table 1.

Figure 25:
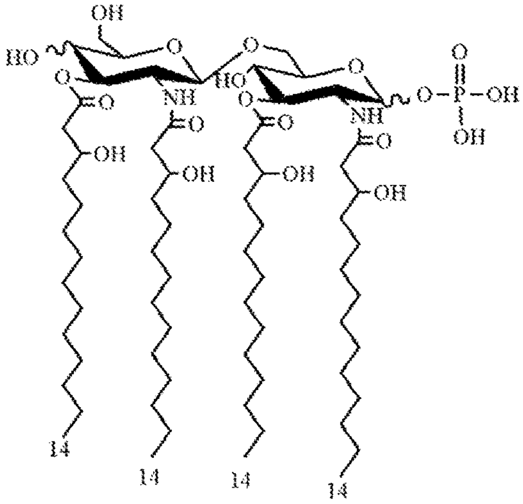
FIG. 25 demonstrates the structure of an exemplary LPS molecule generated by methods of the disclosure using an engineered *Y. pestis*.
Figure 26:
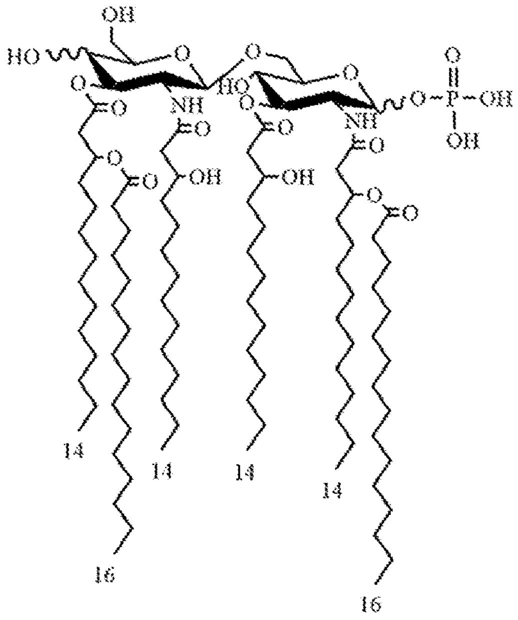
FIG. 26 demonstrates the structure of an exemplary LPS molecule generated by methods of the disclosure using an engineered *Y. pestis*.
Figure 27A:
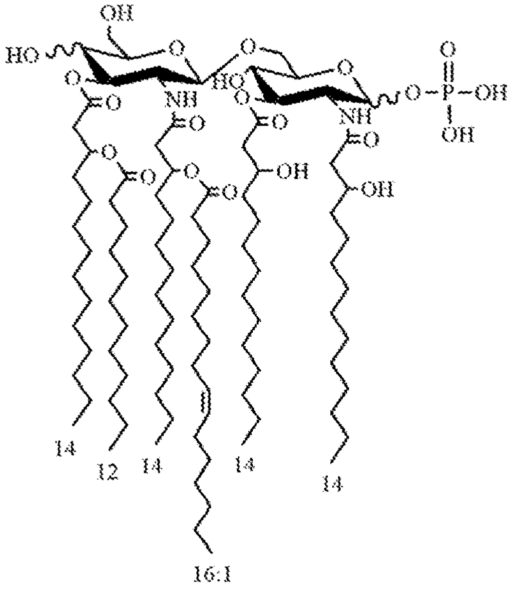
FIGS. 27A-B demonstrate the structures of exemplary LPS molecules generated by methods of the disclosure using an engineered *Y. pestis*.
Figure 27B:
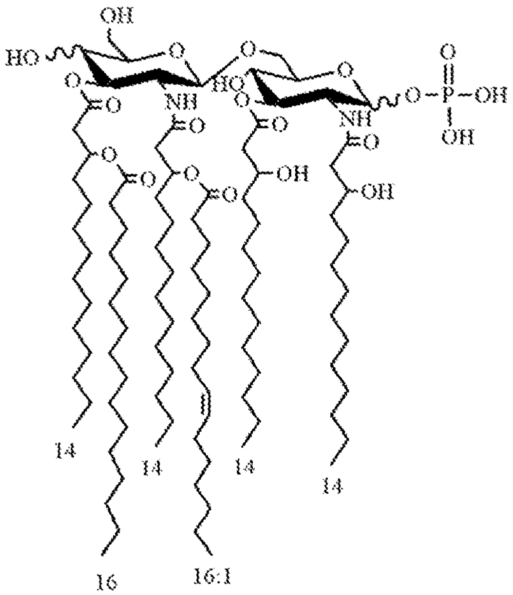
Figure 28A:
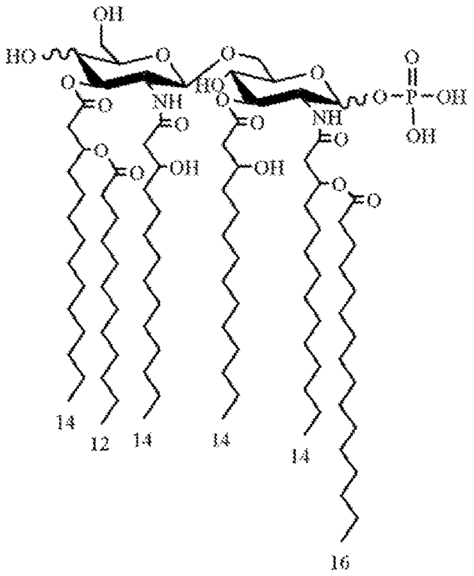
FIGS. 28A-D demonstrate the structures of exemplary LPS molecules generated by methods of the disclosure using an engineered *Y. pestis*.
Figure 28B:
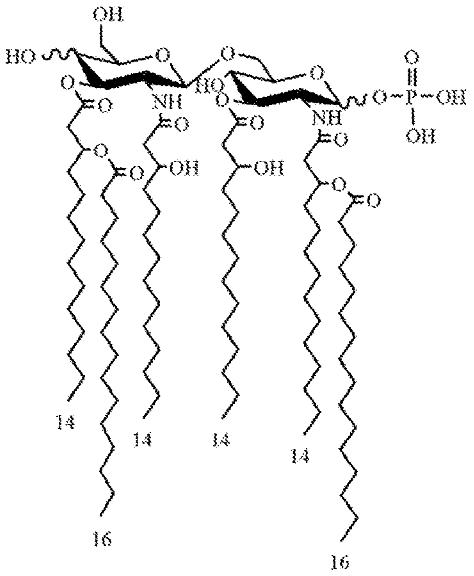
Figure 28C:
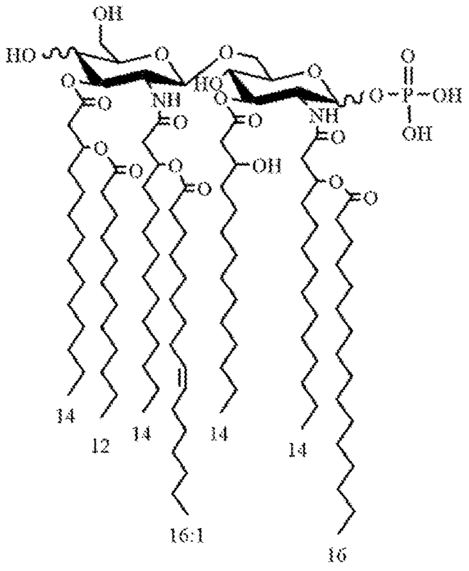
Figure 28D:
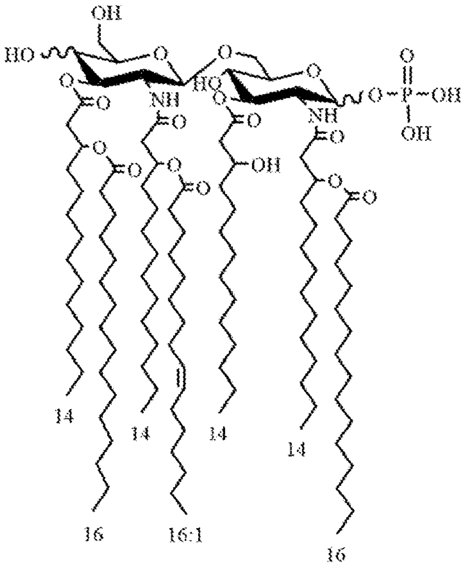
Figure 30:
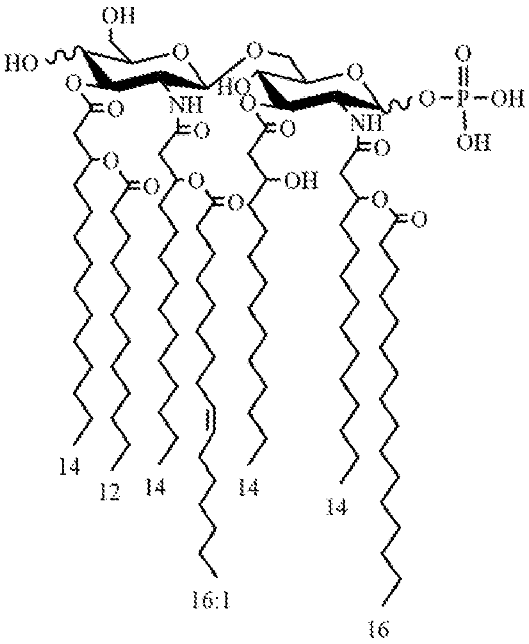
FIG. 30 demonstrates the structure of an exemplary LPS molecule generated by methods of the disclosure using an engineered *Y. pestis*.
Figure 31:
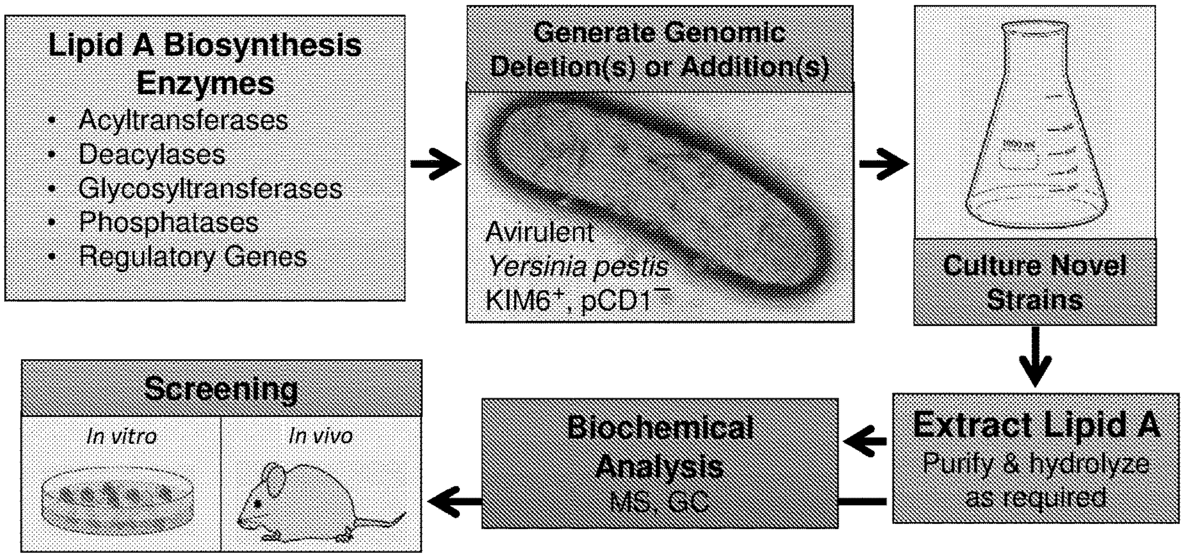
FIG. 31 shows a process for generating anti-sepsis molecules.

Construction of additional rationally-designed LOS/lipid A structures with modified lipid A structures using BECC can be achieved. In some embodiments, the invention provides methods of making attenuated *Yersinia pestis* (Yp) strains that produce modified LOS/lipid A molecules that are subsequently screened for anti-sepsis activity. Useful to the design of BECC are well-characterized enzymes sourced from a variety of bacterial species (FIG. 25 provides a list of cloned enzymes). The modifying enzymes can be expressed in an attenuated Yp background, such as KIM6 or KIM10, to engineer unique lipid A structures. Bacterial conjugation, electroporation, or bacterial mating may be utilized to introduce genes from an enzyme library into the Yp KIM6 parent chromosome or via exchange of expression plasmids (Jones et al., 2010; Rebeil et al., 2004; Donenberg and Kaper, 1991). An example of a scheme of use for the individual modifying genes is based on known structure/function interaction of specific modifications and the host innate immune receptor (TLR4) complex and may be prioritized as follows: 1) mutations in global regulators of lipid A modifications, 2) altering the level of fatty acid content through the addition or deletion of acyltransferases and/or deacylases, 3) expression of phosphatase to specifically remove one of the terminal phosphates on the lipid A backbone, and 4) expression of glycosyltransferases that will add specific sugar residues to the terminal phosphate residues. Strains may be vetted by a combination of MALDI-TOF MS for initial lipid A structural confirmation followed by higher order MS (ESI) to provide intimate structural detail and molecular design validation. One can use gas chromatography (GC) to quantify the percentage of total fatty acids of each respective modified lipid A structure, providing further verification that the correct strains have been generated and that they are both productive and accurate.

TABLE 1

BECC MODIFIED STRAINS OF YP

| Strains | Strain Description |
|---|---|
| 1. Wild-type Yp KIM6 | WT KIM6 (exempt select agent strain of Yp; lacks pigmentation locus and pCD1 plasmid; CDC BSL-2 classification) |
| 2. KIM6-pagP+ | KIM6 with a repaired pagP gene (adds C16 fatty acid to lipid A) |
| 3. ΔphoP-KIM6 | KIM6 with a deleted phoP gene, which is a member of a 2 component sensor kinase signaling system (a transcriptional regulator) |
| 4. ΔphoP - pagP+ | KIM6 with a deleted phoP gene which is a member of a 2 component sensor kinase signaling system (a transcriptional regulator) and a repaired pagP activating gene which adds C16 fatty acids to lipid A |

Modifications in these strains have been confirmed by MS and GC analysis (data not shown).

Analysis of LOS and lipid A isolated from BECC constructed strains is provided herein. For initial screening, one can use two small-scale LOS extraction protocols that require small overnight cultures (~5 mls). These methods include a phenol-based (Yi and Hackett, 2000; Westphal and Juan, 1965) and an ammonium hydroxide/isobutyric acid-based (El Hamidi et al., 2005) protocol, which are repeatable and robust extraction techniques, standard methods in the Ernst laboratory. After extraction, lipid A will be liberated from these LOS preparations using gentle hydrolysis, which preserves structural elements (e.g., phosphate groups and attached carbohydrate moieties) that are sensitive to harsh acid treatment (Caroff et al., 1988) One can use a variety of mass spectrometric-based techniques, such as MALDI-TOF and ESI routinely used in the art to characterize the base structure of the lipid A in both the negative and positive-ion mode (Ernst et al., 2006). Large-scale LOS preparations can be extracted using a hot phenol/water extraction method (Ernst et al., 2007; Ernst et al., 2006; West et al., 1997; Hajjar et al., 2006). Subsequently, LOS can be treated to ensure purity from contaminating nucleic acids and proteins (Fischer et al., 1983) and converted to lipid A by mild hydrolysis. LOS samples can be extracted to remove contaminating phospholipids (Folch et al., 1957) and TLR2-agonist proteins (Hirschfeld et al., 2000) thus generating preparations suitable for structural analysis and proinflammatory studies discussed proposed below. LOS/lipid A fatty acid content can be measured by gas chromatography (GC) after acid hydrolysis, methylation, and hexane extraction (Guo et al., 1997; Somerville et al., 1996). The resultant $MS^n$ and GC data can be used to define the exact structure of individual molecules present in the isolated lipid A from the WT and BECC constructed strain.

In some embodiments, anti-sepsis molecules of the invention can be prepared using the following genetically engineered strains as shown below:

TABLE 2

| Strain # | Strain/Plasmid Name | Main Ion Species (37° C./ 26° C.) | Genus species subspecies | Chemical Structure |
|---|---|---|---|---|
| T-BE-44 | *Y. pestis* KIM6$^+$ΔphoP | 1403.8/ 1822.2 | *Yersinia pestis* Kim6 Avir | Structure A/ Structure C |
| T-BE-438 | *Y. pestis* KIM6 ΔmsbB pagP+ | 1880.3/ 1878.5 | *Yersinia pestis* Kim6 Avir | Structure B/ Structure F |
| T-BE-440 | *Y. pestis* KIM6 ΔmsbB ΔIpxP pagP+ | 1880.3/ 1880.3 | *Yersinia pestis* Kim6 Avir | Structure B/ Structure B |
| T-BE-467 | *Y. pestis* KIM6 IpxE | 1323.8/ 1742.3 | *Yersinia pestis* Avir Kim6 | Structure H/ Structure J |
| T-BE-468 | *Y. pestis* KIM6 IpxF | 1323.8/ 1742.3 | *Yersinia pestis* Avir Kim6 | Structure L/ Structure N |
| T-BE-469 | *Y. pestis* KIM6 pagP+ IpxE | 1800.3/ 1744.3 | *Yersinia pestis* Avir Kim6 | Structure I/ Structure K |
| T-BE-470 | *Y. pestis* KIM6 pagP+ IpxF | 1800.3/ 1744.3 | *Yersinia pestis* Avir Kim6 | Structure M/ Structure O |

FIGS. 15 and 16 provide embodiments describing descriptions of individual strains generated, structures of the resultant anti-sepsis lipid A (ASLA) based therapeutics, and mass of the resultant anti-sepsis lipid A (ASLA) based therapeutics when the *Y. pestis* strain was grown at 26° C. or 37° C. Shown in FIGS. 17-28 and 30 are exemplary anti-sepsis lipid A (ASLA) based therapeutics generated using genetic engineering methods of the disclosure using *Y. pestis*. FIG. 29 further provides a description and heterologous sources of LOS/Lipid A modifying enzymes for BECC, illustrating examples of modifying enzymes that may be used to generate *Y. pestis* or other strains with modified LOS.

In some embodiments, the Gram-negative microorganism is engineered to express one or more non-endogenous lipid A biosynthetic enzymes, inactivate/delete one or more endogenous lipid A biosynthetic enzymes, modify one or more endogenous lipid A biosynthetic enzymes, and/or increase or decrease expression of one or more endogenous lipid A biosynthetic enzymes. In some embodiments, the lipid A biosynthetic enzyme is from one or more of *Yersinia pestis, Pseudomonas aeruginosa, Acinetobacter baumannii, Francisella novicida, E. coli, Bordetella* subspecies, *Helicobacter pylori, Leptospira interrogans* or *Salmonella typhimurium*. In some embodiments, the lipid A-modifying enzyme can include phoP, lpxP, msbB, lpxE, pagP, and/or lpxF.

In one embodiment, the invention provides a method of making a compound (ASLA 470) of the formula

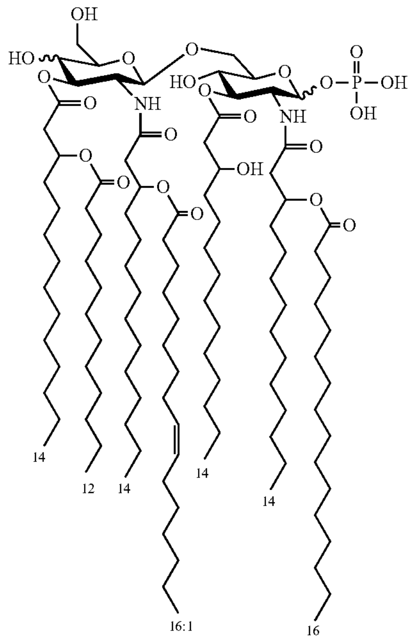

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to express LpxF from *Francisella novicida* and have a repaired *Y. pestis* pagP.

In one embodiment, the invention provides a method of making a compound (ASLA 468) of the formula

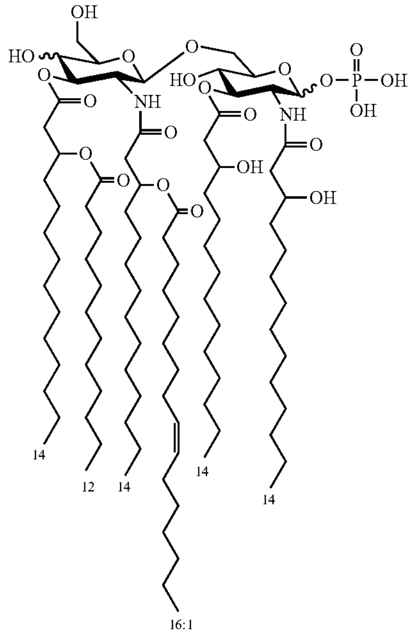

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to express LpxF from *Francisella novicida* and have a repaired *Y. pestis* pagP.

In one embodiment, the invention provides a method of making a compound (ASLA 468; C16 version) of the formula

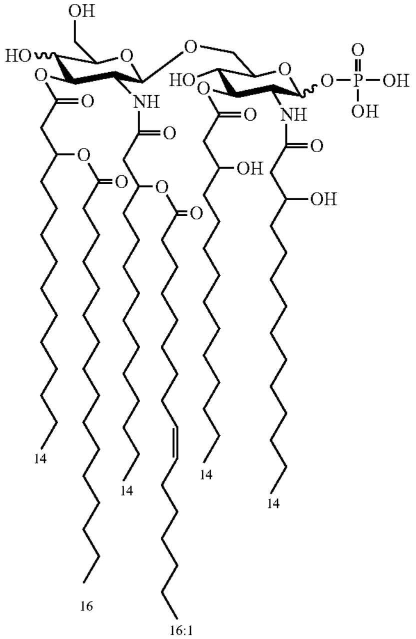

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to express LpxF from *Francisella novicida* and have a repaired *Y. pestis* pagP.

In one embodiment, the invention provides a method of making a compound (ASLA 469; Structure I) of the formula

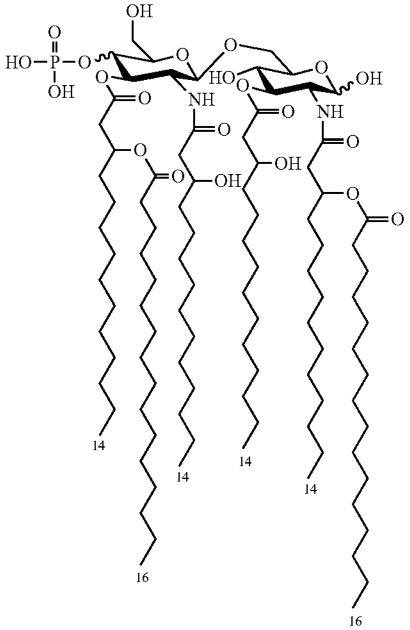

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* KIM6 is cultured between 30-39° C., e.g., at about 37° C. and has been genetically engineered to express LpxE from *Francisella novicida* and have a repaired *Y. pestis* pagP.

In one embodiment, the invention provides a method of making a compound (ASLA 467; Structure J) of the formula

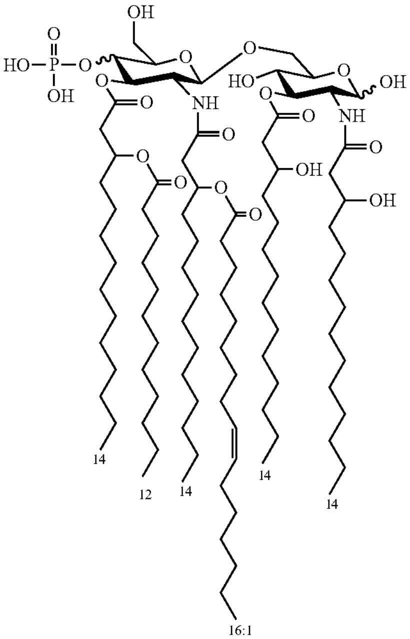

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* KIM6 is cultured between 12-28° C., e.g., at about 26° C. and has been genetically engineered to express LpxE from *Francisella novicida.*

In one embodiment, the invention provides a method of making a compound (Structure A) of the formula

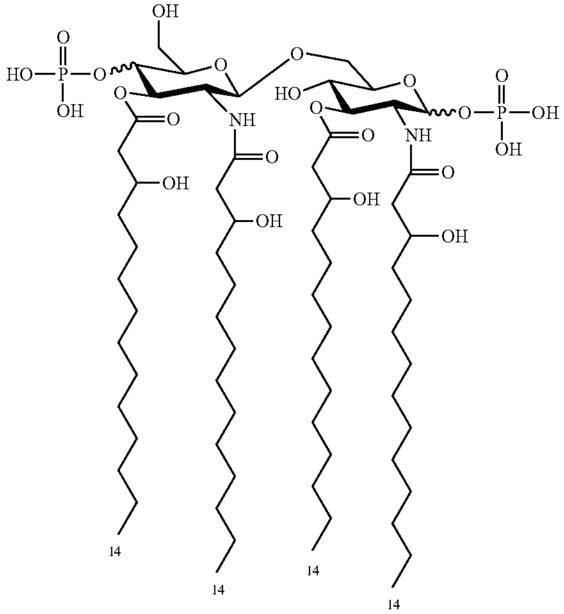

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 30-39° C., e.g., at about 37° C. and has been genetically engineered to have a deletion in lpxP.

In one embodiment, the invention provides a method of making a compound (Structure B) of the formula

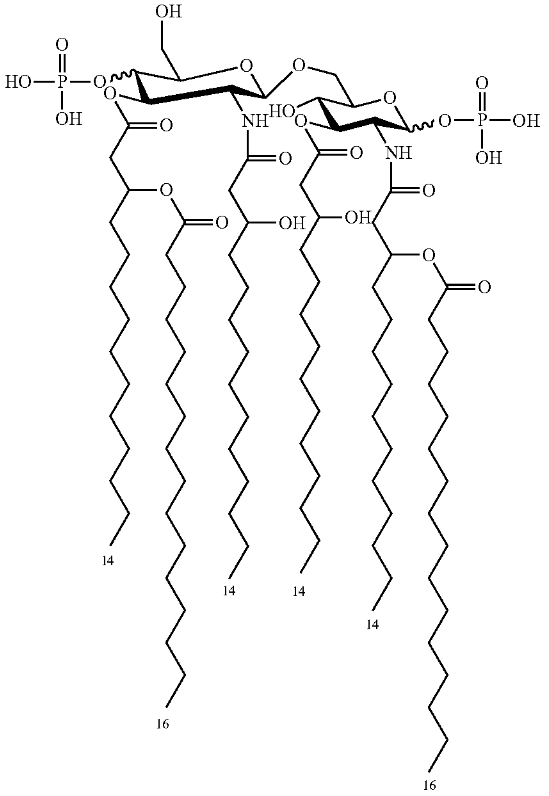

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 30-39° C., e.g., at about 37° C. and has been genetically engineered to have a deletion in lpxP and have a repaired *Y. pestis* pagP.

In one embodiment, the invention provides a method of making a compound (Structure C1) of the formula

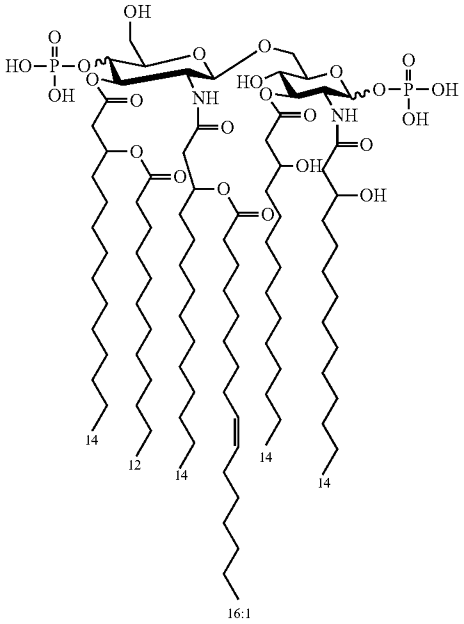

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to have a deletion in phoP and have a repaired *Y. pestis* pagP.

In one embodiment, the invention provides a method of making a compound (Structure C2) of the formula

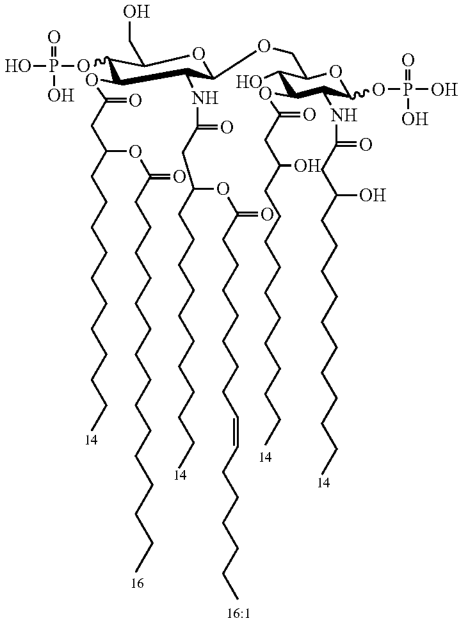

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to have a deletion in phoP and have a repaired *Y. pestis* pagP.

In one embodiment, the invention provides a method of making a compound (Structure D1) of the formula

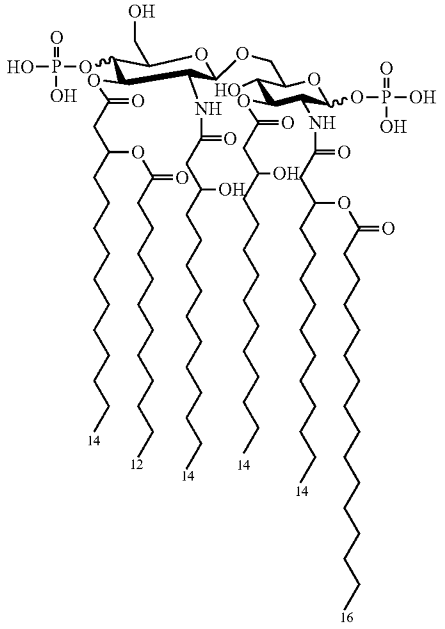

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to have a deletion in phoP and have a repaired *Y. pestis* pagP.

In one embodiment, the invention provides a method of making a compound (Structure D2) of the formula

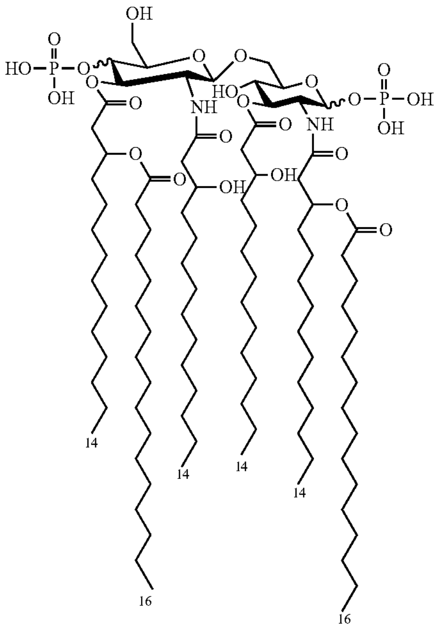

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to have a deletion in phoP and have a repaired *Y. pestis* pagP.

In one embodiment, the invention provides a method of making a compound (Structure D3) of the formula

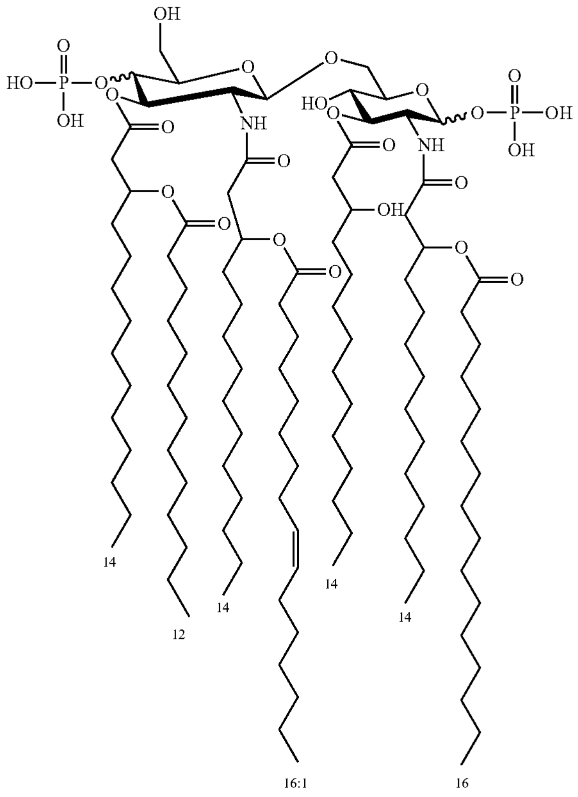

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to have a deletion in phoP and have a repaired *Y. pestis* pagP.

In one embodiment, the invention provides a method of making a compound (Structure D4) of the formula

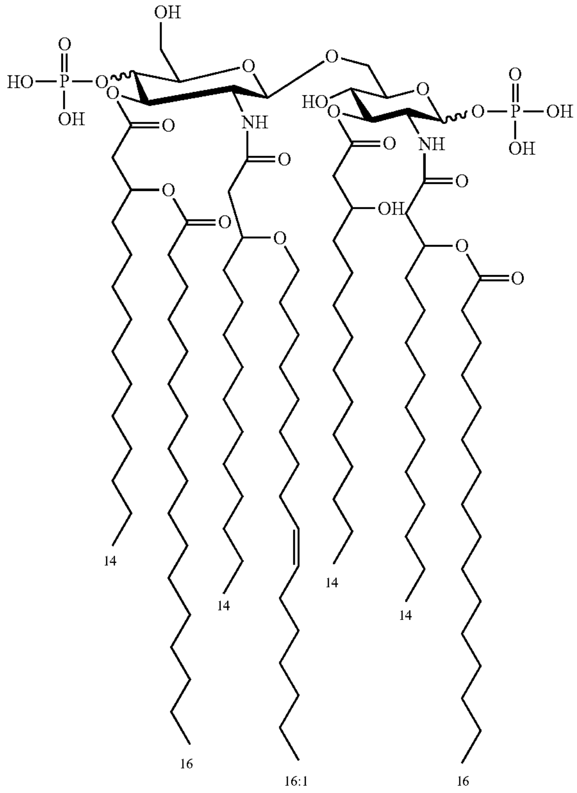

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to have a deletion in phoP and have a repaired *Y. pestis* pagP.

In one embodiment, the invention provides a method of making a compound (Structure E) of the formula

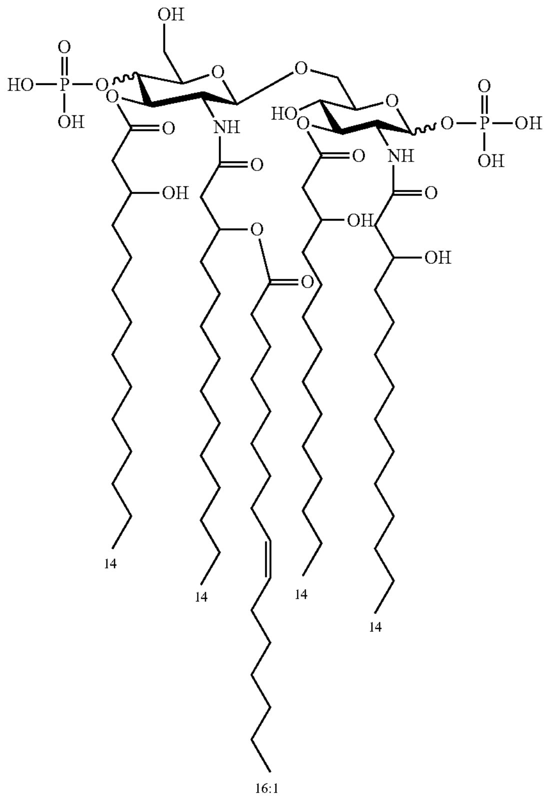

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to have a deletion in msbB and have a repaired *Y. pestis* pagP.

In one embodiment, the invention provides a method of making a compound (Structure F) of the formula

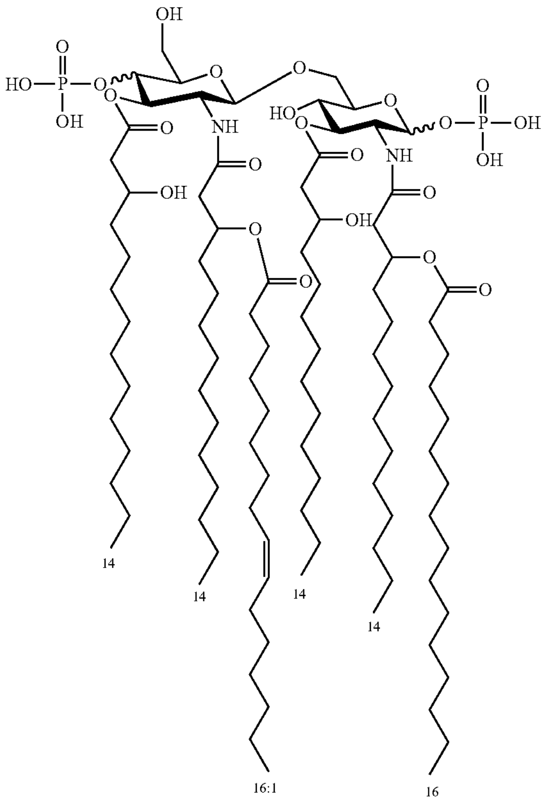

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to have a deletion in msbB and have a repaired *Y. pestis* pagP.

In one embodiment, the invention provides a method of making a compound (Structure G) of the formula

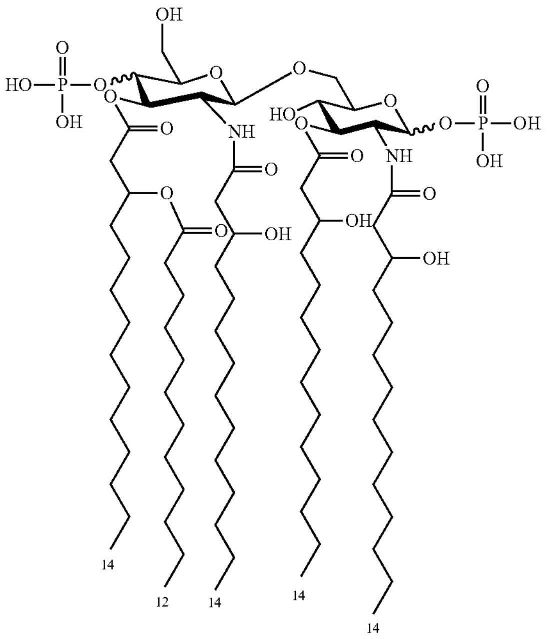

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 30-39° C., e.g., at about 37° C. and has been genetically engineered to have a deletion in lpxP.

In one embodiment, the invention provides a method of making a compound (Structure H) of the formula

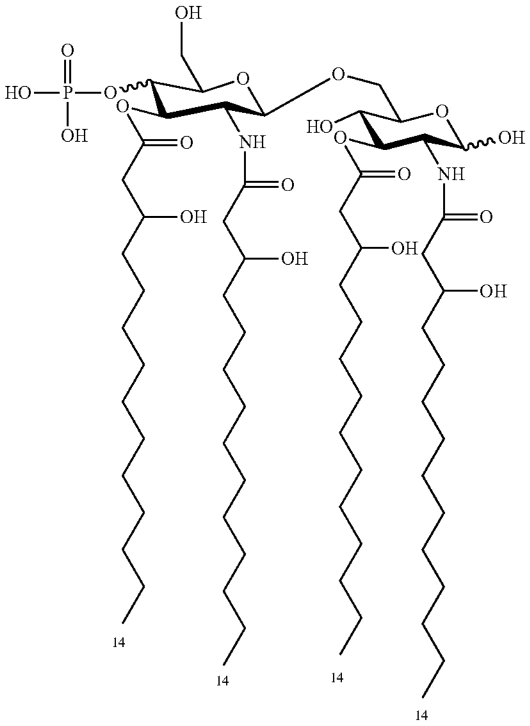

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* KIM6 is cultured between 30-39° C., e.g., at about 37° C. and has been genetically engineered to express lpxE from *Francisella novicida.*

In one embodiment, the invention provides a method of making a compound (Structure K1) of the formula

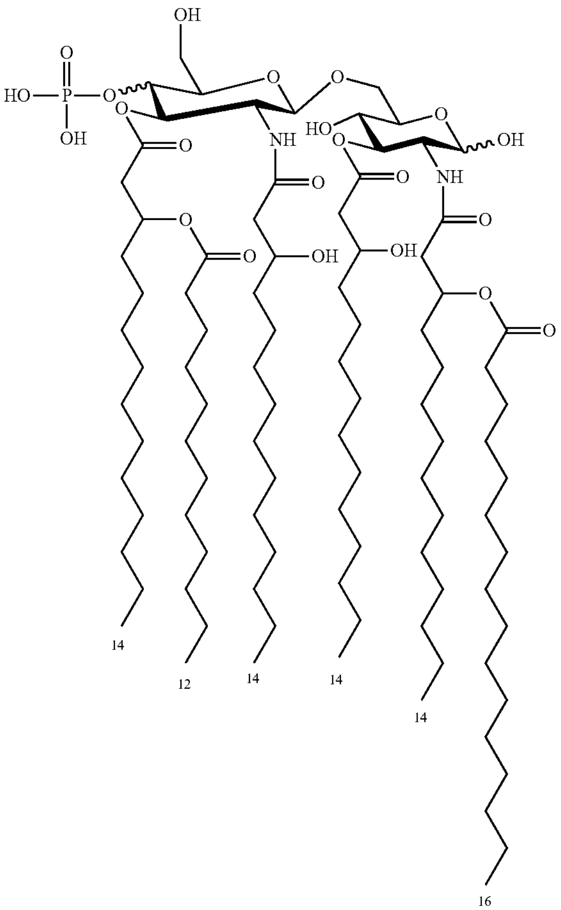

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* KIM6 is cultured at between 12-28° C., e.g., at about 26° C. and has been genetically engineered to express lpxE from *Francisella novicida* and have a repaired *Y. pestis* pagP.

In one embodiment, the invention provides a method of making a compound (Structure K2) of the formula

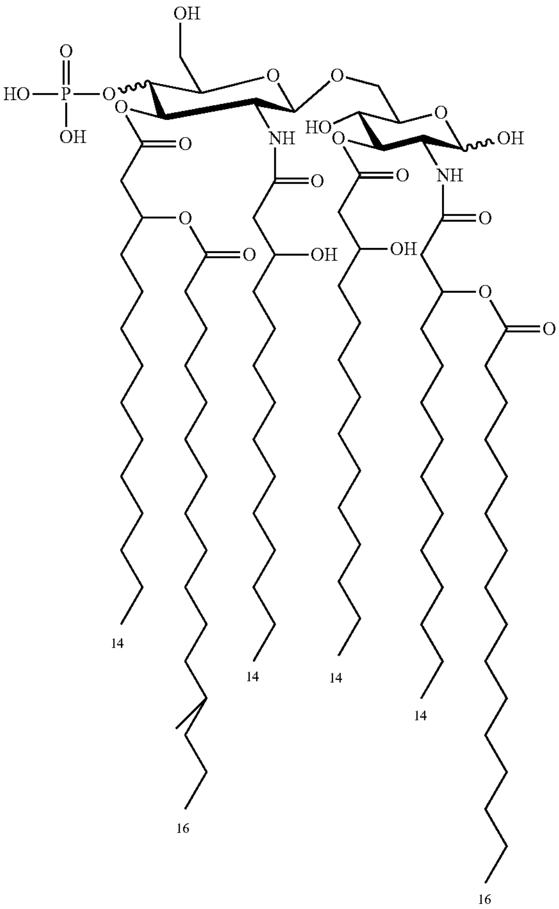

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* KIM6 is cultured at between 12-28° C., e.g., at about 26° C. and has been genetically engineered to express lpxE from *Francisella novicida* and have a repaired *Y. pestis* pagP.

In one embodiment, the invention provides a method of making a compound (Structure K3) of the formula

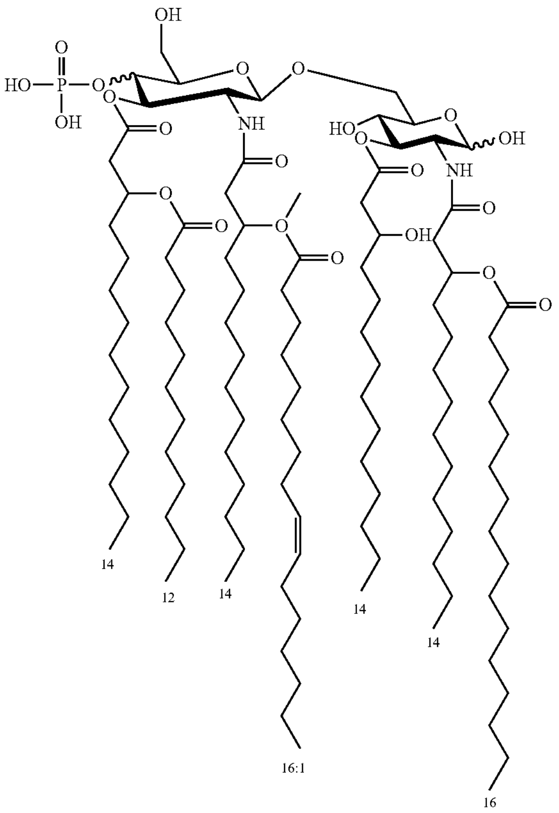

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* KIM6 is cultured at between 12-28° C., e.g., at about 26° C. and has been genetically engineered to express lpxE from *Francisella novicida* and have a repaired *Y. pestis* pagP.

In one embodiment, the invention provides a method of making a compound (Structure K4) of the formula

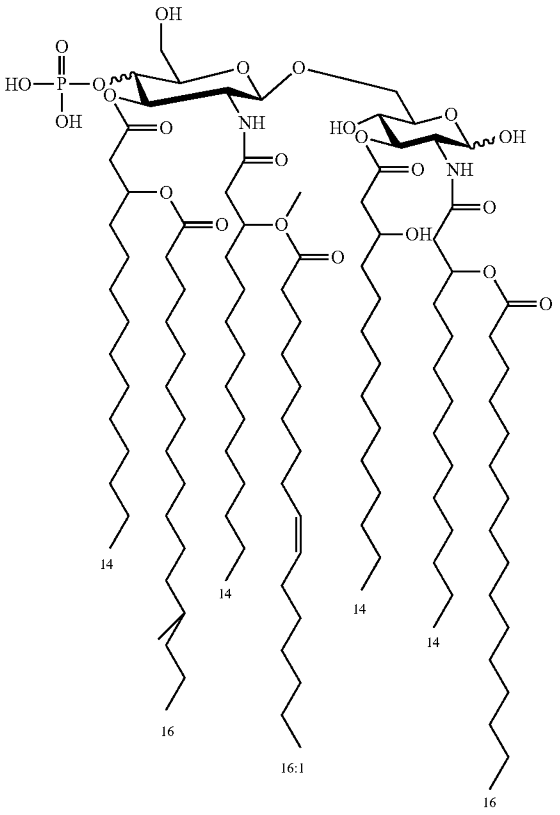

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* KIM6 is cultured between 12-28° C., e.g., at about 26° C. and has been genetically engineered to express lpxE from *Francisella novicida* and have a repaired *Y. pestis* pagP.

In one embodiment, the invention provides a method of making a compound (Structure L) of the formula

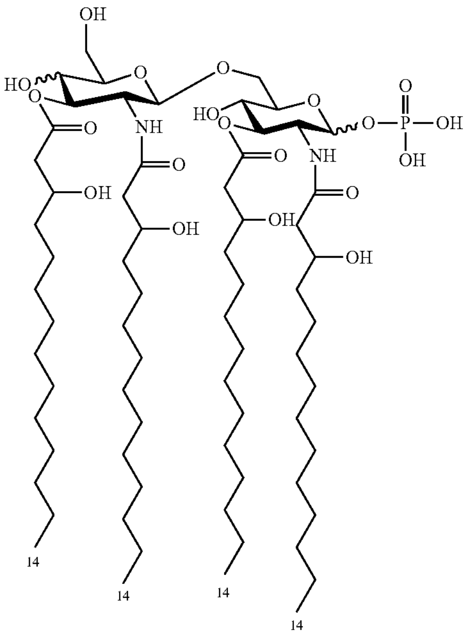

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 30-39° C., e.g., at about 37° C. and has been genetically engineered to express lpxF from *Francisella novicida.*

In one embodiment, the invention provides a method of making a compound (Structure M) of the formula

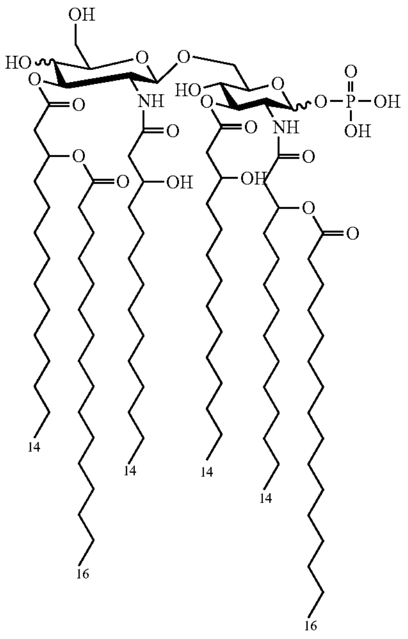

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 30-39° C., e.g., at about 37° C. and has been genetically engineered to express lpxF from *Francisella novicida* and have a repaired *Y. pestis* pagP.

In one embodiment, the invention provides a method of making a compound (Structure O1) of the formula

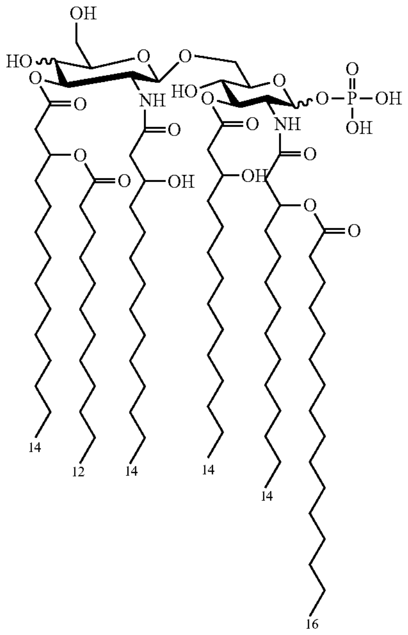

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to delete phoP and have a repaired *Y. pestis* pagP.

In one embodiment, the invention provides a method of making a compound (Structure O2) of the formula

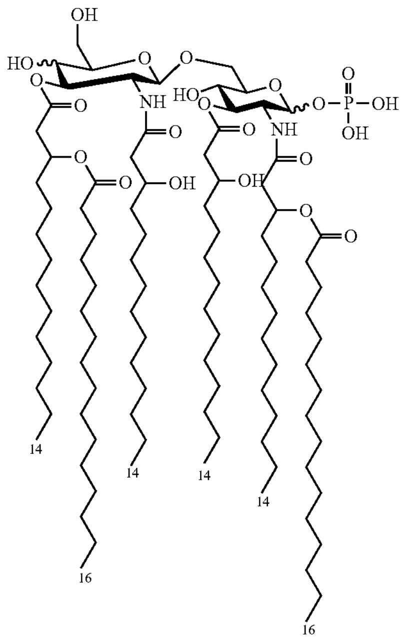

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to delete phoP and have a repaired *Y. pestis* pagP.

In one embodiment, the invention provides a method of making a compound (Structure O3) of the formula

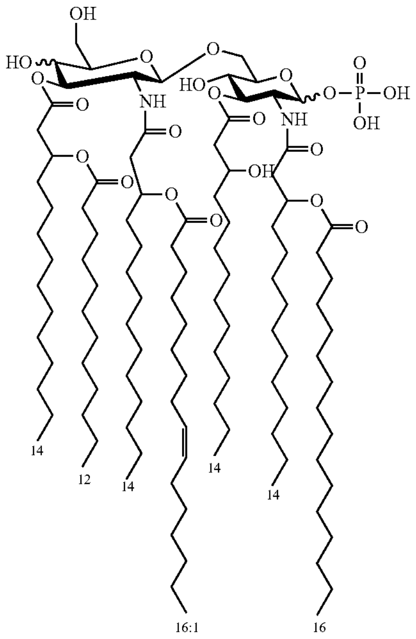

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to express lpxF from *Francisella novicida*, delete phoP and have a repaired *Y. pestis* pagP.

In one embodiment, the invention provides a method of making a compound (Structure O4) of the formula

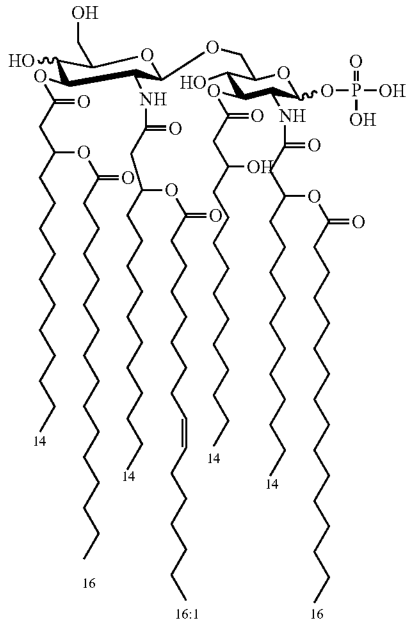

wherein the method comprises genetically engineering a Gram-negative microorganism such as *Y. pestis* to produce the anti-sepsis lipid A (ASLA) based therapeutic, and isolating the anti-sepsis lipid A (ASLA) based therapeutic from the microorganism. In some embodiments, the *Y. pestis* is cultured between 12-28° C., e.g., at about 26° C. and has been genetically engineered to express lpxF from *Francisella novicida*, delete phoP and have a repaired *Y. pestis* pagP.

Upon production of the anti-sepsis lipid A (ASLA) based therapeutics in a selected bacterial strain, the anti-sepsis lipid A (ASLA) based therapeutics can be obtained from the bacteria. The mimetic molecules may be obtained by any suitable method, but in specific embodiments they are chemically extracted using standard LOS extraction protocols. In some embodiments, initially multiple types of LOS extraction procedures are employed to obtain LOS from the bacteria, and extraction procedures may be performed more than once. In some embodiments, the extraction procedures are phenol-based, magnesium-precipitation-based, ammonium hydroxide/isobutyric acid-based, chloroform-methanol-based, detergent-based, and so forth.

Once the LOS preparation is obtained from the bacteria, the lipid A fraction can be liberated using gentle hydrolysis to protect sensitive structural elements.

In some embodiments, lipid A or its mimetics may be isolated as follows. Lipid A was isolated after hydrolysis in 1% SDS at pH 4.5. Briefly, 500 μl of 1% SDS in 10 mM Na-acetate (pH 4.5) was added to a lyophilized sample. Samples were incubated at 100° C. for 1 h, frozen, and lyophilized. The dried pellets were resuspended in 100 μl of water and 1 ml of acidified ethanol (100 μl 4 N HCl in 20 ml 95% ethanol). Samples were centrifuged at 5,000 rpm for 5 min. The lipid A pellet was further washed (three times) in 1 ml of 95% ethanol. The entire series of washes was repeated twice. Samples were resuspended in 500 μl of water, frozen on dry ice, and lyophilized. Lipid A was used for matrix-assisted laser desorption ionization (MALDI) mass spectrometry analysis.

Following extraction of the desired anti-sepsis lipid A (ASLA) based therapeutic, the mimetic can be analyzed for structure and/or function. In certain cases, the structure is analyzed prior to the function, whereas in other cases the function is analyzed prior to the structure. The analysis may be on a small scale with only a few mimetics being analyzed at substantially the same time or on a large scale with many mimetics being analyzed at substantially the same time.

In some embodiments, the structure can be analyzed by routine methods in the art, including using one or more procedures for the analysis. In particular embodiments, mass spectrometry, gas chromatography, or both are utilized for analysis of structure. For mass spectrometry embodiments, matrix-assisted laser desorption/ionization/time-of-flight mass spectrometry (MALDI-TOF) and electrospray ionization (ESI) are utilized, including in both the negative and positive-ion mode. Other steps to analyze LOS/lipid A fatty acid content can include acid hydrolysis, methylation, and hexane extraction.

In specific embodiments, one or more structures produced by methods of the disclosure are analyzed as follows.

Lipid A can be analyzed by ESI in the negative mode of an LTQ-FT linear ion trap Fourier transform ion cyclotron resonance mass spectrometer (Thermo Fisher). Samples can be diluted to ~0.3-1.0 mg/ml in chloroform/methanol (1:1) and infused at a rate of 0.5-1.0 ul/min via a fused silica capillary (75 um i.d./360 um o.d.) with an ~15 um spray tip (New Objective). Instrument calibration and tuning parameters can be optimized by using a solution of Ultramark 1621 (Lancaster Pharmaceuticals). For experiment acquired in the ICR cell, resolution can be set at 100K and ion populations can be held constant by automatic gain control at $1.0\times10^6$ and $5.0\times10^5$ for MS and MS/MS, respectively. For tandem mass spectra, the precursor ion selection window can be set to 4-8 DS and the collision energy was set to 30% on the instrument scale. The CID $MS^n$ analysis in the linear ion trap can be acquired with an ion population of $1.0\times10^4$ maximum fill time of 200 ms. The subsequent $MS^3$ and $MS^4$ had an isolation window of 2 Da with a collision energy of 25%. All spectra can be acquired over a period of 1-2 min and averaged. Typically, MS and $MS^2$ events can be mass analyzed in the ICR cell, and the $MS^3$ and $MS^4$ can be mass analyzed in the LTQ. Infrared multiphoton dissociation (IRMPD) $MS^2$ events can be acquired in the ICR cell using similar detection parameters to those described above. Precursor ions can be irradiated by IR photons produced by a $CO_2$ laser [Synrad firestar Series V20), Model FSV20SFB; 75 W (10.2-10.8 um)] with pulse durations of 20-100 ms and pulse power of 20-80%. Data can be acquired and processed with Xcaliber (version 1.4; Thermo Fisher) using seven-point Gaussian smoothing. On-line liquid chromatography ESI tandem MS experiments can be performed by interfacing a custom-fabricated microcolumn (fused-silica capillary) packed with silica to the LTQ-FTESI source.

Lipid A can be analyzed by ESI in the negative ion mode on a Sciex API III tandem quadrupole mass spectrometer (Perkin Elmer). Samples can be diluted to ~0.3-1.0 mg/ml in chloroform/methanol (1:1) and infused at a rate of 0.5-1.0 ul/min via a fused silica capillary (i.d. 100 um) by using a syringe pump (Harvard Apparatus Model 11). The instrument can be operated with the following settings: needle voltage, −4300 V; counter electrode, −650 V, nebulizer gas pressure, 20 psi; curtain gas pressure, 10 psi; declustering potential, −35 V; collision cell entrance potential, −10 V; collision cell exit potential, −15V; and collision gas, argon. Tandem MS data can be acquired in both product and precursor ion scan modes.

Lipid A structures can be assessed by negative-ion MALDI-TOF MS. Lyophilized lipid A can be extracted in chloroform/methanol and then 1 μl was mixed with 1 μl of Norharmane MALDI matrix. All MALDI-TOF experiments can be performed using a Bruker Autoflex Speed MALDI-TOF mass spectrometer (Bruker Daltonics, Billerica, Mass.). Each spectrum can be an average of 300 shots. ES tuning mix (Aligent, Palo Alto, Calif.) can be used for calibration.

LPS fatty acids can be converted to fatty acid methyl esters and analyzed by gas chromatography (GC). Briefly, 10 mg of lyophilized bacterial cell pellet can be incubated at 70° C. for 1 hour in 500 μl of 90% phenol and 500 μl of water. Samples can be then cooled on ice for 5 minutes and centrifuged at 10,000 rpm for 10 minutes. The aqueous layer can be collected and 500 μl of water was added to the lower (organic) layer and incubated again. This process can be repeated twice more and all aqueous layers were pooled. Two ml of ethyl ether can be added to the harvested aqueous layers, this mixture can be then vortexed and centrifuged at 3,000 rpm for 5 minutes. The lower (organic) phase can be then collected and 2 ml of ether can be added back remaining aqueous phase. This process can be carried out twice more. The collected organic layer can be then frozen and lyophilized overnight. LPS fatty acids can be converted to fatty methyl esters, in the presence of 10 μg pentadeconic acid (Sigma, St Louis, Mo.) as an internal standard, with 2 M methanolic HCl (Alltech, Lexington, Ky.) at 90° C. for 18 hours.

Screening Assays for Anti-Sepsis Lipid A (ASLA) Based Therapeutics

In another embodiment, the invention provides a method of screening a molecule for anti-sepsis activity, comprising i) genetically engineering a Gram-negative microorganism to produce a lipid A mimetic;

ii) isolating the lipid A mimetic from the microorganism; and iii) assaying the lipid A mimetic for anti-sepsis activity.

In some embodiments, the invention provides a method of screening a molecule for anti-sepsis activity, comprising i) genetically engineering a Gram-negative microorganism to produce a lipid A mimetic of the following formula

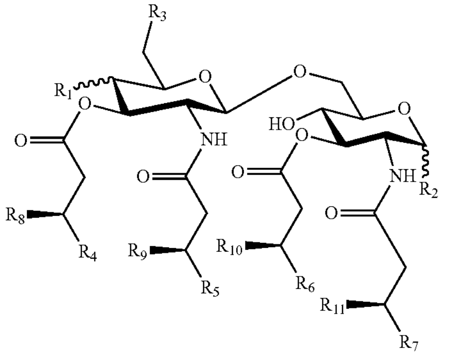

wherein $R_1$ and $R_2$ may be H, OH, protonated phosphate, a phosphate salt, a sugar phosphonate, or a mono-, di- or poly-saccharide, $R_3$ may be OH or a mono-, di- or poly-saccharide, $R_4$, $R_5$, $R_6$ and $R_7$ may be an alkyl or alkenyl chain of up to 13 carbons (for a chain of 16 carbons), and $R_8$, $R_9$, $R_{10}$ and $R_{11}$ may be H, OH, or an alkyl or alkenyl ester of up to 16 carbons.

ii) isolating the lipid A mimetic from the microorganism; and iii) assaying the lipid A mimetic for anti-sepsis activity.

The assaying method for anti-sepsis activity is not necessarily limiting and can include in vitro and in vivo methods. In some embodiments, the assaying can be performed using in vivo models of endotoxic shock. For example, animals such as mice can be treated with a lethal dose of pro-inflammatory LPS and simultaneously (or before or after) treated with an amount of the candidate lipid A mimetic.

The Gram-negative bacteria may be of any kind, including from *Acetobacter, Borrelia, Bordetella, Burkholderia, Campylobacter, Chlamydia, Enterobacter, Eshcerichia, Fusobacterium, Helicobacter, hemophilus, Klebsiella, Legionella, Leptospiria, Neisseria, Nitrobacter, Proteus, Pseudomonas, Ricketsia, Salmonella, Serratia, Shigella, Thiobacter, Treponema, Vibrio*, or *Yersinia*. In specific embodiments, one or more of the following bacteria are utilized to produce the anti-sepsis lipid A (ASLA) based therapeutic: Acetic acid bacteria, *Acinetobacter baumannii, Agrobacterium tumefaciens, Anaerobiospirillum, Arcobacter, Arcobacter skirrowii, Armatimonas rosea, Bacteroides, Bacteroides fragilis, Bacteroides ruber, Bartonella taylorii, Bdellovibrio, Brachyspira, Cardiobacterium hominis, Chthonomonas calidirosea, Coxiella burnetii, Cyanobacteria, Cytophaga, Dialister, Enterobacter, Enterobacter cloacae, Enterobacter cowanii, Enterobacteriaceae, Enterobacteriales, Escherichia, Escherichia coli, Escherichia fergusonii, Fimbriimonas ginsengisoli, Fusobacterium necrophorum, Fusobacterium nucleatum, Fusobacterium polymorphum, Haemophilus haemolyticus, Haemophilus influenzae, Helicobacter, Helicobacter pylon, Klebsiella pneumoniae, Legionella, Legionella pneumophila, Leptotrichia buccalis, Escherichia coli, Luteimonas aestuarii, Luteimonas aquatica, Luteimonas composti, Luteimonas lutimaris, Luteimonas marina, Luteimonas mephitis, Luteimonas vadosa, Megamonas, Megasphaera, Meiothermus, Methylobacterium fujisawaense, Morax-Axenfeld diplobacilli, Moraxella, Moraxella bovis, Moraxella osloensis, Morganella morganii, Negativicutes, Neisseria cinerea, Neisseria gonorrhoeae, Neisseria meningitidis, Neisseria sicca, Nitrosomonas eutropha, Nitrosomonas halophila, Nitrosomonas oligotropha, Pectinatus, Pelosinus, Pontiac fever, Propionispora, Proteobacteria, Proteus mirabilis, Proteus penneri, Pseudomonas, Pseudomonas aeruginosa, Pseudomonas, Pseudomonas luteola, Pseudoxanthomonas broegbernensis, Pseudoxanthomonas japonensis, Rickettsia rickettsii, Salmonella, Salmonella bongori, Salmonella enterica, Salmonella enterica* subsp. *enterica, Selenomonadales, Serratia marcescens, Shigella, Sorangium cellulosum, Sphaerotilus, Spirochaeta, Spirochaetaceae, Sporomusa, Stenotrophomonas, Stenotrophomonas nitritireducens, Thermotoga neapolitana, Trimeric autotransporter adhesin, Vampirococcus, Verminephrobacter, Vibrio adaptatus, Vibrio azasii, Vibrio campbellii, Vibrio cholerae, Vitreoscilla, Wolbachia*, or *Zymophilus*.

In some embodiments, the anti-sepsis lipid A (ASLA) based therapeutics are produced by Gram-negative microorganism *Yersinia pestis*. In some embodiments, the Gram-negative microorganism is *Yersinia pestis* KIM6 strain.

In some embodiments, the Gram-negative microorganism is engineered to express one or more non-endogenous lipid A biosynthetic enzymes, inactivate/delete one or more endogenous lipid A biosynthetic enzymes, modify one or more endogenous lipid A biosynthetic enzymes, and/or increase or decrease expression of one or more endogenous lipid A biosynthetic enzymes. In some embodiments, the lipid A biosynthetic enzyme is from one or more of *Yersinia pestis, Pseudomonas aeruginosa, Acinetobacter baumannii, Francisella novicida, E. coli, Bordetella* subspecies, *Helicobacter pylori, Leptospira interrogans* or *Salmonella typhimurium*. In some embodiments, the lipid A-modifying enzyme can include phoP, lpxP, msbB, lpxE, pagP, and/or lpxF.

Kits

Any of the compositions described herein may be comprised in a kit. In a non-limiting example, one or more anti-sepsis lipid A (ASLA) based therapeutics and/or bacterial strains to produce them and/or reagents for modifying the bacteria are comprised in a kit. In some embodiments, one or more reagents for modifying, culturing, and/or extracting from bacteria are include in the kit.

In some embodiments, one or more anti-sepsis lipid A (ASLA) based therapeutics are included in the kit and may or may not be formulated with another agent. In some embodiments, the other agent can be an antibiotic or other anti-sepsis agent. The anti-sepsis lipid A (ASLA) based therapeutics may be formulated for delivery to a mammal or may be provided with one or more reagents to produce a formulation for delivery to a mammal. The bacterial strain of the kit may be provided as a bacterial stab, bacterial slant, frozen glycerol stock, or freeze-dried powder, as examples. The bacteria may be provided in the kit at a particular desired temperature, including between frozen (−80° C.) and room temperature. In embodiments, the kit comprises one or more reagents for modifying a bacteria, such as reagents to handle a recombinant vector and/or reagents to assay the bacteria for presence of the vector (such as PCR reagents, restriction enzymes, polymerases, ligases, buffers, nucleotides, etc.).

In some embodiments, the components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one components in the kit, the kit also will generally contain a second, third or other additional container into which the additional components may be separately placed. However, various combinations of components may be comprised in a vial. The kits of the present invention also will typically include a means for containing the compositions in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. In some cases, the container means may itself be a syringe, pipette, and/or other such like apparatus, from which the formulation may be applied to a desired area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means. The kits may also comprise a container means for containing a sterile, pharmaceutically acceptable buffer and/or other diluent.

Application of the teachings of the present invention to a specific problem is within the capabilities of one having ordinary skill in the art in light of the teaching contained herein. Examples of the compositions and methods of the invention appear in the following non-limiting Examples.

EXAMPLES

Example 1

Rational Design and Purification of Anti-Septic Lipid A (ASLA) Candidates

Figure 2:
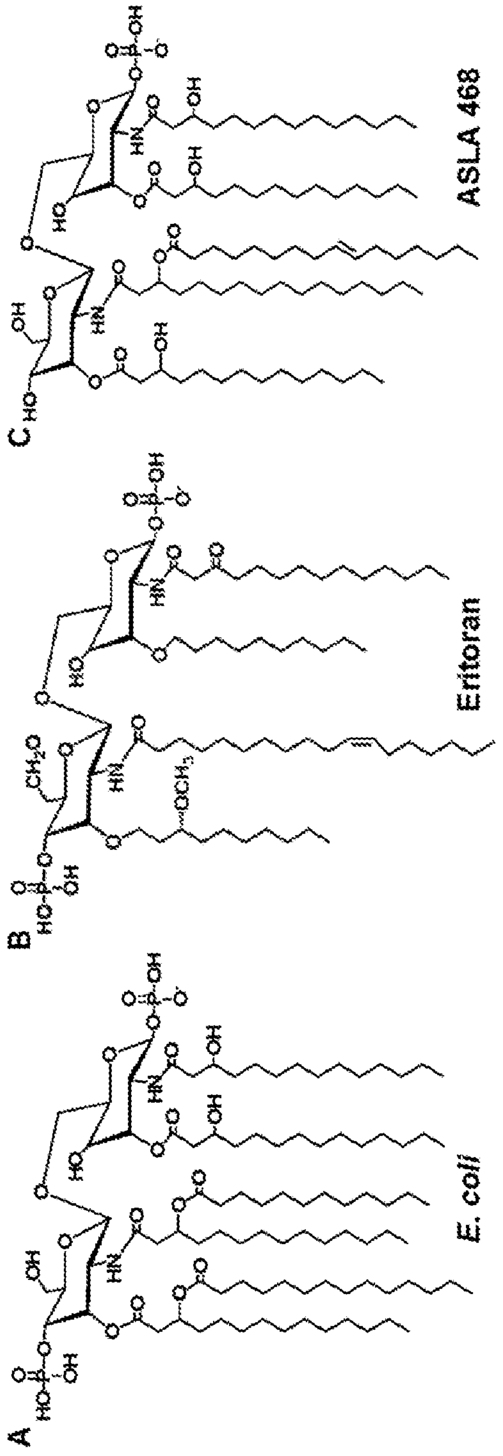
FIG. 2. Agonist versus antagonist lipid A. A.) Highly pro-inflammatory *E. coli* lipid A is di-phosphorylated and hexa-acylated with short (14 carbon), saturated fatty acids both ester- and amide-linked. B.) Eritoran is a well-characterized antagonist of MD2/TLR4; note the unsaturation on the 2'-fatty acid and the 10 carbon ether-linked fatty acids. C.) Structure of the ASLA 468 BECC-produced molecule derived from an engineered strain of *Y. pestis* grown at 26° C. Note the base structure similarities to *E. coli* lipid A.

Therapeutic approaches to treat sepsis have focused primarily on reducing hypercytokinemia (cytokine storm) and reducing the bacterial load in the blood with limited efficacy. Here, we strive to approach the upstream events mediating the systemic reaction to Gram-negative sepsis at the level of activation of TLR4 by pro-inflammatory forms of LPS. To date, attempts to block or inhibit TLR4 activity have been developed using synthetic mimetics, such as Eritoran, which was effective in inhibiting TLR4 activation, but did not improve patient survival. Torio et al. Healthcare Cost and Utilization Project (HCUP) Statistical Brief, #160, 2013, 1-12; Tse, M. T. *Nat Rev Drug Discov* 2013, 12, 334-334; Cohen, J. *Nature* 2002, 420, 885-891; Opal et al., *JAMA* 2013, 309, 1154-1162. The structural dissimilarities between native lipid A (FIG. 2A) and Eritoran (FIG. 2B) are likely the cause of this failure, as well as poor clinical trial design (insufficient power to evaluate a reduction in mortality, patient randomization, and the underlying hypothesis being incorrect). Hotchkiss, R. S.; Nicholson, D. W. *Nat. Rev. Immunol.* 2006, 6, 813-822; Tse, M. T. *Nat Rev Drug Discov* 2013, 12, 334-334. The minimal component of LPS necessary for TLR4 stimulation is lipid A, the membrane anchor component of LPS; receptor agonism is structurally dependent on modifications to the lipid A base structure. We have designed and evaluated preliminary anti-sepsis lipid A-based (ASLA) therapeutics using a crude lipid A:TLR4 SAR as a guide. We have shown that our current ASLA molecules (ASLA 468/470, FIG. 2C) out compete pro-inflammatory lipid A binding to MD2-TLR4. Our proven biosynthetic method (i.e. bacterial enzymatic combinatorial chemistry, BECC) is a route to produce lipid A mimetics (and standards) that is fast, efficient, and very cost effective (patent pending WO2014/138696A1). BECC also offers the advantage of ease of manipulation of immunostimulatory properties of a final ASLA product by starting with the rationally engineered, custom-designed structural properties of the molecule. To date, two proof-of-principle ASLA molecules, one of which is shown in FIG. 2C, have been generated and evaluated demonstrating low TLR4 activation and high competitive index in the presence of pro-inflammatory lipid A.

Example 2

Competitive Inhibition of TLR4 Signaling by ASLA 468 and 470

Figure 3:
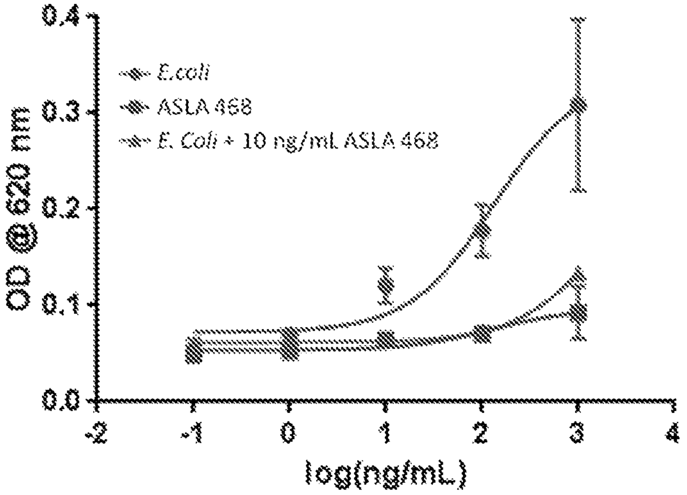
FIG. 3. Competitive inhibition of *E. coli* LPS by ALSA 468. THP-1 Dual cells (Invitrogen) contain an easily detected secreted alkaline phosphatase (SEAP) under the NFκB promoter. *E. coli* LPS (circles), ALSA 468 (squares), and *E. coli* LPS+a constant 10 ng/mL ASLA 468 (triangles) are cultured with THP-1 Dual over a 5-log dilution series, activation of NFκB, as measured by SEAP expression, is pictured.

To investigate the inflammatory properties of BECC synthesized molecules ASLA 468 and 470, THP-1 Dual cells (Invitrogen) were used to screen for NF-κB activation. Over thirty BECC molecules were screened in a five-log dilution series and placed into a full, partial, or weak agonist category (8 full, 5 partial, and 11 weak), as compared to Ec LPS used as a positive control. From this initial screen, ASLA 470 and 468 were identified as weak agonists with a high affinity for the receptor, as evidenced by a low EC50 (Ec 3.2 ng/ml vs 121.2 ng/ml ASLA 468). These characteristics made ALSA 468 a strong candidate to outcompete pro-inflammatory forms of lipid A, and therefore combat the adverse symptoms of sepsis resulting from hypercytokinemia. Using our established cell culture system, the ability of ASLA 468 to competitively inhibit Ec LPS-driven inflammation was tested (FIG. 3). A concentration of 10 ng/mL ASLA 468 added to the five-log dilution scheme of Ec increased the EC50 11.8 fold, confirming that ASLA 468 is a competitive inhibitor of sepsis-causing LPS. This successful ALSA 468 molecule is a result of further refining the previously observed successful ASLA 470 molecule that increased the EC50 of Se LPS 1.9 fold. By screening and refining lipid A structures using our BECC method, we will optimize the receptor occupancy profile while minimizing activation in a competitive manner.

Example 3

Figure 4:
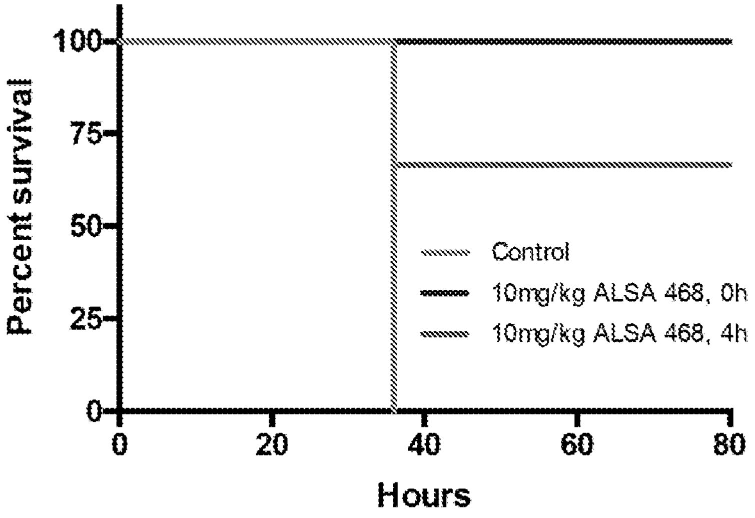
FIG. 4. ALSA 468 therapeutically rescues mice from lethal endotoxic shock. Lethal endotoxic shock was induced in 6-8 week old C57BL6 mice by injecting 25 mg/kg of *E. coli* LPS (strain W3110) i.p. Animals were then treated with 10 mg/kg ALSA 468 i.p. simultaneously (line, n=3) or 4 hours post induction (line, n=3), control animals (line, n=3) were left untreated.

Survival of Mice Therapeutically Treated with ASLA 468 in Lethal Model of Endotoxic Shock To determine if ASLA 468 is capable of therapeutically rescuing mice that have received a lethal dose of pro-inflammatory Ec LPS, an in vivo mouse model of lethal endotoxin septic shock was used. Medzhitov, R. *Nat. Rev. Immunol.* 2001, 1, 135-145; Remick et al., *Shock* 2000, 13, 110. In a preliminary experiment, all control mice treated with 25 mg/kg Ec LPS succumbed to endotoxemia by 36 hours post-induction, whereas mice simultaneously treated with 25 mg/kg Ec LPS and 10 mg/kg ALSA 468 showed a 100% survival rate. Additionally, mice therapeutically treated with 10 mg/kg ASLA 468 administered 4 hours after the 25 mg/kg Ec LPS lethal septic shock induction had a 66.6% survival rate (FIG. 4). In a subsequent repeat experiment aimed at extending time to treatment, we observed 100% survival of mice treated 8 hours post-induction and 66.6% survival of mice treated 12 hours post-induction. Finally, mice injected with ASLA 468 alone showed no signs of pathogenic symptoms. These pilot experiments provide a proof-of-principle that molecules found to compete with pro-inflammatory LPS in vitro are also capable of combating symptoms of septic shock in vivo. Future sepsis models to be used in this proposal will account for bacterial clearance after antibiotic treatment, in vivo location and concentration of LPS, and the structural relationship between ASLA and MD2/TLR4 complex that will address some shortcomings of previous anti-sepsis therapeutics, which is the scientific premise of this proposal. Raetz et al., *Annu. Rev. Biochem.* 2002, 71, 635-700; Raetz et al., *J. Lipid Res.* 2009, 50 Suppl, S103-108; Needham et al., S. *Nature Reviews Microbiology* 2013, 11, 467-481; Ernst et al., *Science* 1999, 286, 1561-1565; Miller et al., *Nature Reviews Microbiology* 2005, 3, 36-46; Siegemund et al., *Nat Immunol* 2012, 13, 1031-1033; Rietschel et al., *FASEB J.* 1994, 8, 217-225; van Lieshout et al., *Inflamm. Res.* 2014, 63, 927-933; Buras et al., *Nat Rev Drug Discov* 2005, 4, 854-865.

Example 4

Tissue Mapping of Lipid A by Mass Spectrometry Imaging (MSI)

The direct detection and mapping of de novo lipid A structures in vivo is not possible with traditional analytical techniques. Mass spectrometry imaging (MSI), a mass/charge based molecular histological technology allows for the direct mapping of molecules like lipid A and ASLA's without disrupting the tissue architecture. Akashi et al., *J. Exp. Med.* 2003, 198, 1035-1042; Shimazu et al., *The Journal of Exp. Medicine* 1999, 86, 973-983; Heeren, R. M. A. *International Journal of Mass Spectrometry* 2014, 362, 40-47; Caprioli et al., *Anal. Chem.* 1997, 69, 4751-4760.

Figure 5:
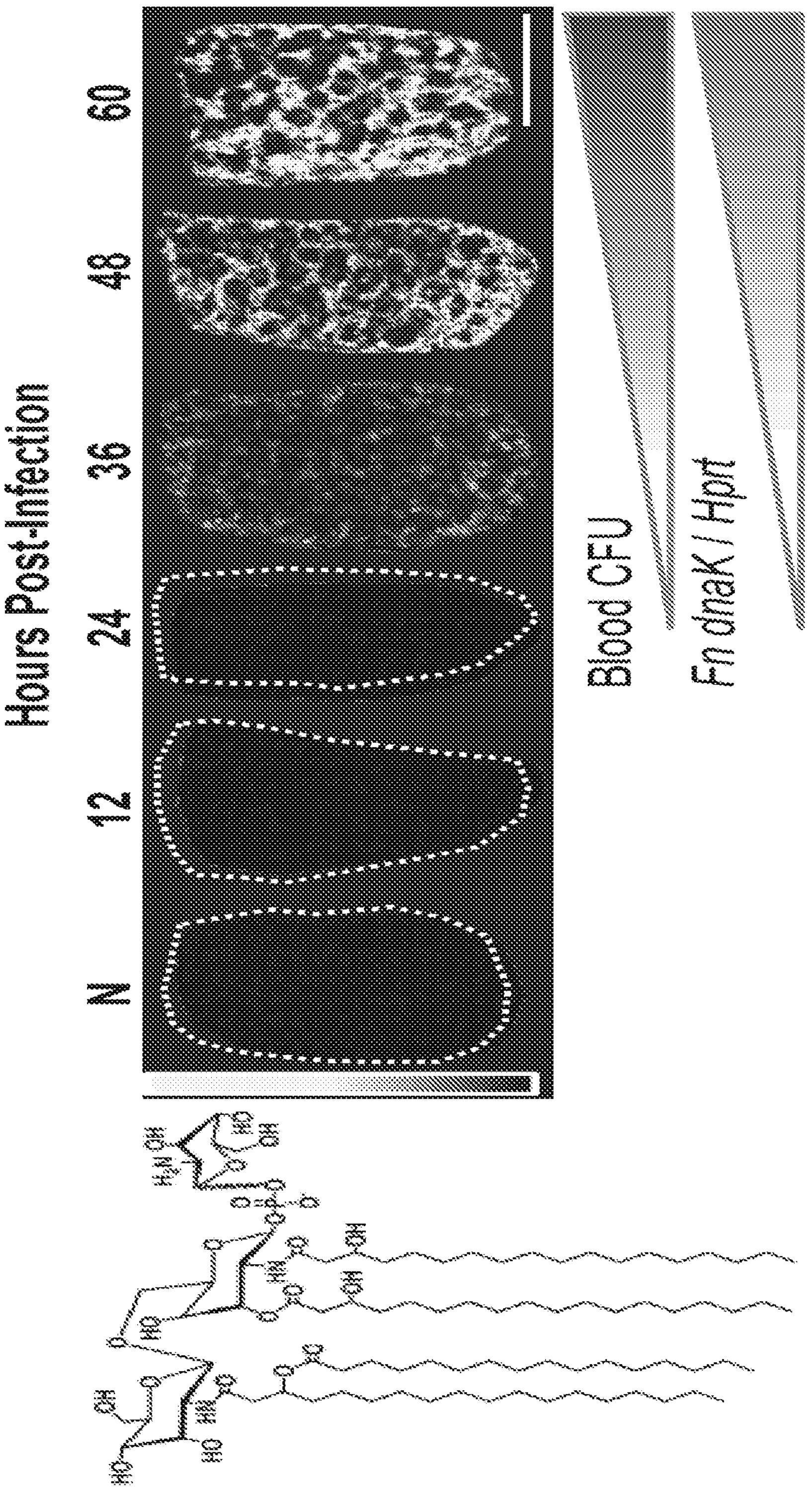
FIG. 5. MALDI-MSI of lipid A distributed in red pulp of mouse spleen. (LEFT) Predominant structure of *Francisella novicida* (Fn) lipid A given as negative ion $[M-H]^-$ (m/z 1665.1) and ion map of Fn lipid A in half-spleens. 50 μm spatial resolution. False color map, relative intensity bar, 0-50%. Dotted outlines: negative tissues. Labels: hours or naïve (N). Bacterial dissemination (Fn), cardiac blood, post-mortem (red) and RNA confirmation in second half of bisected spleens. Fn dnaK transcript normalized to murine Hprt. n=3.
Figure 6:
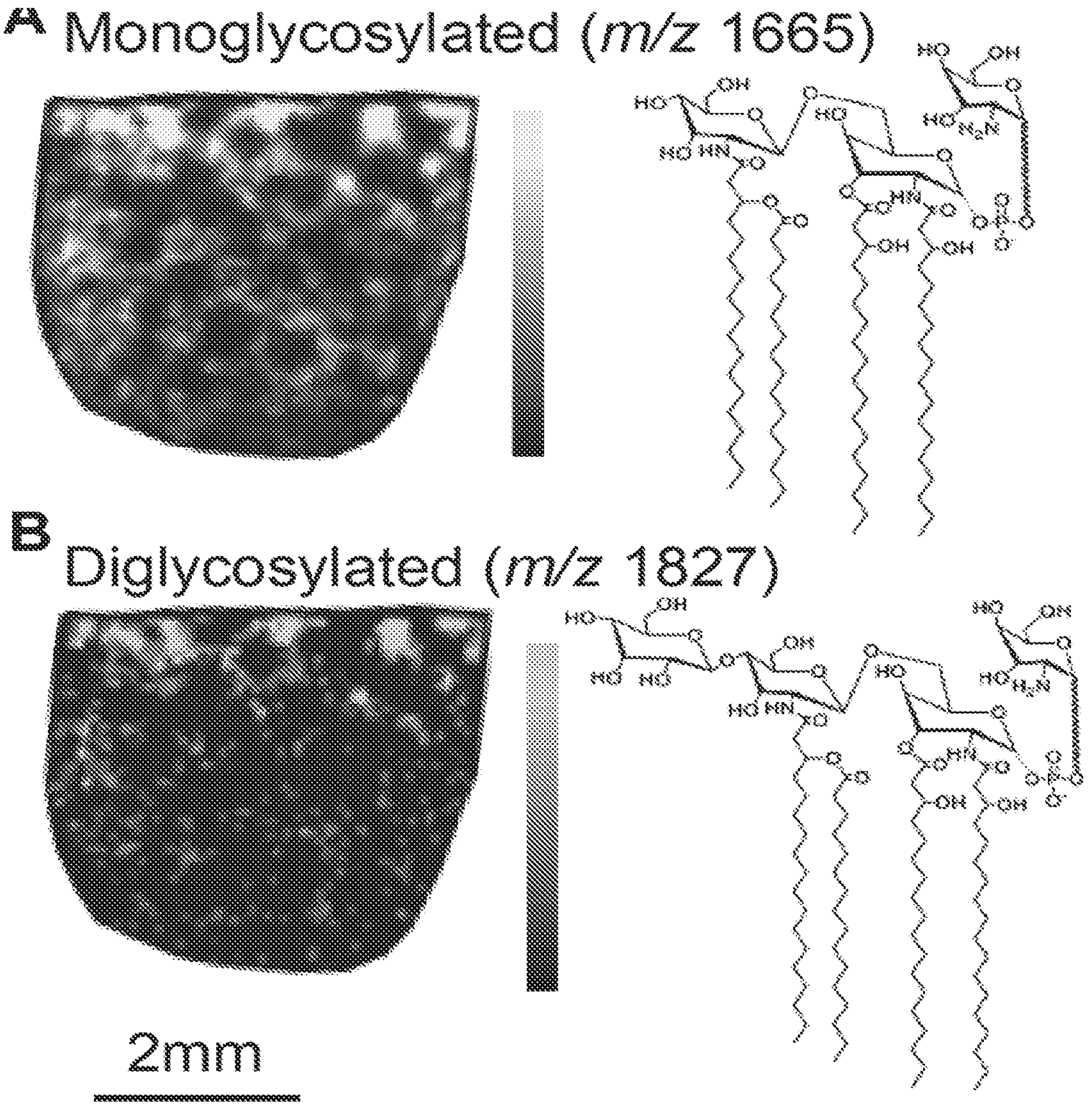
FIG. 6. Co-detection of multiple lipid A species from mouse spleen. Mouse infected with ~300 CFU Fn, spleen collected at 60 hours post-infection, imaged at 75 micron resolution (MALDI-FT-ICR-MS). A.) Most abundant lipid A ion (m/z 1665, yellow) detected in spleen was monoglycosylated at the 1-phosphate. B.) Diglycosylated lipid A detected (m/z 1827), highlighting the ability to detect structural variants of lipid A by MSI.
Figure 7:
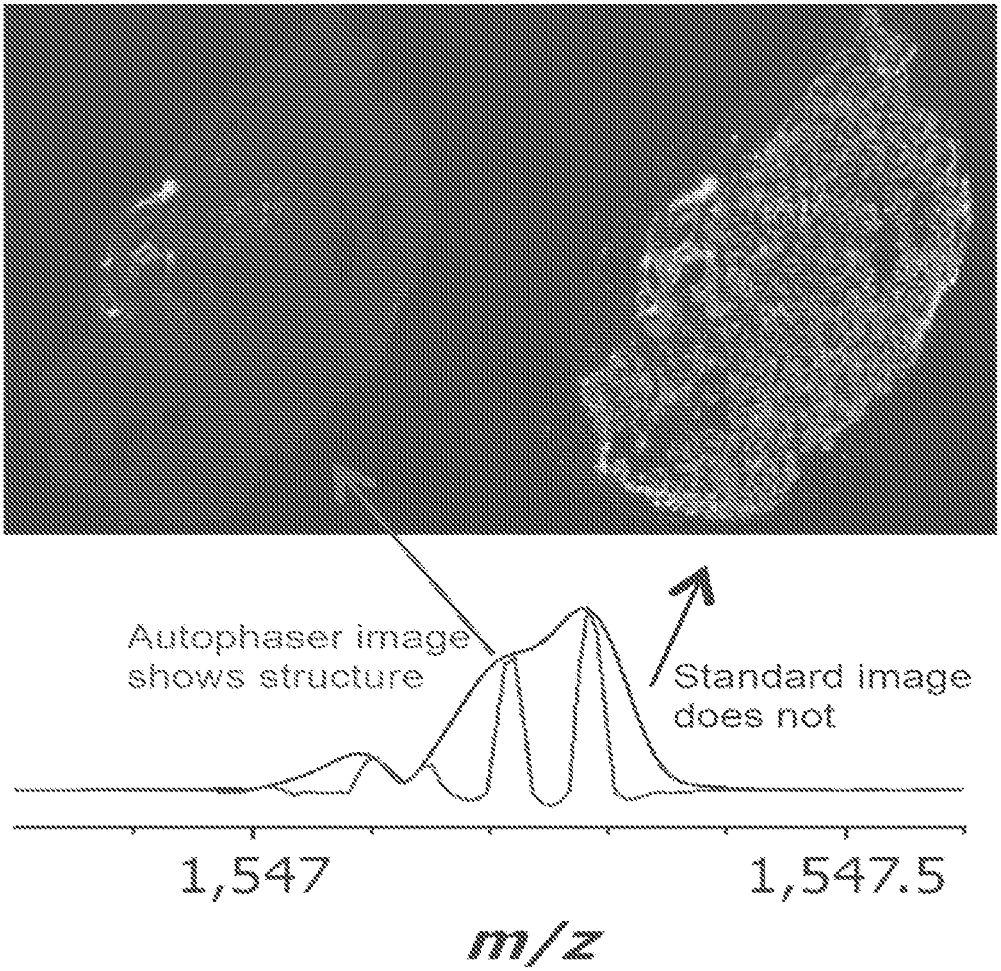
FIG. 7. Absorption mode imaging improves peak resolution and mapping. MSI data from mouse lung tissue. The black trace (lower) demonstrates standard magnitude mode mapping (upper right), note uniform distribution of the magnitude mode signal. The trace (lower) illustrated the presence of two, baseline resolved absorption mode peaks underlying the magnitude mode peak. Distribution of the left absorption mode peak is shown on-tissue (upper left) demonstrates that these peaks are unique features.

FIG. 5 shows unpublished MALDI-TOF MSI results laboratories demonstrating for the first time, detection and distribution of lipid A in an infected organ. In these results, mice were infected with a lethal dose of Francisella novicida (Fn), which makes an unique lipid A structure that is exclusively bacterial in origin, followed by MSI detection of lipid A in splenic tissue. The transition to sepsis at approximately 36 hours post-infection is clearly observed by blood CFU, presence of bacterial transcript in burdened tissue, and steadily increasing lipid A abundance. Detection of 'free' lipid A by MSI, such as that produced by Fn or the ASLA-type BECC molecules are now routinely detected in our laboratories. On-tissue mapping of fully extended LPS will require liberation of lipid A. To do so, we have developed an on-tissue hydrolysis method capable of releasing lipid A from LPS in situ allowing for the mapping of bacteria responsible for sepsis as well as ASLA therapeutic molecules. By combining our methodological advances, we can co-map pro- and anti-inflammatory lipid A structures on tissue. Finally, structural discrimination of heterogeneous lipid A mixtures within tissue is possible using MSI directly in splenic tissue (m/z 1665 vs 1827—addition of a galactosamine moiety Δ162 m/z), as demonstrated in FIG. 6. Oblak et al., *Molecular Immunology* 2015, 63, 134-142; Shaffer et al., *J. Am. Soc. Mass Spectrom.* 2007, 18, 1080-1092. However, to reliably discriminate small mass differences by MSI, enhanced resolution, mass accuracy and better tandem MS techniques are needed.

Example 5

Absorption Mode Enhances Resolution and Mass Accuracy

The confidence with which one can assign a peak in a mass spectrum or a mass spectral image depends on both mass resolving power and mass accuracy. Ohto et al., *Proc. Natl. Acad. Sci. U.S.A* 2012, 109, 7421-7426; Smith et al., *Anal. Chem.* 2013, 85, 11180-11184. Mass resolving power allows closely spaced peaks to be separated and hence identified individually while mass accuracy provides confidence that the assignment for each peak is correct. Increases in resolution and accuracy will be gained by further refinements to novel Autophaser software developed by our collaborator Prof. Kilgour (see letter of support) that uses data from a MALDI Fourier transform ion cyclotron resonance mass spectrometer (MALDI FT-ICR MS). Lohmann et al., *J. Endotoxin Res.* 2003, 9, 33-37; Lohmann et al., *J. Endotoxin Res.* 2007, 13, 235-242; Kilgour et al., *Anal. Chem.* 2013, 85, 3903-3911. The use of MALDI FT-ICR MS for high mass-resolution analysis of substances is rapidly gaining popularity in the biomedical sciences. Kim et al., *Cell* 2007, 130, 906-917; Park et al., *Nature* 2009, 458, 1191-1195.; Kilgour et al., *Rapid Commun. Mass Spectrom.* 2013, 27, 1977-1982. Extracting signal from the background noise, however, poses significant challenges. Autophaser will be used to improve both resolution and mass accuracy of our collected images by producing absorption mode data that can discriminate mass differences as small as 0.1 mass unit. Ohto et al. *Science* 2007, 316, 1632-1634; Kilgour et al., *Rapid Commun. Mass Spectrom.* 2015, 29, 1009-1018; Kilgour et al., *Rapid Commun. Mass Spectrom.* 2015, 29, 1087-1093. Subsequently, we will map molecules to different tissue locations using the bespoke software tool, Little Imager.

Example 6

Hybrid Ion Mobility Spectrometer QExactive Orbitrap (IMS-QE OT)

Figure 8:
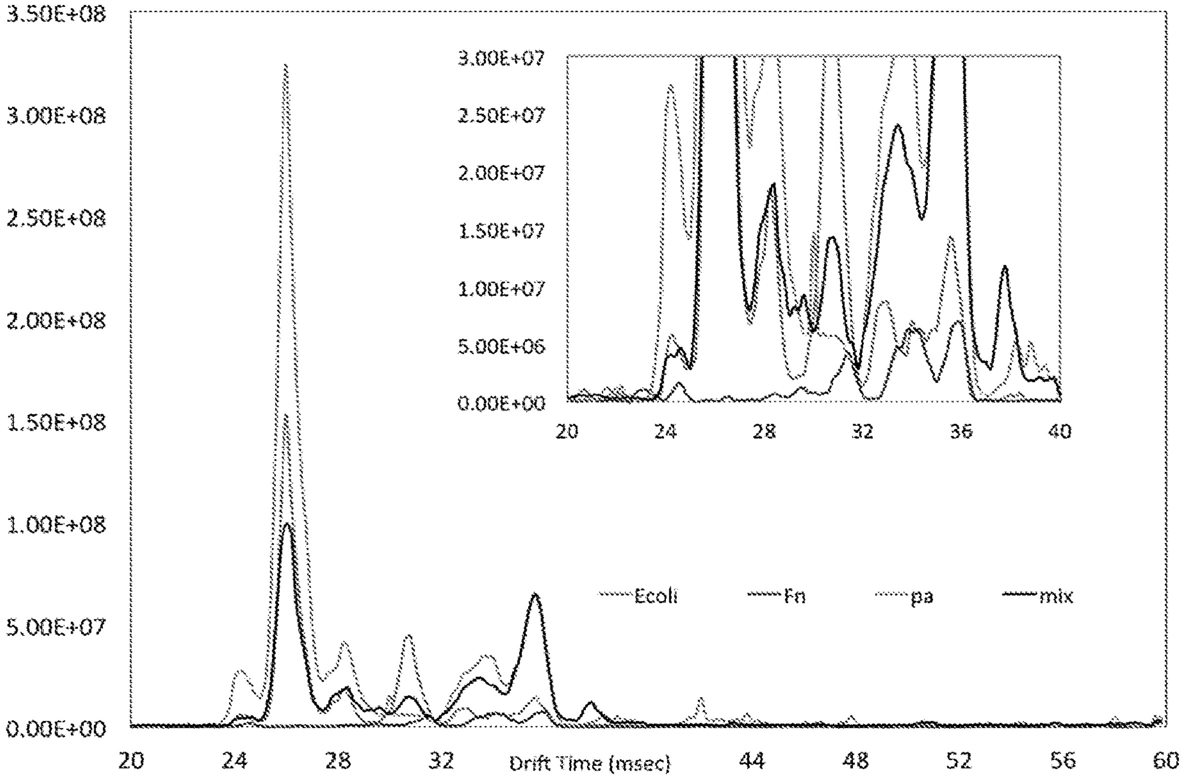
FIG. 8. IMS-QE separation of lipid A mixture. Separation lipid A mixture from *E. coli, Pseudomonas aeruginosa* and *Francisella novicida*. (y-axis: Intensity, arbitrary; x-axis: drift time, msec).

Determination of lipid A/ASLA metabolism in complex biological samples will require high sensitivity detection and structural characterization. Ion mobility spectrometry (IMS) offers shape-based separations orthogonal to mass/charge. Ohto et al., *Proc. Natl. Acad. Sci. U.S.A* 2012, 109, 7421-7426; Ohto, U.; Fukase, K.; Miyake, K.; Satow, Y. *Science* 2007, 316, 1632-1634; Kim et al., *Nature* 2009, 458, 1191-1195; Kanu et al., *J. Mass. Spectrom.* 2008, 43, 1-22. In collaboration with Spectroglyph (Kennewick, Wash.), the Goodlett lab developed a novel coupling of a fast scanning quadrupole Orbitrap (QE-OT) MS to an IMS device. Ions are injected by ESI into an ion funnel trap from which they are pulsed into a 100 cm-long drift tube with stacked-ring ion guides that interface to the OT via an Ion Gate. Per each IMS experiment, 2N-1 ion packets are injected into the drift tube using a waveform based on a pseudo-random sequence of N-bits. The same waveform is applied to the IMS Ion Gate and shifted sequentially in time. At each delay step, OT spectra are acquired, exhibiting signals of concurrently detected N-ion packets. The acquired multiplexed spectra are inverse-transformed to reconstruct the original data vector. FIG. 8 shows separation of a mixture of three unrelated lipid A molecules. What cannot be seen is that each of the individual extracts have dozens of species from which individual mass/charge values may be selected for tandem MS by higher-energy collision dissociation (HCD) improving characterization complex mixtures.

Example 7

Cartesian Product Lipid A Structure Prediction

Building on our prior approaches to lipid A structure assignment, we developed an extensive theoretical $MS^1$ database to identify lipid A structures without need for $MS^n$ (n≥2) data. Ohto et al., *Cell* 2007, 130, 906-917; Park et al., *Nature* 2009, 458, 1191-1195; Ting et al., *J. Am. Soc. Mass Spectrom.* 2011, 22, 856-866. Liang, T. 62nd ASMS Poster; 2014 American Society for Mass Spectrometry Meeting. Briefly, each of eight structural components (FIG. 9) is considered as a module to construct a hypothetical lipid A structure. Precursor ion masses detected from a lipid A mass spectrum are compared against an $MS^1$ theoretical database of all possible structures and the top n matches are selected based on a match to the available molecular masses. A Cartesian product algorithm was then used to compute the theoretical arrangements of lipid A from and imported into a MySQL database for analysis. This produced 2.2 billion theoretical lipid A masses, >99.9% of which were not viable biologically, but serve as decoys to estimate false discovery rates.

Example 8

Define and Refine ASLA Structures Protective Against Gram-Negative Sepsis Using Bacterial Enzymatic Combinatorial Chemistry (BECC) Approach Rationale: determine ASLA activity in vitro. We have engineered and purified two preliminary anti-sepsis lipid A (ASLA) molecules using our BECC system (ASLA 470 and 468) wherein lipid A biosynthetic and/or modifying enzymes are heterologously expressed in a bacterial species with a structurally minimal lipid A as a base. Using this system, we have the ability to customize lipid A synthesis for large-scale and inexpensive production of novel, potentially therapeutic ASLA molecules. These molecules have been successfully evaluated for a low pro-inflammatory cytokine profile, high competitive index against inflammatory lipid A, and protection in a lethal endotoxin murine model. In silico receptor modeling of these engineered lipid A structures will present a unique opportunity to determine the minimal structural components necessary for activation and will contribute to our understanding of the lipid A:MD2/TLR4 SAR.

Experimental Design and Methods

Determine SAR of engineered ASLA molecules in context of MD2/TLR4 complex using molecular modeling. Modeling studies will be undertaken to investigate the relationship of variations in lipid A structure to binding to the MD2/TLR4 complex and subsequent dimerization and activation. Once this relationship is understood, it will be used to rationally design therapeutics for sepsis that compete for lipid A binding without allowing for MD2/TLR4 complex dimerization. Calculations will focus on the impact of lipid A variants ($LA_v$) on dimerization, involving $LA_v$ models to MD-2 in complex with TLR4 (MD2/TLR4-$LA_v$) as both a monomer (MD2/TLR4-$LA_v$) and a dimer ((MD2/TLR4-$LA_v$)$_2$) for each $LA_v$. Molecular Dynamic (MD) simulations will be performed using an explicit solvent representation on the MD2/TLR4-LA complex. Analysis of the simulations will focus on identifications of interactions between monomers in the dimer that contribute to dimerization and between $LA_v$ and the monomer that could lead to a loss of binding. Initial analysis will focus on identification of specific regions of the molecule that contribute to dimerization versus those that stabilize interactions with the monomer required for binding. This will allow for prioritization of the building blocks to be used for construction of novel $LA_v$ that will subsequently be simulated and analyzed with the results used to develop our SAR model. Our MD simulations will be based on the PDB structure, 3FXI, in which the outer core of LPS has been removed, yielding lipid A. Park et al., *Nature* 2009, 458, 1191-1195. Initial models of $LA_v$ will be based on alignment of the common atoms with Lipid A, with the remaining atoms built using the internal coordinate capabilities in CHARMM. Brooks et al., *J. Comput. Chem.* 2009, 30, 1545-1614. MD simulations will be performed with Gromacs in explicit solvent using the TIP3P water model, following published protocols. Van Der Spoel, D et al., *J. Comput. Chem.* 2005, 26, 1701-1718; Hess et al., *Journal of Chemical Theory and Computation* 2008, 4, 435-447; Jorgensen et al., *Journal of Chemical Theory and Computation* 2009, 5, 2353-2370; Kern et al., *Biophysical Journal* 2014, 107, 1885-1895; Wu et al., *Biophysical Journal* 2015, 109, 2090-2100. Force field parameters will be the additive C36 carbohydrate, protein, lipid, and CGenFF parameters. Guvench et al., *Journal of Chemical Theory and Computation* 2011, 7, 3162-3180; Guvench et al., *Journal of Chemical Theory and Computation* 2009, 5, 2353-2370; Best et al., *Journal of Chemical Theory and Computation* 2012, 8, 3257-3273; Klauda et al., *J. Phys. Chem.* 2012, 114, 7830-7843; Vanommeslaeghe et al., *J. Comput. Chem.* 2010, 31, 671-690. All simulations (298 K, 1 atm in NPT ensemble) will be performed for a minimum of 1 μsec. to assure that conformational changes due to $LA_v$ in the protein can occur. Vanommeslaeghe, K. Feller et al., *Journal of Chemical Physics* 1995, 103, 4613-4621.

Harvest, express, and evaluate novel lipid A biosynthetic enzymes from sponges and extremophile bacteria. A library of lipid A modifying enzymes will be built based on known enzymes and discovery of novel enzymes found in novel bacteria and in under-characterized lipid A producing hyperthermophilic bacteria. Raetz et al., *Annu. Rev. Biochem.* 2007, 76, 295-329. Initially, we will use a library of up to 200 bacteria from marine sponges as a resource for leads for novel synthetic enzymes. These bacteria will be screened for novel structures and/or cytokine activities that point to the possibility of novel lipid A remodeling enzymes. Additionally, an extensive array of hypothermophilic bacteria will be provided to survey for novel lipid A structures/activities. We anticipate lipid A analysis on 50-75 bacterial backgrounds yearly. Upon review of novel lipid A structures/activities described in the parallel goals and concurrent works of the Examples, we will use unbiased in silico tools to predict and identify enzymes involved in lipid A biosynthesis, which will increase the scientific rigor of our conclusions. Since these are novel bacterial strains, it will be necessary to prepare genomic DNA for sequencing and genome assembly. We commonly prepare sequencing libraries using commercial kits (Illumina, EpiCenter) for submission to fee-for-service high-throughput sequencing facilities (the Institute for Genome Sciences, Core Services, UMB). Bacterial genome assemblies will be processed on the cloud-based CloVR-Microbe software. We will identify lipid A-modifying genes using translated homology searches seeded with known enzymes. We have used this approach to identify previously undescribed lipid-A modifying enzymes in *Pseudomonas, Francisella*, and other bacterial species. Li et al., *Proc. Natl. Acad. Sci. U.S.A.* 2012, 109, 8716-8721.

Rationally design and produce novel ASLA candidates using our BECC method. Using data generated from the in silico structural modeling studies, to prioritize ASLA building blocks, we will assign crucial structural components for receptor interaction. We will further characterize our current ASLA molecules, as defined below, and use BECC to synthesize additional structures based on these preliminary studies. Our BECC system is centered on *Yersinia pestis* (Yp) strains that produce unique lipooligosaccharide (LOS)/lipid A structures when grown at host (37° C.) or arthropod vector (26° C.) temperatures. Plasmids expressing individual lipid A modifying enzymes are expressed in trans in the genetically tractable, avirulent Yp strains KIM6 and/or KIM10. Yp strain backgrounds to be used are exempt from select agents status and are approved for use under BSL-2 laboratory practices as they lack specific virulence determinants, the pigmentation locus (pgm) and the pCD1 plasmid required for virulence (www.selectagents.gov). An example of one of the successful BECC designed molecules, as compared to the structure of Ec lipid A and Eritoran is given in FIG. 2C. We will engineer novel structures varying by presence or absence of specific phosphate, acyl, and carbohydrate groups by heterologous expression of lipid A biosynthesis enzymes (acyltransferase, deacylases, phosphatase and/or glycosyl-transferases) obtained from a wide variety of bacterial backgrounds to rapidly engineer unique TLR4 antagonists. To date, we have assembled a functionally validated bacterial enzyme 'toolbox' consisting of six site-diverse acyltransferase, two phosphatases, two deacylases, two sets of global regulators, and one glycosyltransferase. These lipid A-modifying enzyme cassettes have been engineered for optimal expression and robust function and can be used in combination with inducible and/or constitutive promoters to customize the extent of lipid A modification. We propose to use the two existing ASLA molecules and modeling data to instruct the development of up to five ASLA molecules per year to further their overall potential for therapeutic use.

Evaluate engineered ASLA candidates in vitro. Newly synthesized BECC-designed molecules will be purified and tested in a dose-dependent manner using in vitro systems to measure human and murine TLR4 potency, competition of *E. coli* (Ec) lipid A, and cytokine induction profiles. Initially we will use two small-scale LOS extraction protocols that require small overnight cultures (~5 mls). These methods include a phenol- and an ammonium hydroxide/isobutyric acid-based protocol, which are robust extraction techniques we routinely use. Westphal, O.; K. Jann, *Methods in Carbohydrate Chemistry,* 1965, 5, 83-91; Hamidi et al., *J. Lipid Res.* 2005, 46, 1773-1778. After extraction, lipid A will be liberated from these LOS preparations using gentle hydrolysis, which preserves labile moieties (e.g., phosphate and carbohydrate moieties) that are sensitive to acid treatment. In Example 11 we will use a variety of established MS methods such as MALDI-TOF-MS and ESI-MS/MS to characterize base structures of lipid A in both negative- and positive-ion mode. Li, Y.; Powell et al., *Proc. Natl. Acad. Sci. U.S.A.* 2012, 109, 8716-8721; Kanistanon et al., *Infect Immun* 2012, 80, 943-951; Jones et al., *J. Am. Soc. Mass Spectrom.* 2010, 21, 785-799. Large-scale LOS preparations will be extracted using a hot phenol/water extraction method. Subsequently, LOS will be treated to ensure purity from contaminating nucleic acids and proteins, extracted to remove contaminating phospholipids and TLR2-agonist proteins, and when required, converted to lipid A by mild hydrolysis. Bligh et al., *Canadian Journal of Biochemistry and Physiology* 1959, 37, 1-7; Hirschfeld et al., *The Journal of Immunology* 2000, 165, 618-622. These steps ensure the generation of preparations suitable for MS structural analysis and in vitro screening experiments (vide infra). LOS/lipid A fatty acid content will be measured by gas chromatography (GC) after acid hydrolysis, methylation, and hexane extraction. From the Examples and GC-MS analysis, exact structures of isolated lipid A from WT and BECC constructed strain will be determined.

To identify the most successful ASLA candidates to be tested for efficacy in vivo, we will stimulate both human and mouse cell cultures with increasing concentrations (0.01 ng/ml, 0.1 ng/ml, 1 ng/ml, 10 ng/ml, 100 ng/ml) of novel lipid A preparations for 4 and 24 hours. All in vitro assays will be run in biological triplicate to increase the scientific rigor of experiments. Activation of inflammatory pathways will be investigated by stimulating THP-1 cells (ATTC), a human monocytic cell line, followed by multiplex analysis of cytokines in the supernatant minimally including TNF-α, IL-8, and IL-6. We will also screen ASLA molecules using THP-1 Dual (Invitrogen) and HEK293 cells transfected with human or mouse MD2/TLR4 (Invitrogen), which have an easily detectable SEAP transcript under the NF-kB promoter to quickly evaluate the potential for these ASLA molecules to inhibit MyD88-NF-kB activation. To account for authentication of key biological resources, all cell lines were purchased from and verified by either ATCC or Invitrogen within the past year and cells used in experiments have been passaged less than 15 times since purchase. Together, these assays will illustrate a lack of inflammatory activation when cells are stimulated with the ASLA molecules. Additionally, competition studies will be performed in the same cell culture systems to define the ability of ALSA molecules to inhibit pro-inflammatory Ec lipid A from stimulating TLR4.

Example 9

Develop Methods to Improve Lipid A Structure Analysis and Screening from Extracts Develop novel, cutting edge capabilities to more efficiently screen extracts. Newly developed methods will be immediately put into service to aid outcomes in Examples 8, 10 and 11. Specifically, we will refine the existing techniques necessary for in-depth structural analysis and on-tissue release of lipid A.

Figure 9:
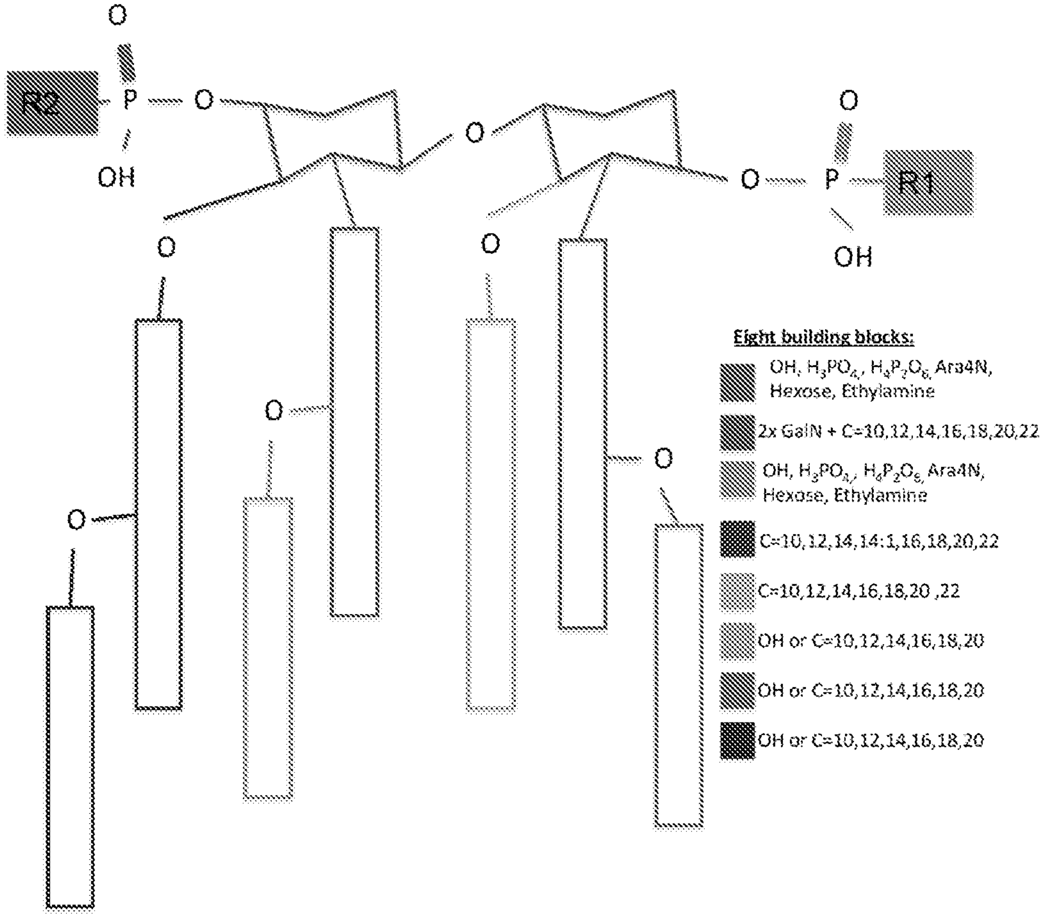
FIG. 9. Eight fundamental building blocks used in the Cartesian product methods to generate all possible MS1 masses.
Figure 10:
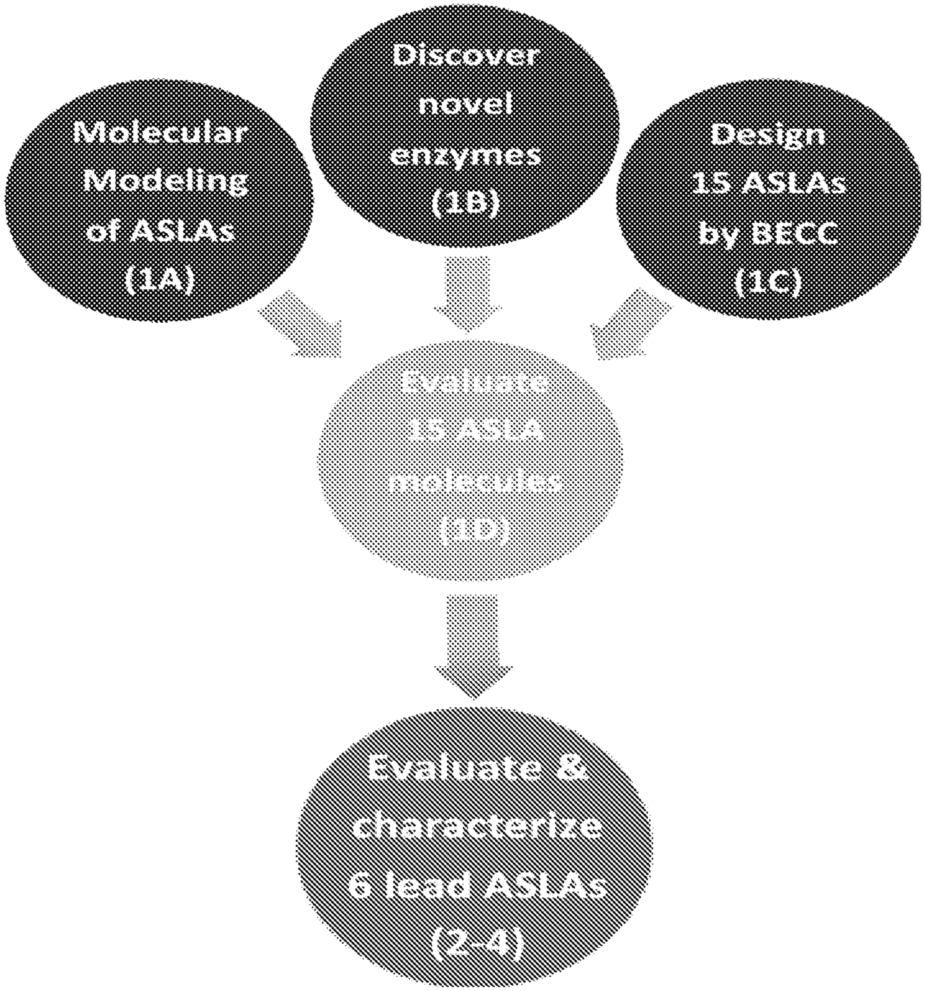
FIG. 10. Focused approach to discover, model, design, and evaluate novel ASLA molecules.

Screen bacterial extracts for novel lipid A structures. We will screen bacterial glycolipid extracts produced in Example 8 from organisms provided by Drs. Hill and Raman and repositories such as ATCC or BEI Resources Inc, as needed, by MALDI-TOF-MS. These data will be used to refine the list of potential structures via our Cartesian product MS1 library approach that predicts possible lipid A structures (FIG. 9). Extracts with the most interesting hypothetical structures and cytokine activities will undergo tandem MS characterization in Example 11 from tissue and/or (from extracts, using our new tools and guided by prior results. Shaffer et al., *J. Am. Soc. Mass Spectrom.* 2007, 18, 1080-1092; Ting et al., *J. Am. Soc. Mass Spectrom.* 2011, 22, 856-866.

Lipid A molecules with novel structures will be passed to the modeling and BECC screening groups for use in Example 8. To speed structure assignment, we will refine the Cartesian product approach by allowing odd chain fatty acids and other phosphate or sugar modifications encountered in marine bacteria and extremophiles. The approach will be further extended to produce an $MS^2$ theoretical database via a machine learning approach that simulates CID fragmentation processes of lipid A in an ion trap to instruct the development of up to five ASIA molecules per year. Finally, all published lipid A structures will be added to our lipid A SAR library for consideration.

Develop a hybrid ESI-IMS-QE MS instrument for structure analysis. We will use the high sensitivity tandem MS capabilities afforded by the IMS-QE, in concert with the FT-ICR MS, to confirm novel structure assignments. To provide a very high sensitivity tissue imaging capability (albeit at reduced spatial resolution) to allow detection of rare lipid A species present early on in in vivo infection models in tissue, we will use the liquid extraction surface analysis (LESA) capability of our Advion Nanomate coupled to the IMS-QE. We will further improve both our detectable dynamic range and confidence in assignments by performing both mass separated data independent tandem mass spectrometry analysis (PAcIFIC) of the tissue extracts and a related IMS based data-independent fragmentation technique, based in part on prior work. Panchaud et al., *PLoS ONE* 2011, 6, e28698; Nunn et al., *PLoS ONE* 2013, 8, e7565; O'Brien et al., *Anal. Chem.* 2014, 86, 2138-2145; Ernst et al., *Science* 1999, 286, 1561-1565. Additionally, in order to improve signal/noise we will gain access to the raw data, not provided by the manufacture, by recording and processing Orbitrap transients directly, through a digitization system built from off the shelf National Instruments PXIe components from standard electronics and our own processing software that allows more advanced signal recording and processing to improve sensitivity and spectral quality.

Refine and automate our on-tissue hydrolysis method for lipid A to map and quantify dispersion of pathogenic lipid A during onset of sepsis. In order to image lipid A from a full LPS molecule within tissues from the Gram-negative infection model (Example 9), we modified well-characterized hydrolysis protocols (Caroff microextraction, mild acid hydrolysis, and others) to liberate lipid A from the KDO sugars of LPS. We have successfully adapted these methods for lipid A-spiked tissue samples and anticipate further successful refinement for ex vivo sepsis tissues. This fundamental development in methodology represents a major advance in the application of MSI for studies in bacterial pathogenesis. Here, we take the prepared, thaw-mounted tissue sections from the mouse infection model (Example 9) and hydrolyze LPS to lipid A on-tissue. Several examples of this type of on-tissue digestion approach exist for other molecular targets to enable subsequent MSI experiments. Cillero-Pastor et al., *J. Proteome Res.* 2014, 13, 325-335. Briefly, the isobutyric acid/ammonium hydroxide mixture of the Caroff microextraction technique is sprayed onto tissue sections followed by humidified incubation at 100° C. to allow for hydrolysis of the acid-labile lipid A-KDO sugar linkage. Following methanol washes of the tissue we then prepare for MALDI-MSI as described above with norharmane matrix in a chloroform-based solvent. Once empirically optimized, the method will be automated on a SunCollect sprayer device (SunChrom) to improve reproducibility and reduce variability.

This work will produce a list of hypothetical structures of lipid A molecules from hundreds of select species of bacteria from our collaborators which will be confirmed by tandem MS. Confident structural assignments will be aided by HCD tandem MS in the Orbitrap after IMS separation. The detectable dynamic range will be further extended by a novel combination of mass/charge and ion mobility selected tandem MS. The existing Cartesian MS1 product library will be extended to include odd chain fatty acids and all other modifications noted in the published literature of lipid A structures and from our own work herein, as well as developed for use with tandem MS data.

Example 10

Evaluate Efficacy, Safety, PK, and SAR of Lead ASLA Therapeutics in Rodent Models of Gram-Negative Sepsis Based on the in vitro findings, we will identify up to five lead ASLA molecules per year for efficacy testing in rodent models of Gram-negative sepsis. Remick et al., *Shock* 2000, 13, 110; Buras et al., *Nat Rev Drug Discov* 2005, 4, 854-865. First, the candidate molecules will be tested for protection against hypercytokinemia and onset of clinical presentation of sepsis using a lethal model of endotoxemia. Briefly, endotoxemia will be induced in mice using a highly stimulatory Ec-derived LPS with or without an ASLA molecule given either simultaneously or post-induction. In this model, we have demonstrated that ASLA molecules result in increased survival when the ALSA molecule is administered both simultaneously and therapeutically up to 12 hours post LPS administration (FIG. 4). Having established therapeutic dose ranges for the lead ASLA molecules, we will evaluate efficacy in a lethal infection model of Gram-negative sepsis (intravenous inoculation) and in a cecal ligation and puncture (CLP) model of polymicrobial sepsis. Candidate molecules resulting in improved clinical scores, increased survival, and decreased markers of systemic inflammation will be advanced for safety and pharmacokinetic (PK) evaluation. Peak serum profile, clearance rate, and a general safety evaluation will be established for up to five lead ASLA candidates per year.

Experimental Design

Characterize protective profile of lead ASLA molecules using a lethal endotoxemia model. A cohort of candidate ASLA molecules identified in Example 8 will be evaluated for protection against lethal endotoxemia in mice induced with a bolus of pro-inflammatory LPS and either co-administering or therapeutically treating with the candidate ASLA molecule, as shown in preliminary data (FIG. 4). We have demonstrated using this model that treatment with our ASLA molecules results in increased survival, with successful treatment extended out as far as 12 hours post induction. Using this model as a preliminary in vivo screening tool, we will test the most competitive ASLA molecules (in vitro) from Example 8. Briefly, five mice per group will be dosed i.p. as follows: 1) positive control—Ec LPS (25 mg/kg), 2) competitive inhibition—ASLA molecule (10 mg/kg) & Ec LPS (25 mg/kg), 3) therapeutic treatment—Ec LPS (25 mg/kg) then ASLA molecule (10 mg/kg) either 4, 8 or 12 hours post Ec LPS injection, and 4) toxicity control—ASLA molecule (10 mg/kg). We will monitor these animals and assign clinical scores every twelve hours post-administration. LPS administration induces temperature dysregulation (hypothermia) in mice and pro-inflammatory cytokine accumulation, which will be recorded by core body temperature every 24 hours post-administration using implantable miniature telemetry probes, such as PhysioTel Hybrid Digital (HD) Implants or digital rectal thermometers. At peak of clinical symptoms, 24 hours post-induction, we will collect blood from the lateral saphenous vein for serum preparation and determination of cytokine profiles. Serum levels of IL-6, TNF-α, and the acute phase molecule C-reactive protein (CRP) will be measured using a custom multiplex cytokine panel (fee-for-service, UMB Cytokine Core Facility). Pierrakos et al., *Journal of Clinical Invest.*2003, 112, 460-467. To account for biological variables, we will perform each study with an n=5 for each group at least twice in both genders. We will evaluate efficacy of the ASLA molecules based on their ability to reduce serum cytokines/proteins, indicating a competitive reduction in the pro-inflammatory effect of Ec LPS.

Evaluate efficacy of lead ASLA molecules in infection dissemination and poly-microbial models of Gram-negative sepsis. ASLA candidate molecules that have been shown to improve clinical scores in the endotoxemia model will be used for treatment of mice that are septic due to an active Gram-negative infection. Briefly, five mice per group will be treated via i.v. administration: 1) positive control—*E. coli* (up to $10^5$ CFU); antibiotic treated-ceftriaxone (20 mg/kg) injected i.p. 8 hours after *E. coli* (up to $10^5$ CFU); 2) competitive inhibition—ASLA molecule (10 mg/kg) injected 8 hours after *E. coli* (up to $10^5$ CFU); and 3) co-treatment-ceftriaxone (20 mg/kg) and ASLA molecule (10 mg/kg) injected 8 hours after *E. coli* (up to $10^5$ CFU). Mice will be monitored and clinical scores recorded at least twice daily until death or complete recovery. Blood samples will be harvested from the lateral saphenous vein for quantification of circulating bacteria and evaluation of cytokine levels as described in this example. Statistical significance will be determined using GraphPad Prism 5 for independent challenges using the Mann-Whitney test and for co-challenges using the Wilcoxon signed-rank test (with a hypothetical value of 0) on log-transformed CI values. Upon reaching a clinical score of 4 (inactive and unresponsive, weak or ataxic—approximately 48-60 hours), mice will be euthanized and organs (spleen and liver) harvested for MS analysis in Example 9 and 11. Buras et al., *Nat Rev Drug Discov* 2005, 4, 854-865; Deng et al., *Journal of Infectious Diseases* 2015, jiv562; Lima et al., *PLoS ONE* 2015, 10, e0132336. In addition, H&E staining will be performed and blinded histological assessments will be made by a clinical pathologist. Blood will also be taken from these animals by cardiac puncture from which PBMC will be isolated and, using flow cytometry (LSRII, UMB FlowCORE), evaluated for percentage of circulating macrophages, neutrophils, T-cells and B-cells. This additional data about the systemic inflammation will complement the serum cytokine data collected in this Example.

Simultaneously, a CLP model of polymicrobial sepsis will be carried out with lead ASLA molecules. Instead of initiating infection intravenously, the cecum is ligated below the ileocecal valve allowing for incomplete obstruction of the digestive tract. The cecum is then punctured with a sterile needle, which allows for digestive material, including resident intestinal bacteria to leak out into the peritoneum. The treatment groups (five mice per group) will be used in this polymicrobial sepsis model as described in the Ec intravenous infection model. Identical monitoring, sample collection, and statistical analysis will be performed as described above. This Example seeks to confirm the anti-septic properties of lead ASLA molecules, and provide biological evidence/effective concentrations for pharmacokinetic studies that are outlined in this Example.

Characterize pharmacokinetics (PK) of ASLA molecules in vivo. We will evaluate the PK profiles of lead ASLA molecules in the Gram-negative sepsis model. Here, we will give the effective dose defined above for each of the three candidate molecules both with and without a blood infection. The objective of the PK studies is to determine tissue distribution and key PK parameters for each molecule (i.e., clearance, volume of distribution, $C_{max}$, AUC and half-life). These PK parameters will be used 1) to estimate the time needed to reach steady-state plasma concentrations of each molecule and 2) to simulate plasma concentration following different dosing scenarios to help design better PK/PD studies. Also, these studies will help in ranking the molecules in terms of their PK characteristics and tissue/plasma concentration ratios. For each study, 30 C57BL/6 adult mice (males and females) will be pretreated with a single i.v. dose (effective dose defined above) through tail injection of a lead ASLA molecule. Mice (n=3/time point) will be euthanized at a pre-dose and at 5, 15, 30, 60, 120, 240, 360, 600, 720 min post dose. Blood and tissue samples will be analyzed using the MS methods described in the Examples. Pharmacokinetic data analysis. Destructive sampling data from the PK studies for each compound will be analyzed using both non-compartmental and compartmental analyses as previously described in detail by our group. Mason et al., *Journal of Pharmacology and Experimental Therapeutics* 2010, 333, 854-864; Teksin et al., *Eur J Pharm Biopharm* 2009, 72, 471-477.

We have characterized two ASLA molecules that meet our established preliminary criteria: competitive inhibition of MD2/TLR4 and reduction in clinical presentation of sepsis. These two molecules alone ensure there will be additional candidate molecules to test in these Examples. Our refined structures stemming from these Examples add to the range of potentially therapeutic molecules. Since we are screening these ASLA molecules in both mouse and human MD2/TLR4-expressing cells lines, we anticipate similar results in the respective mouse models. We also anticipate the ASLA molecules will protect from hypercytokinemia induced in a Gram-negative blood infection and will have an acceptable safety profile. Heavy reliance on preclinical mouse studies has been blamed, in part, for the failure of TLR4-targeted sepsis treatments due to structural differences in the receptor. Fink et al., *Nat Rev Drug Discov* 2014, 13, 741-758 To evaluate the efficacy of our ASLA molecules against the human MD2/TLR4 receptor complex, we can repeat the above screening with lead ASLA molecules in mice expressing the human MD2/TLR4 receptor. The human MD2/TLR4 receptor responds similarly to the mouse MD2/TLR4 receptor when stimulated by Ec LPS, however, hypoacylated LPS elicits a decreased pro-inflammatory response in humanized versus mouse MD2/TLR4 mice. Hajjar et al., *PLoS Pathog.* 2012, 8, e1002963. Upon use of TLR4 humanized mice, similar experiments described in Example 10 can be carried out. These structural differences will be an advantage for our ASLA molecules since we aim to reduce pro-inflammatory cytokine production using hypoacylated and other variants of lipid A and we expect that our molecules will be more effective in the humanized MD2/TLR4 model than in wild-type mouse in summary, this work will narrow our focus on three lead ASLA candidate molecules that are competitive inhibitors of MD2/TLR4 and reduce the pro-inflammatory cytokine load when co-administered in a mouse sepsis model.

Example 11

Figure 11:
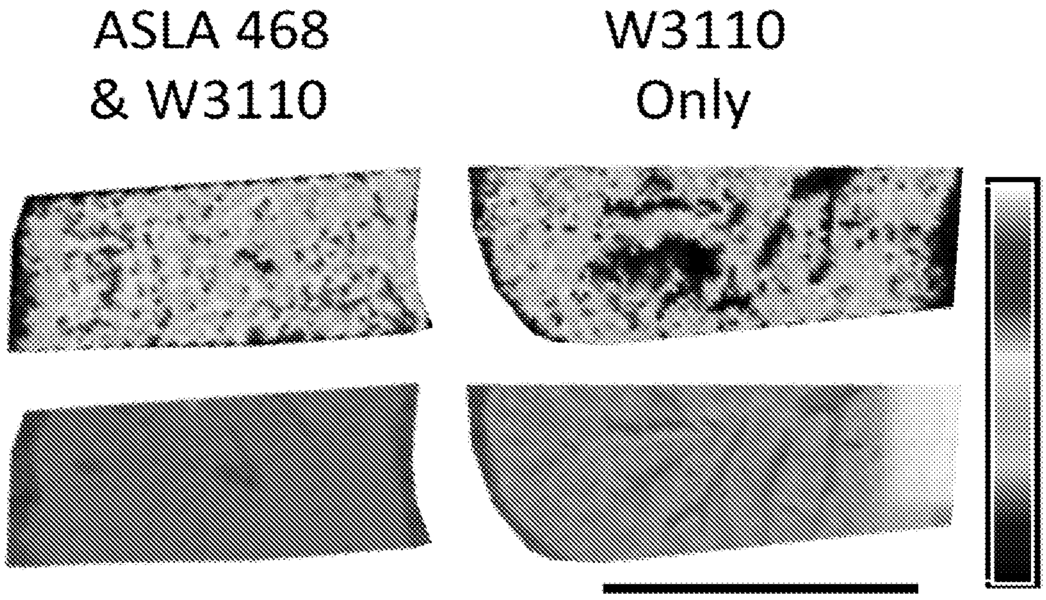
FIG. 11. Phosphatidylinositol (PI) lipid linked to immune infiltration detected at higher intensity in ASLA-treated liver. Approximately 15 $mm^2$ of upper lobe livers were analyzed (12 um thickness) using MALDI-MSI (100 um spatial resolution). Ion channel shown: m/z 887.7, negative, (+/−0.075%) putative identity: PI 38:3. Multicolor scale: arbitrary intensity; black: 0, white: 742. Black bar=5 mm. W3110=Ec LPS.
Figure 12A:
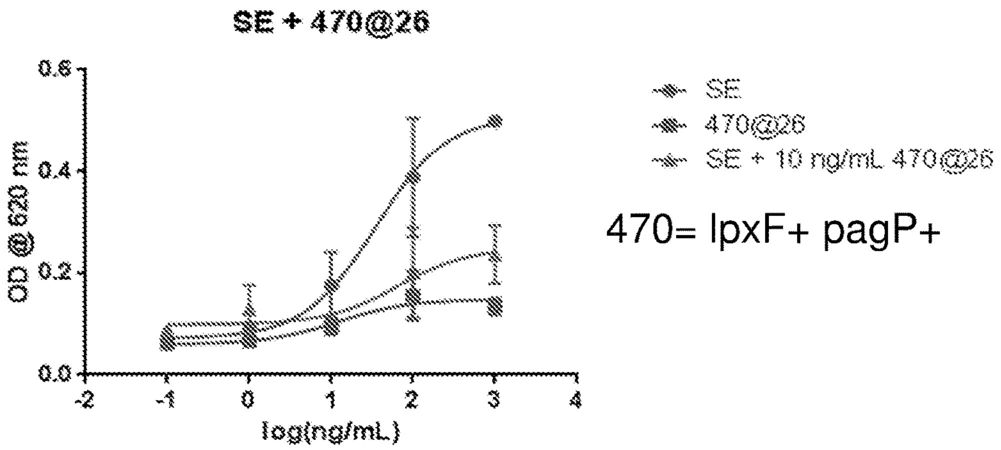
FIG. 12. Cell culture competitive inhibition of structurally similar molecules. Multiple BECC molecules (A-F), that were identified during initial screening as having a higher binding affinity than pro-inflammatory *Salmonella enterica* (SE) LPS, are capable of directly outcompeting SE LPS. This is demonstrated by in vitro cell culture reporter assays measuring activation of a transcription factor responsible for pathogenic inflammation.
Figure 12B:
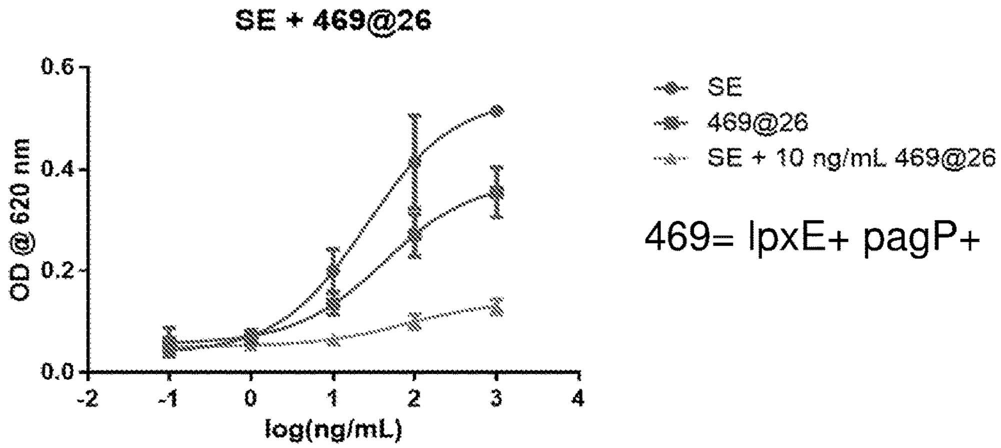
Figure 12C:
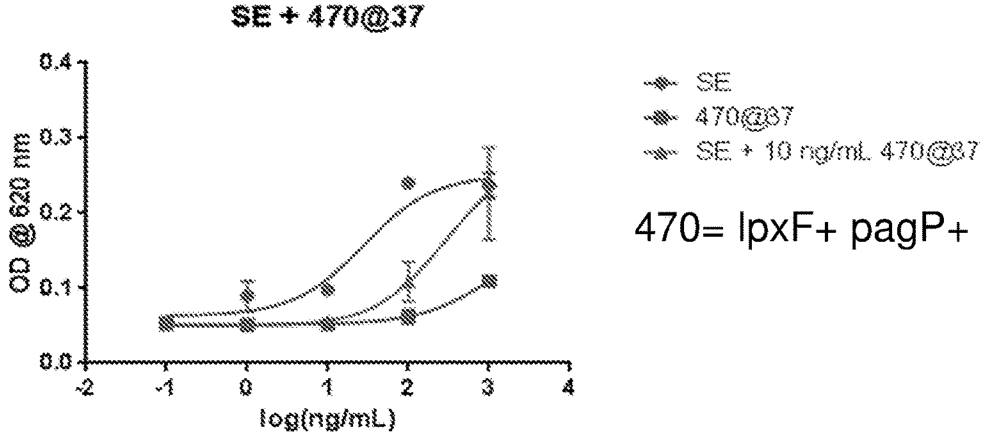

Investigate Distribution, Modification, and Persistence of ASLA Molecules In Vivo Engineer novel lipid A molecules for a unique opportunity to evaluate the systemic distribution, detoxification, and structural modification of lipid A—for both pro- and anti-inflammatory structures—in the presence of an immune response. Using MSI, we have demonstrated that lipid A can be mapped to discrete functional compartments of tissue; FIG. 5 demonstrates distribution of lipid A in the white pulp of mouse spleen. We will characterize the sub-histological distribution of both natural lipid A from a Gram-negative blood infection and the ASLA molecules identified in Example 8 as potential therapeutics. Additionally, lipid mapping of the host response will be performed as in FIG. 11, demonstrating increased intensity of a liver phospholipid specifically linked to monocytic infiltration during infection. Using the mass signature of these molecules that are unique to bacteria (or biosynthetic as per ASLA molecules), we will gain new insights into the response to sepsis. Immunohistochemical staining of serial sections imaged by MSI will help to define the cellular subsets that co-register with lipid A distribution. To ensure the accurate, unbiased identification of lipid A products on-tissue, authentic lipid A commercial standards will be used to validate fragmentation patterns on-tissue, controlling for tissue influences.

Use MALDI-MSI to map and quantify distribution and persistence of lipid A-based therapeutic molecules in a therapeutic timeline and as they are eliminated. Imaging of ASLA molecules will be done as follows. First, a lead ASLA molecule will be dosed in mice at the therapeutic range established in Example 9 followed by sacrifice and tissue collection at one, two, and three days post-administration. Next, we will collect liver, spleen, lung, and any other solid tissues of interest and prepare them for MSI, as we have previously described. Scott et al., *Health Phys* 2014, 106, 120-128. This includes snap-freezing tissue at a controlled rate, sectioning the unfixed, frozen tissue into 12 μm sections, thaw-mounting the sections to conductive glass slides, and spray-coating matrix (norharmane) in a chloroform-based solvent. The specific modifications necessary to image lipid A on-tissue were pioneered in the Ernst laboratory and are now common protocols. Finally, we will survey these tissues at 50-75 micron spatial resolution to localize ASLA therapeutics using MALDI-FT-ICR-MS. Subsequent structural analysis of these ASLA molecules will be performed according to methods described in these Examples.

Investigate structural modifications to native lipid A and ASLA during immune response and detoxification. Until recently, it has not been possible to identify lipid A structural alterations in vivo and only 'genetically locked' bacterial isolates from patients could be characterized for modification. However, now we can visualize different lipid A variants (FIG. 6), and map these structures within infected tissue. We will use this approach to identify potential modifications and potential detoxification to lipid A structures throughout the course of infection in a Gram-negative sepsis model with and without our characterized ASLA molecules. Tissues will be prepared from the height of clinical scores (n=4 each at 24 and 36 hours onset) as described above and imaged.

Example 12

Construction of Rationally-Designed LOS/Lipid A Structures with Engineered Lipid A Modifications Using Bacterial Enzymatic Combinatorial Chemistry (BECC)

An area of great interest is in the development of rationally-designed adjuvants based on molecules that stimulate the host innate immune system, specifically pattern-recognition receptors, including toll-like receptors (TLR). The objective of this aim is to custom synthesize LOS/lipid A molecules using heterologous expression of acyltransferases, glycosyltransferases, phosphatases, kinases, and modification of global regulatory genes required for lipid A biosynthesis with altered host innate immune responses.

Construction of additional rationally-designed LOS/lipid A structures with modified lipid A structures using bacterial enzymatic combinatorial chemistry (BECC) is encompassed in the disclosure. One can engineer modified LOS/lipid A molecules in an Yp background for determination of adjuvant potential using in vitro and in vivo assay systems. Briefly, one can heterologously express lipid A modifying enzymes in trans through bacterial conjugation or electroporation in a safe, attenuated BSL-2 Yp background (KIM6 or KIM10) to engineer unique lipid A structures (Donnenberg and Kaper, 1991; Rebeil et al., 2004; Jones et al., 2010) These Yp strain backgrounds were chosen as they produce a bisphosphorylated tetra-acylated lipid A structure (also known as lipidIVA) when grown at 37° C., thus allowing easy analysis of any resulting modification(s). As shown above, specific enzymes (PagP and MsbB) have been expressed in these Yp strain backgrounds to generate unique proof-of-concept lipid A structures. In addition, there are engineered strains that lack the two-component transcriptional regulator (PhoP) required for global lipid A modifications. These lipid A molecules are currently being evaluated for altered innate immune responses and adjuvant potential. These molecules are capable of inducing immune responses that can lead to either TH1 and/or TH17 responses. T helper responses are essential to the development of high affinity and long-term protective immunity. The specific T helper response can alter antibody isotype that can effect affinity, and avidity, as well as interactions with other immune cells required for pathogen clearance. To date, all previously reported BECC-derived molecules are bisphosphorylated (phosphate moieties at the 1 and 4' position). As has been shown for the AGP and MPL molecules, the presence of the phosphate moiety at the 1 position on the glucosamine backbone of lipid A plays an important role in host innate immune recognition. Therefore, one can focus on expressing enzymes that remove the terminal phosphate moieties in the strains that already have been generated by BECC. Two phosphatases have been identified in *Francisella novicida* that remove the 1 position (LpxE) and 4' position (LpxF) phosphatases (Wang et al., 2004; Wang et al., 2007) One can generate six additional bacterial mutants that express acyltransferases (LpxP, HtrB, LpxXL) and glycosyltransferases (addition of aminoarabinose and galactosamine) or deletions in other global regulators (PmrA/B) using plasmid constructs currently available in an enzyme expression library (Raetz et al., 2007).

Aspects of the disclosure provide analytical validation of LOS and lipid A isolated from BECC constructed strains. For initial screening, one can use two small-scale LOS extraction protocols that require small overnight cultures (~5 mls). These methods include a phenol-based (Yi and Hackett, 2000; Westphal and Juan, 1965) and an ammonium hydroxide/isobutyric acid-based (El Hamidi et al., 2005) protocol, which are repeatable and robust extraction techniques and standard methods in the Ernst laboratory. After extraction, lipid A is liberated from these LOS preparations using gentle hydrolysis, which preserves structural elements (e.g., phosphate groups and attached carbohydrate moieties) that are sensitive to harsh acid treatment (Caroff et al., 1988). One can use a variety of established mass spectrometric-based techniques, such as MALDI-TOF and ESI, to characterize the base structure of the lipid A in both the negative- and positive ion mode (Ernst et al., 2006). Large-scale LOS preparations are extracted using a hot phenol/water extraction method (Hajjar et al., 2006; Ernst et al., 2006; West et al., 1997; Ernst et al., 2007).

Subsequently, LOS are treated to ensure purity from contaminating nucleic acids and proteins (Fischer et al., 1983), extracted to remove contaminating phospholipids (Folch et al., 1957) and TLR2-agonist proteins (Hirschfeld et al., 2000), and when required, converted to lipid A by mild hydrolysis. These steps ensure the generation of preparations suitable for structural analysis and proinflammatory and adjuvanticity experiments proposed below. LOS/lipid A fatty acid content are measured by gas chromatography (GC) after acid hydrolysis, methylation, and hexane extraction (Guo et al., 1997; Somerville et al., 1996). The resultant MS and GC data is used to define the exact structure of individual molecules present in the isolated lipid A from the WT and BECC constructed strain.

Materials and Methods

BECC. To create novel, biologically expressed lipid A structures using bacterial enzymatic combinatorial chemistry (BECC), lipid A-modifying enzyme genes phoP, lpxP, msbB, lpxE, pagP, and/or lpxF were added to or deleted in *Y. pestis* strain KIM6+ in various combinations, described in Tables 1 and 2. *Y. pestis* KIM6+ expressing *Francisella novicida* LpxE (strain 467) was generated by bacterial conjugation with *E. coli* strain S17-1 λpir containing pWSK29-lpx$E_{Fn}$ and was selected using 100 μg/ml carbenicillin. Ingram et al., 2010. *Biochemistry* 49:8325-8337. The mutant was confirmed by mass spectrum analysis of lipid A. The ΔphoP (strain 44) and ΔmsbB ΔlpxP (strain 48) *Y. pestis* KIM6+ strains were generated previously. et al., 2004. *Mol Microbiol* 52:1363-1373; Rebeil et al., 2006. *J Bacteriol* 188:1381-1388. To generate the strain with repaired *Y. pestis* pagP (pag$P_{Yp}^{Rep}$), a PCR product containing *Y. pestis* pagP with a base substitution from A to G at position 653 was mutated and amplified by splicing by overhang extension PCR. Higuchi R et al., *Nucleic Acids Res* 16:7351-7367. The outer primers were designed to incorporate SacI and SmaI sites. The PCR product and the allelic exchange suicide plasmid pCVD442 (a gift from Michael Donnenberg and James Kaper, University of Maryland—Baltimore; Addgene plasmid no. 11074) were digested with corresponding enzymes, ligated, and transformed into the *E. coli* conjugation donor strain, S17-1 λpir. The pCVD442-pag$P_{Yp}^{Rep}$ plasmid was confirmed by sequencing and then mated to avirulent *Y. pestis* KIM6+. Donnenberg et al., 1991. *Infect Immun* 59:4310-4317. The merodiploids were selected on *Yersinia* selective agar base (YSAB) (catalog no. CM0653B; Remel, Inc.) supplemented with 100 μg/ml carbenicillin. The merodiploids were struck again for single-colony isolation. Single-colony isolates were grown overnight in brain heart infusion (BHI) broth, followed by plating on Congo red medium supplemented with 7.5% sucrose to select against sacB on the integrated plasmid. The sucrose-resistant colonies were then patched onto YSAB with and without carbenicillin, and sucrose-resistant, carbenicillin-sensitive colonies were isolated for sequencing to confirm the presence of the wild-type or repaired pagP.

*Y. pestis* KIM6+ pag$P_{Yp}^{Rep}$ expressing *Francisella novicida* LpxF (strain 470) was generated by bacterial conjugation with *E. coli* S17-1 λpir containing pWSK29-lpx$F_{Fn}$ and was selected by using 100 μg/ml carbenicillin. Ingram et al., 2010. *Biochemistry* 49:8325-8337. The mutant was confirmed by mass spectrum analysis of lipid A. The previously made ΔlpxP and ΔmsbB ΔlpxP strains were transformed with pCVD442-pag$P_{Yp}^{Rep}$ to generate the ΔlpxP ΔmsbB pag$P_{Yp}^{Rep}$ and ΔlpxP pag$P_{Yp}^{Rep}$ strains (strain 440 and strain 439, respectively). The mutants were confirmed by mass spectrum analysis of lipid A. The associated predicted structures were drawn using ChemDraw (PerkinElmer).

Bacterial growth and LOS extraction. *Y. pestis* strains, stored as glycerol stocks, were grown overnight on BHI agar at 37° C. A single colony was selected for overnight growth with shaking (220 rpm) at 26 or 37° C. in 10 ml of BHI supplemented with 1 mM $MgCl_2$. Ten milliliters of the overnight culture was then used to inoculate 1 liter of BHI with 1 mM $MgCl_2$ prewarmed to either 26 or 37° C. and grown to stationary culture under the same conditions for 18 to 24 h. *E. coli* strain W3110 was grown similarly but only at 37° C. and in lysogenic broth supplemented with 1 mM $MgCl_2$. The bacteria were pelleted, lyophilized, and stored at room temperature until extraction. A proteinase K-digested hot phenol extraction was performed to isolate lipooligosaccharide (LOS). Apicella M A. 2008. *Methods Mol Biol* 431:3-13. Briefly, 500 mg of lyophilized bacterial pellet was solubilized in a 10 mM Tris-Cl buffer, pH 8.0, with 2% sodium dodecyl sulfate (SDS), 4% (mercaptoethanol, 20 mg/ml proteinase K, and 2 mM $MgCl_2$ at 65° C. for 1 h with intermittent vortexing and further digested overnight at 37° C. The samples were precipitated overnight at 20° C. with the addition of sodium acetate to a final concentration of 0.1 M and cold ethanol to 75%. LOS was pelleted, and the precipitation was repeated 2 more times to remove residual SDS and peptides. The samples were then suspended in a 10 mM Tris-Cl buffer, pH 7.4, and digested for 4 h at 37° C. with 100 μg/ml DNase and 25 μg/ml RNase. An equal volume of 90% phenol was added, and the sample incubated at 65° C. for 15 min with occasional vortexing. The sample was cooled in ice-water and centrifuged, and the aqueous fraction was collected. The phenol layer was reextracted with an equal volume of endotoxin-free water. The aqueous layers were pooled and dialyzed in a 1-kDa molecular-mass-cutoff dialysis bag with repeated water changes at 4° C. to remove phenol over 48 h. The samples were then frozen on dry ice and lyophilized. Dry samples were washed four times with 2:1 (vol/vol) chloroform-methanol to remove contaminating hydrophilic lipids and reextracted using the Hirschfeld et al. procedure to remove contaminating lipoproteins. Hirschfeld et al., *J Immunol* 165:618-622. Samples were then lyophilized and stored sealed at room temperature.

Mild acid hydrolysis and mass spectrometry analysis. LOS was dissolved in 10 mM sodium acetate (Sigma), pH 4.5, to a concentration of 5 to 10 mg/ml and vortexed. Rosner M R, Tang J, Barzilay I, Khorana H G. 1979. Structure of the lipopolysaccharide from an *Escherichia coli* heptose-less mutant. I. Chemical degradations and identification of products. *J Biol Chem* 254:5906-5917. This mixture was heated to 100° C. for 2 h, cooled on ice, frozen, and lyophilized overnight. The mixture was then washed to remove core sugars and excess salts with the following procedure. Lyophilized samples were suspended in 170 μl of endotoxin-free, cell culture-grade water per 5 to 10 mg of starting LOS, followed by 850 μl of 20 mM HCl in 95% ethanol. Samples were vortexed and centrifuged at 5,000×g for 5 min and then washed in 1 ml of 95% ethanol, followed by centrifugation at 5,000×g for 5 min. These two wash steps were repeated for a total of three times to remove the hydrolyzed core sugars and salt. Samples were suspended in endotoxin-free water and lyophilized in a previously tared tube to determine yield. Lipid A was solubilized in a 12:6:1 (vol/vol/vol) solution of chloroform-methanol-water and mixed with an equal volume of 20-μg/ml norharmane in 2:1 (vol/vol) chloroform-methanol. One microliter of this mixture was spotted onto a stainless steel target plate. Spectra were gathered in negative mode on a Bruker Microflex matrix-assisted laser desorption ionization-time of flight (MALDI-TOF) mass spectrometry instrument calibrated to an external peptide standard.

Example 13

Cell Culture Competitive Inhibition of Structurally Similar Molecules

Experimental Setup: Reporter cell line THP-1 Duals (Invitrogen) are incubated for 18 hours over a five-log dose range with either *Salmonella enterica* (Se) LPS alone, BECC molecule alone (467@26, 468@26, 468@37, 469@26, 470@26, 470@37), or increasing doses of Se with a constant dose of BECC molecule (10 ng/mL). THP-1 Dual cells have a SEAP reporter under the NFκB promoter that is easily quantified in the supernatant of cultured cells. After 18 hours of culture supernatant is removed from the cell culture and SEAP is quantified to indicate the level of NFκB activation/inflammation. OD@620 nm can be directly extrapolated to represent relative amounts of NFκB activation. The line of best fit for each data set is calculated using a non-linear log(inhibitor) vs. response three parameter analysis. Mean±SD of duplicate samples is graphed for each data point.

Results/Discussion: The IC50 (inflection point on the regression line) indicates the concentration at which 50% of the maximal signal is reached. When 10 ng/mL of BECC molecule is co-incubated with increasing concentrations of pro-inflammatory Se LPS the IC50 is shifted up as much as 2.5 logs. A decrease in maximal signaling is also observed upon incubation with BECC molecules. These observations, taken together, suggest that BECC molecules are outcompeting pro-inflammatory LPS. We are also able to infer that anti-septic BECC molecules have a higher binding affinity for the known LPS receptor (TLR4) than Se LPS.

Multiple BECC molecules, that were identified during this initial in vitro screening as having a higher binding affinity than pro-inflammatory *Salmonella enterica* (SE) LPS, are capable of directly outcompeting SE LPS. This is demonstrated by in vitro cell culture reporter assays measuring activation of a transcription factor responsible for pathogenic inflammation. See FIG. 12A-F.

Example 14

In Vivo Non-Lethal LPS Septic Shock Mouse Model

Experimental Setup: In this in vivo model of non-lethal septic shock 6-week old C57BL6 mice were injected intraperitoneally with either 10 mg/kg *E. coli* (W3110) LPS, 10 mg/kg Ec LPS+10 mg/kg BECC468@26, 10 mg/kg Ec LPS+5 mg/kg BECC468@26, 10 mg/kg Ec LPS+1 mg/kg BECC468@26, or 10 mg/kg BECC468@26 alone. Clinical scores, according to description on slide 2, were made for each mouse 12, 24, 36, and 48 hours post-injection. A mean±SD is graphed for each group at each timepoint.

Results/Discussion: A peak clinical score is observed for all groups 24 hours post-injection with the Ec LPS alone group most affected. The peak clinical score is decreased in a dose dependent manner by co-administration of BECC468@26 with Ec LPS. These results provide in vivo data to support our original hypothesis that BECC molecules are able to compete with pro-inflammatory LPS and decrease inflammation/pathology associated with endotoxic shock.

Figure 13:
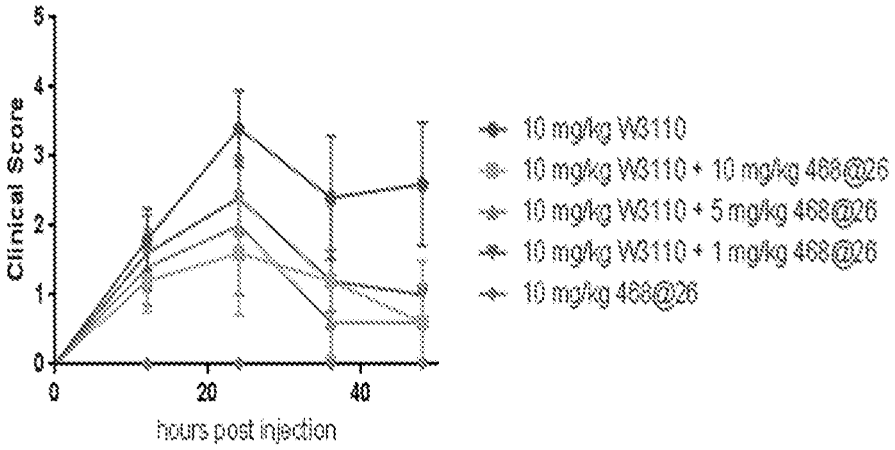
FIG. 13. In vivo non-lethal LPS septic shock mouse model. In an in vivo mouse model of non-lethal LPS septic shock, as compared to treatment with pro-inflammatory LPS alone, co-treatment with BECC molecules and pro-inflammatory LPS results in dampened pathogenic immune responses. This decrease in clinical symptoms afforded by treatment with the BECC molecule trends towards being dose dependent. W3110 is an *E. coli* strain that has pathogenically inflammatory LPS; C57BL6 mice, n=4 per group.

In an in vivo mouse model of non-lethal LPS septic shock we find that, as compared to treatment with pro-inflammatory LPS alone, co-treatment with BECC molecules and pro-inflammatory LPS results in dampened pathogenic immune responses. This decrease in clinical symptoms afforded by treatment with our BECC molecule trends towards being dose dependent. See FIG. 13.

Example 15

Lethal Endotoxemia, Survival

Experimental Setup: Similarly to the non-lethal endotoxic shock model, in this in vivo model of lethal septic shock 6-week old C57BL6 mice were injected intraperitoneally with either 25 mg/kg *E. coli* (W3110) LPS, co-administered 25 mg/kg Ec LPS+10 mg/kg BECC468@26, or 25 mg/kg Ec LPS followed by 10 mg/kg BECC468@26 four hours later. Mice were monitored for survival every 12 hours post-injection. n=6 mice for each group, percent survival for each group is graphed.

Results/Discussion: Mice that are co-administered a lethal dose of Ec LPS and 10 mg/kg BECC468@26 are able to be completely rescued, and even if the same treatment is administered 4 hours after the lethal dose, 66% of mice are rescued from lethality.

Using a mouse model of lethal endotoxemia we are able to save mice from death by septic shock. This can be done both prophylactically and therapeutically. See FIG. 4

Example 16

Cell Culture Competitive Inhibition of LPS from Multiple Gram Negative Bacteria Experimental Setup: Similarly to the in vitro co-culture experiment described for FIG. 12. Pro-inflammatory LPS from a variety of Gram negative bacteria are cultured over a 5-log dose range with a constant amount (100 ng/mL) of BECC468@26. After 18 hours of culture with THP-1 Dual cells, supernatant is removed from the cell culture and SEAP is quantified to indicate the level of NFκB activation/inflammation. OD@620 nm can be directly extrapolated to represent relative amounts of NFκB activation. The line of best fit for each data set is calculated using a non-linear log(inhibitor) vs. response three parameter analysis. Mean±SD of duplicate samples is graphed for each data point.

Results/Discussion: Again we observe that when 100 ng/mL of BECC molecule is co-incubated with increasing concentrations of pro-inflammatory Ec, *N. meningitidis*, or *K. pneumoniae* LPS the IC50 is shifted up and a decrease in maximal signaling is observed. These data suggest that BECC molecules are capable of outcompeting pro-inflammatory LPS. We are also able to infer that anti-septic BECC molecules have a higher binding affinity for the known LPS receptor (TLR4) than Se LPS.

Figure 14A:
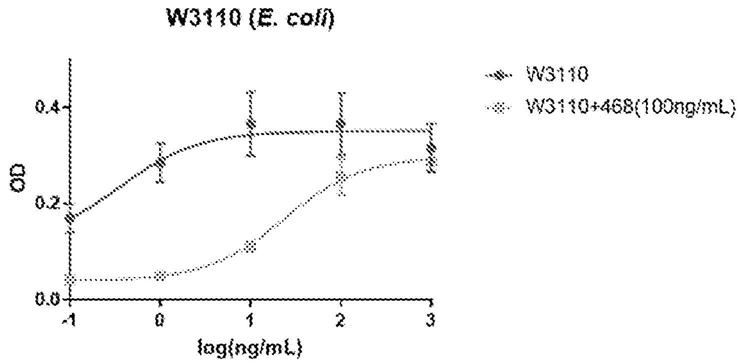
FIG. 14. Cell culture competitive inhibition of LPS from multiple gram negative bacteria. The BECC anti-septic molecules are also effective against a wide range of pathogenic pro-inflammatory LPS. This is demonstrated by in vitro cell culture competition assays. In addition to *Salmonella enterica*, anti-septic capabilities are shown against (A) *Escherichia coli*, (B) *Neisseria meningitidis*, and (C) *Klebsiella pneumoniae*.
Figure 14B:
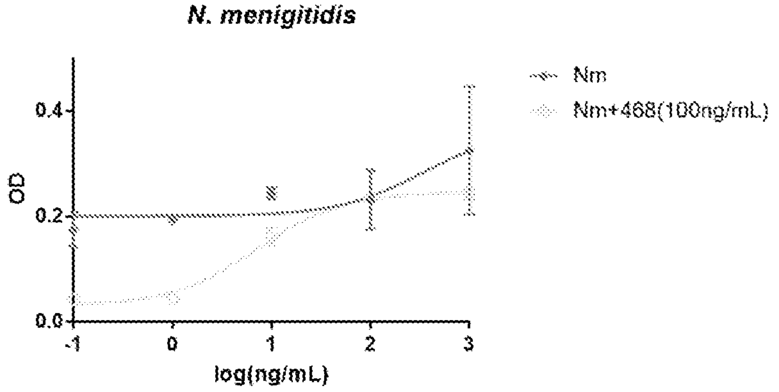
Figure 14C:
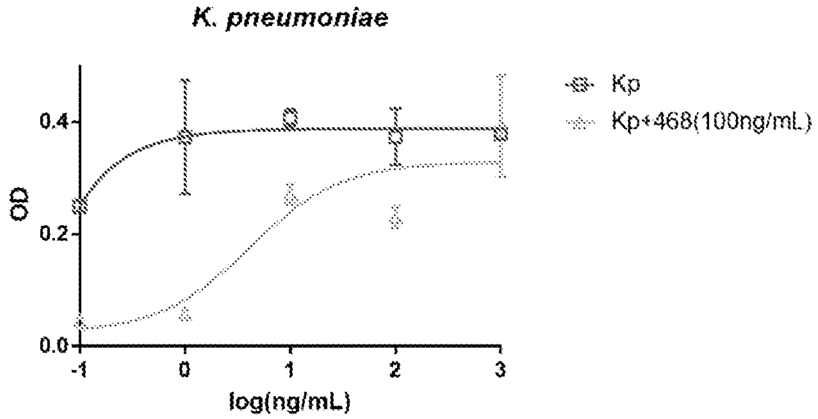
Figure 18A:
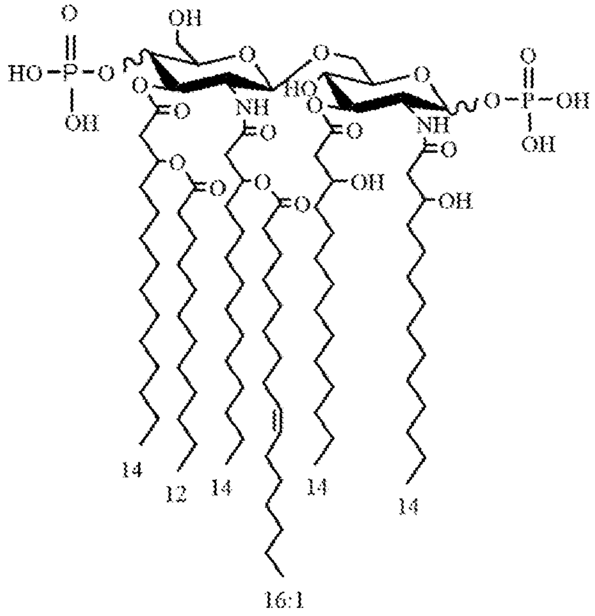
FIGS. 18A-B demonstrate the structures of exemplary LPS molecules generated by methods of the disclosure using an engineered *Y. pestis*.
Figure 18B:
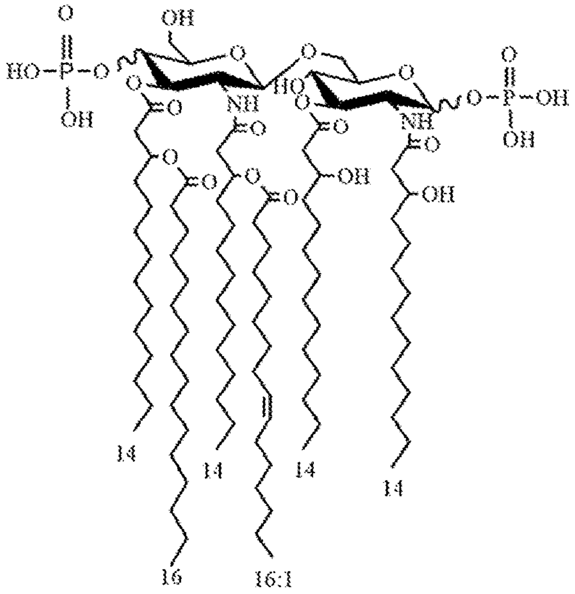
Figure 19A:
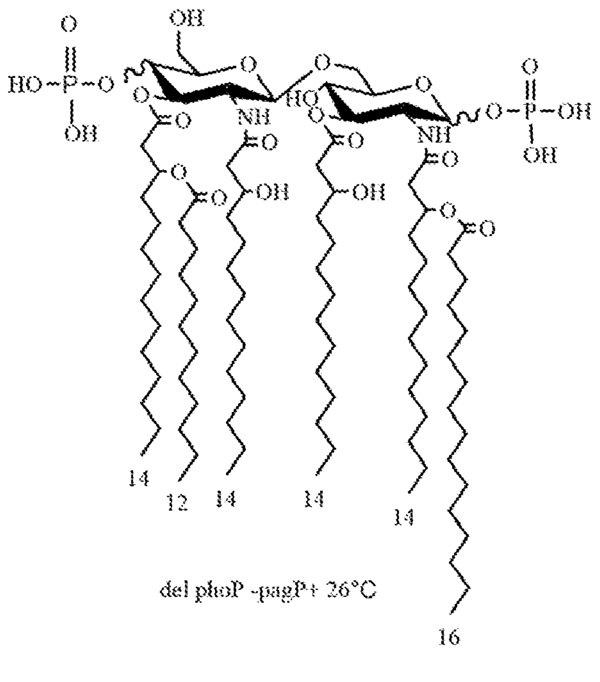
FIGS. 19A-D demonstrate the structures of exemplary LPS molecules generated by methods of the disclosure using an engineered *Y. pestis*.
Figure 19B:
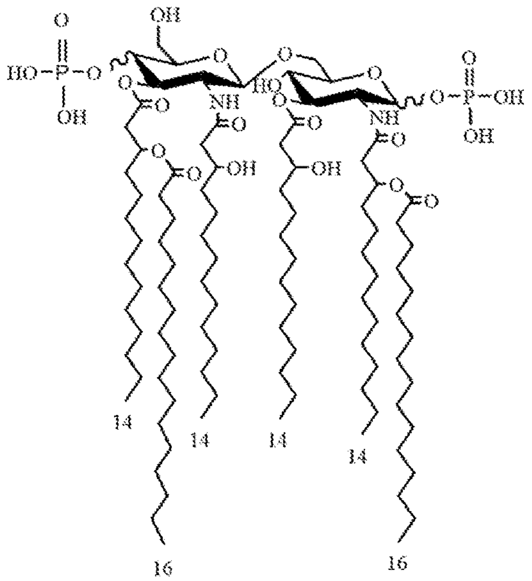
Figure 19C:
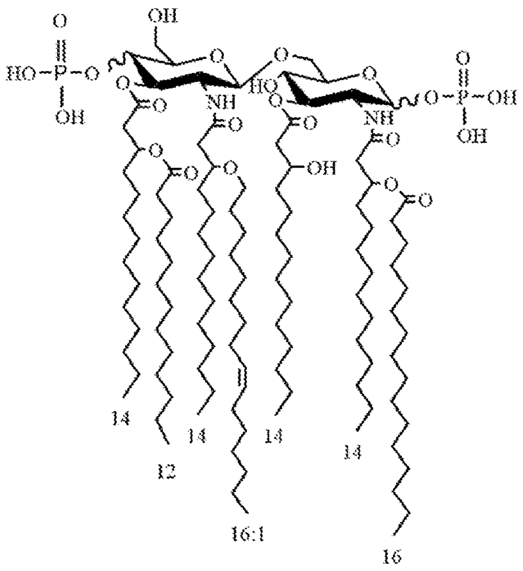
Figure 19D:
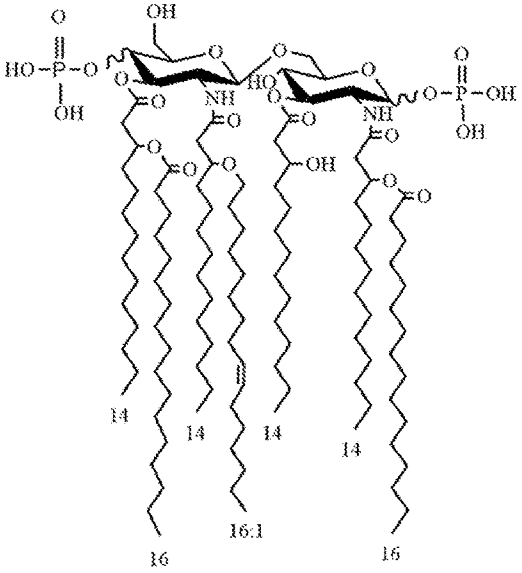
Figure 22:
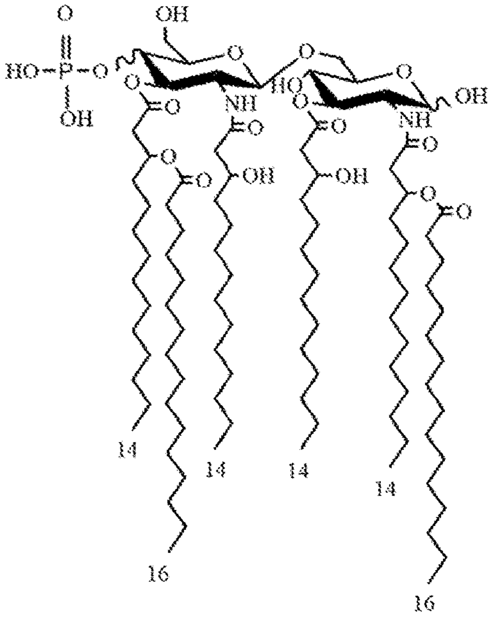
FIG. 22 demonstrates the structure of an exemplary LPS molecule generated by methods of the disclosure using an engineered *Y. pestis*.
Figure 23:
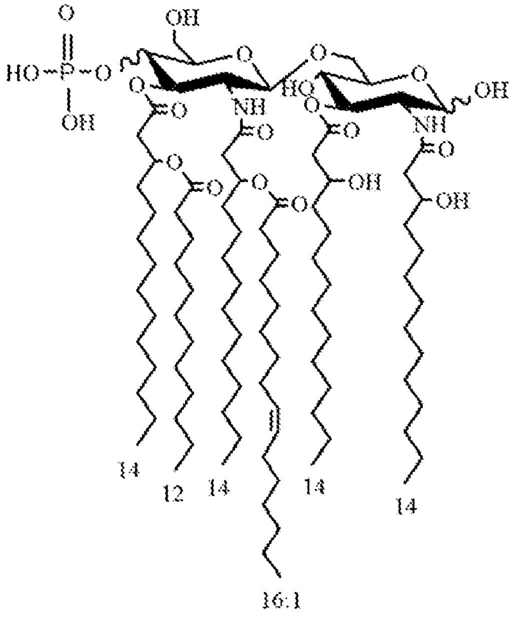
FIG. 23 demonstrates the structure of an exemplary LPS molecule generated by methods of the disclosure using an engineered *Y. pestis*.
Figure 24A:
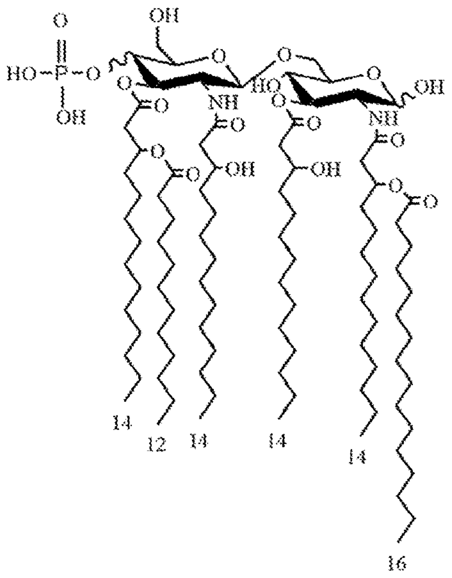
FIGS. 24A-D demonstrate the structures of exemplary LPS molecules generated by methods of the disclosure using an engineered *Y. pestis*.
Figure 24B:
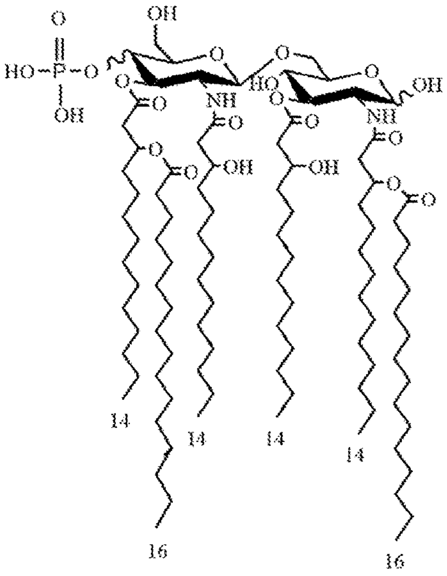
Figure 24C:
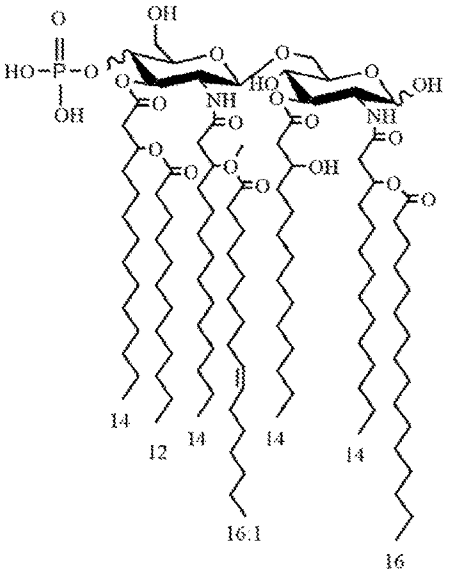
Figure 24D:
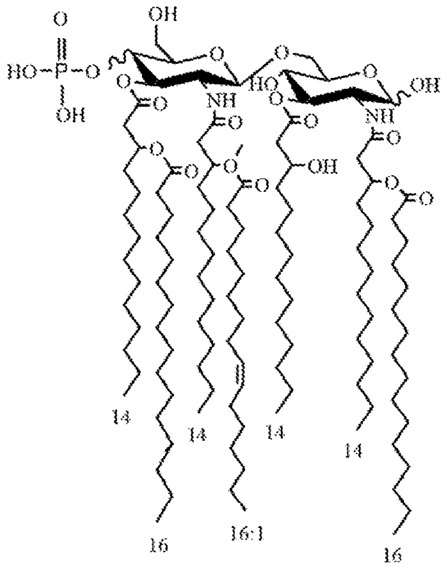

Our BECC anti-septic molecules are also effective against a wide range of pathogenic pro-inflammatory LPS. This is demonstrated by in vitro cell culture competition assays. In addition to *Salmonella enterica*, we now show anti-septic capabilities against *Escherichia coli, Neisseria meningitidis*, and *Klebsiella pneumoniae*. See FIG. 14A-C.

Example 17

Characterization of the Protective Profile of the Lead ASLA Molecules Using a Lethal Endotoxemia Model For all experiments, 6-8 weeks old male and female WT C57BL/6 mice (Jackson Laboratories) and male huMD2/TLR4 mice in the C57BL/6 background (breed in house) will be used. Only male mice can be used at the MD-2 gene integrated into the Y-chromosome.

A cohort of candidate ASLA molecules will be evaluated for protection against endotoxemia in mice by co-administering the ASLA molecule with a bolus of pro-inflammatory LPS, or therapeutically treating with the ASLA molecule. We have demonstrated using this model that our ASLA molecules successfully rescue lethally injected mice from death. Using this model as a preliminary in vivo screening tool, we will test the most competitive ASLA molecules (in vitro). Briefly, five mice per group will be dosed i.p. as follows: positive control—Ec LPS (25 mg/kg), competitive inhibition—ASLA molecule (10 mg/kg) & Ec LPS (25 mg/kg), therapeutic treatment—Ec LPS (25 mg/kg) then ASLA molecule (10 mg/kg) either 4, 8 or 12 hours post Ec LPS injection, and toxicity control—ASLA molecule (10 mg/kg). We will monitor these animals and assign clinical scores every twelve hours post-administration. LPS administration induces temperature dysregulation (hypothermia) in mice, coordinate with pro-inflammatory cytokine accumulation, therefore we will record core body temperatures every 24 hours post-administration using implantable miniature telemetry probes, such as PhysioTel Hybrid Digital (HD) Implants from DSI or digital rectal thermometer. Finally, at peak of clinical symptoms, 24 hours post-induction, we will collect venous blood from the lateral saphenous vein for serum preparation to evaluate the serum cytokine profile. Serum levels of IL-6, TNF-α, and the acute phase molecule C-reactive protein (CRP) will be measured using a custom multiplex cytokine panel (fee-for-service, UMB Cytokine Core Facility). We will evaluate efficacy of the ASLA molecules based on their ability to reduce serum IL-6, IL-8, TNF-α, and CRP, indicating a competitive reduction in the pro-inflammatory effect of Se LPS.

Evaluate efficacy of lead ASLA molecules in a dissemination model of Gram-negative sepsis. ASLA candidate molecules that have been shown to improve survival in the endotoxemia model will be used to treat mice that are septic due to an active Gram-negative infection. Briefly, five mice per group will be treated in the following manner via intravenous administration: positive control—*E. coli* (up to $10^5$ CFU); antibiotic treated-ceftriaxone (20 mg/kg) injected i.p. 8 hours after *E. coli* (up to $10^5$ CFU); competitive inhibition—ASLA molecule (10 mg/kg) injected 8 hours after *E. coli* (up to $10^5$ CFU); and co-treatment-ceftriaxone (20 mg/kg) and ASLA molecule (10 mg/kg) injected 8 hours after *E. coli* (up to $10^5$ CFU). Mice will be monitored and clinical scores recorded at least twice daily until death or complete recovery occurred. Blood samples will harvested from the tail vein for quantification of circulating bacteria and evaluation of cytokine levels. Statistical significance will be determined using GraphPad Prism 5 for independent challenges using the Mann-Whitney test and for co-challenges using the Wilcoxon signed-rank test (with a hypothetical value of 0) on log-transformed CI values. Upon reaching a clinical score of 4 (approximately 48-60 hours), mice will be euthanized and organs (spleen and liver) harvested for mass spectrometric analysis. In summary, this example seeks to confirm the anti-septic properties of our three lead ASLA molecules, and provide biological evidence/effective concentrations for future pharmacokinetic studies.

Evaluate efficacy of lead ASLA molecules in a polymicrobial cecal ligation and puncture (CLP) model. ASLA candidate molecules that have been shown to improve survival in the endotoxemia model will, concurrently with the dissemination model of sepsis, be used to treat mice that are septic due to CLP induced polymicrobial sepsis. Briefly, in the CLP model, the cecum is ligated below the ileocecal valve allowing for incomplete obstruction of the digestive tract. The caecum is then punctured with a sterile needle, which allows for digestive material, including resident intestinal bacteria to leak out into the peritoneum. Five mice per group will be treated in the following manner via intravenous administration: positive control—CLP; antibiotic treated-ceftriaxone (20 mg/kg) injected i.p. 8 hours after CLP; competitive inhibition—ASLA molecule (10 mg/kg) injected 8 hours after CLP; and co-treatment-ceftriaxone (20 mg/kg) and ASLA molecule (10 mg/kg) injected 8 hours after CLP. Mice will be monitored and clinical scores recorded at least twice daily until death or complete recovery occurred. Blood samples will harvested from the tail vein for quantification of circulating bacteria and evaluation of cytokine levels. Statistical significance will be determined using GraphPad Prism 5 for independent challenges using the Mann-Whitney test and for co-challenges using the Wilcoxon signed-rank test (with a hypothetical value of 0) on log-transformed CI values. Upon reaching a clinical score of 4 (approximately 48-60 hours), mice will be euthanized and organs (spleen and liver) harvested for mass spectrometric analysis. In summary, this example seeks to confirm the anti-septic properties of our three lead ASLA molecules, and provide biological evidence/effective concentrations for future pharmacokinetic studies.

Characterize the pharmacokinetics (PK) of ASLA molecules in vivo. We will evaluate the PK of the three ASLA lead molecules in the Gram-negative sepsis model. Here, we will give the effective dose defined above for each of the three candidate molecules both with and without a blood infection. The objective of the PK studies is to determine tissue distribution and key PK parameters for each molecule (i.e., clearance, volume of distribution, Cmax, AUC and half-life). These PK parameters will be used 1) to estimate the time needed to reach steady state plasma concentration of each molecule and 2) to simulate plasma concentration following different dosing scenarios to help design better PK/PD studies. Also, these studies will help in ranking the molecules in terms of their PK characteristics and tissue/plasma conc. ratios. For each study, C57BL/6 adult mice (female, n=30) will be pretreated with a single i.v. dose (effective dose defined above) through tail injection of a lead ASLA molecule. Mice (n=3/time point) will be euthanized at a pre-dose and at 5, 15, 30, 60, 120, 240, 360, 600, 720 min post dose. Blood and tissue samples will be analyzed using the mass spectrometric methods described in Aims 3 and 4. Pharmacokinetic data analysis. The destructive sampling data from the PK studies for each compound will be analyzed using both non-compartmental and compartmental analyses as previously reported by our group. Compartmental modeling will be used to estimate various pharmacokinetic parameters using Phoenix platform (ver. 1.3, Pharsight, Sunnyvale, Calif.). Several compartmental models will be evaluated to determine the best fit model. A variety of weighting schemes will be analyzed including equal weight, 1/y, 1/y^, 1/y2, and 1/y^2, where y is the observed drug conc., and y^ is the model-predicted drug conc. The final model will be selected based on goodness-of-fit plots, weighted residual sum of squares, random distribution of residuals, precision of parameter estimates, Akaike's information criteria, and Schwarz criteria. In addition, simulation analysis of different dosing scenarios will be conducted using Phoenix platform.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

What is claimed is:

1. A compound having a formula selected from the group consisting of:

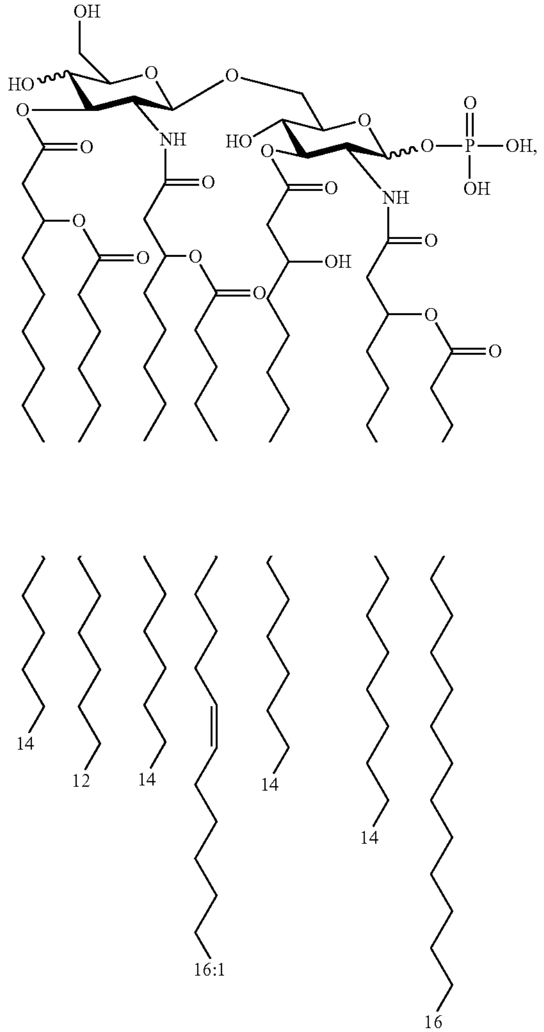

-continued

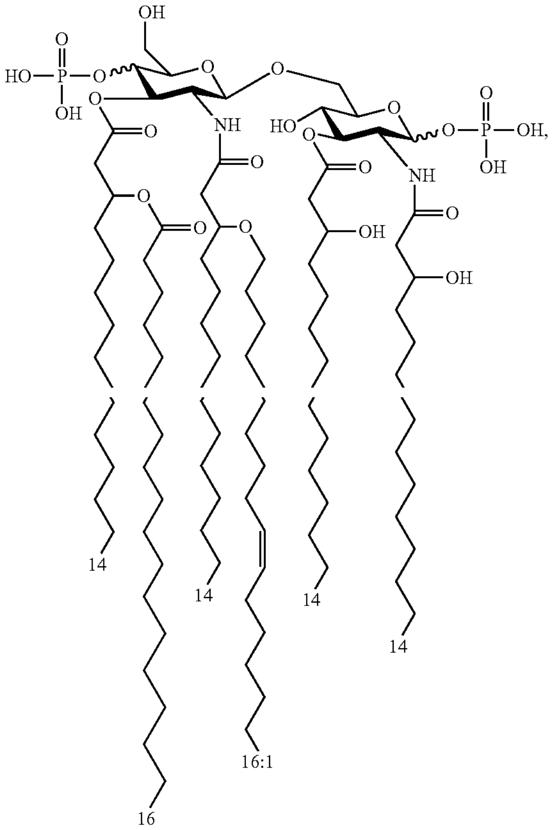

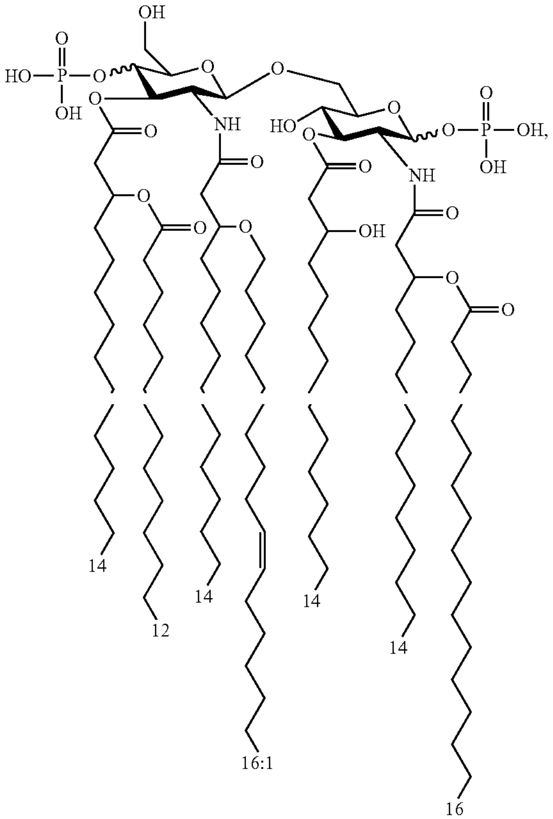

-continued
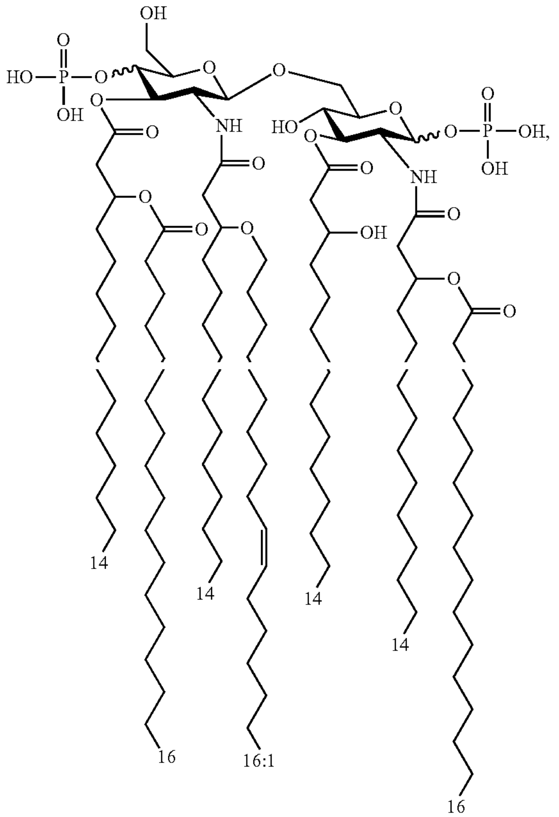
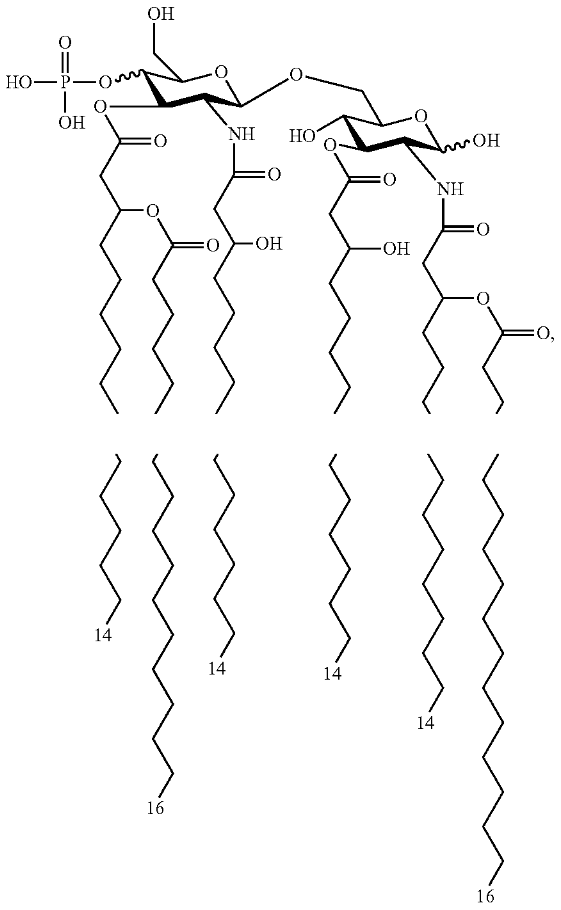
-continued
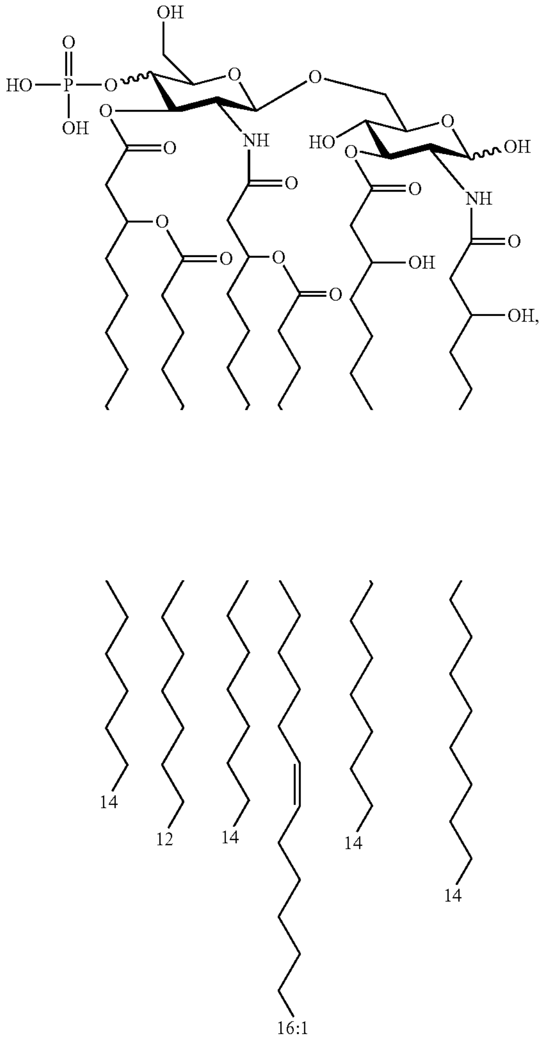
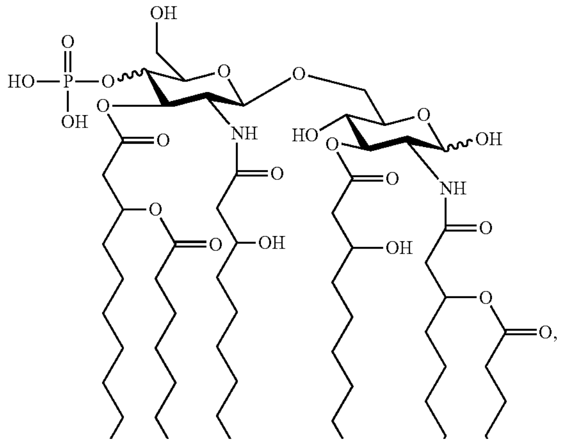

-continued
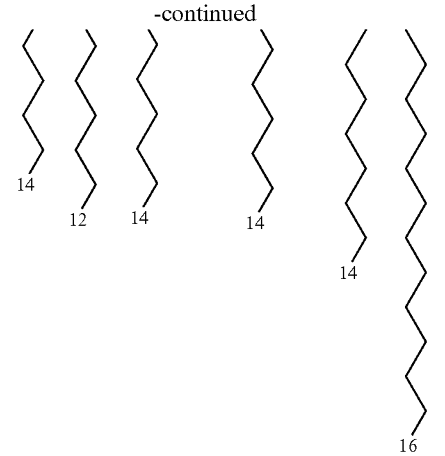
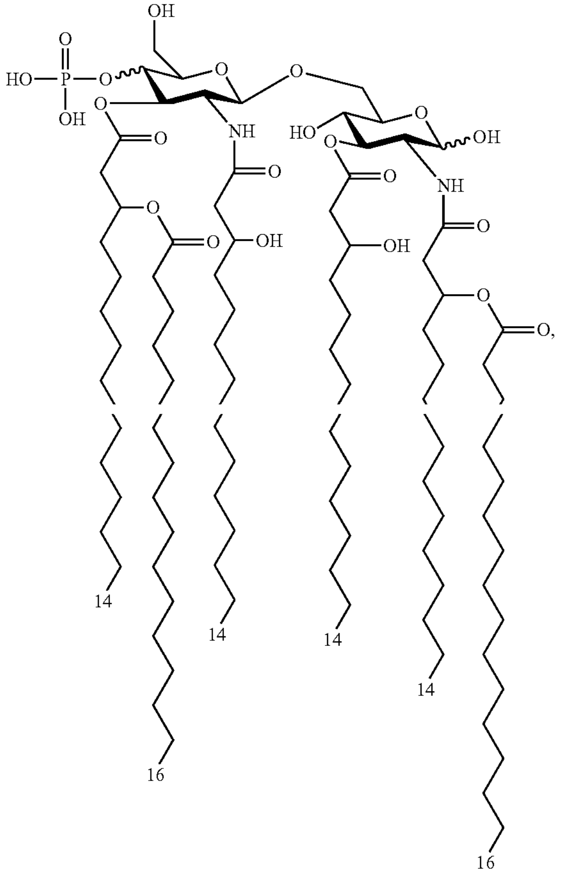
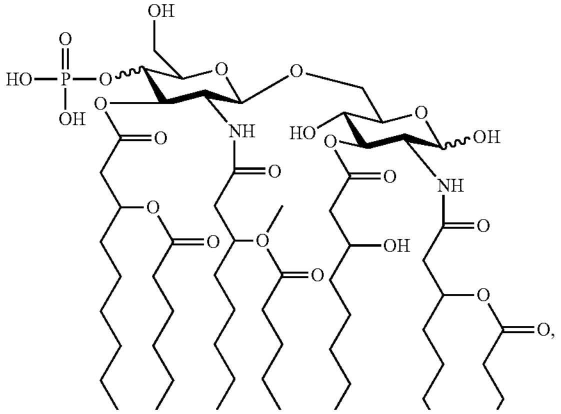
-continued
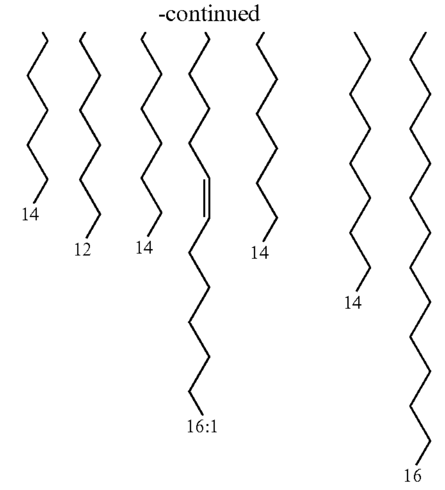
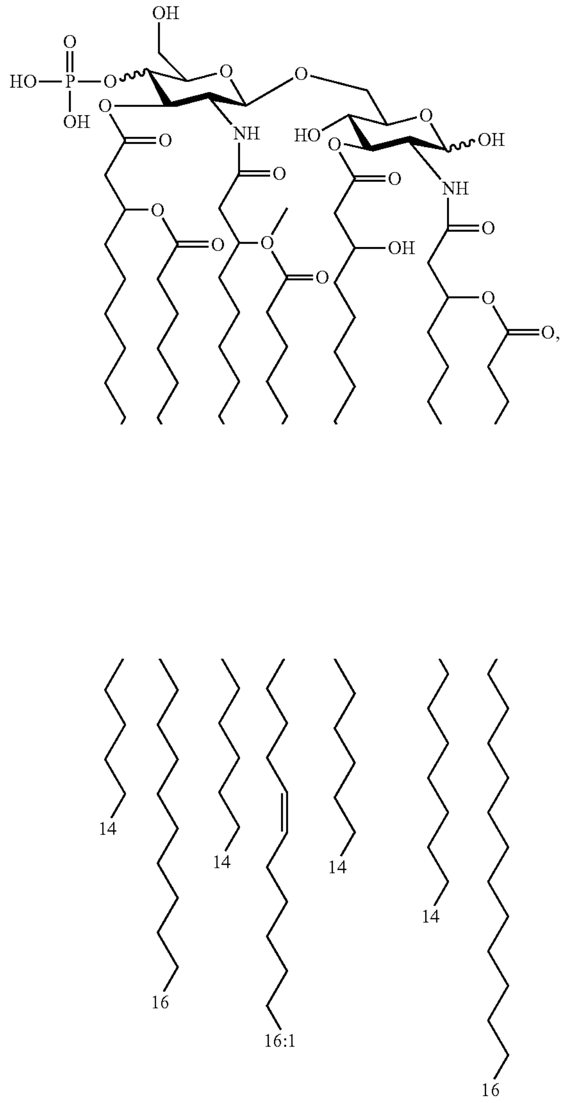

-continued
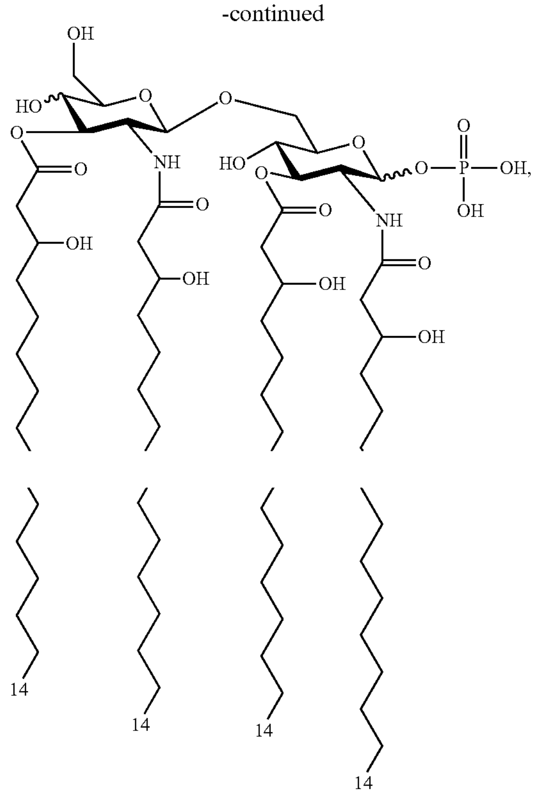
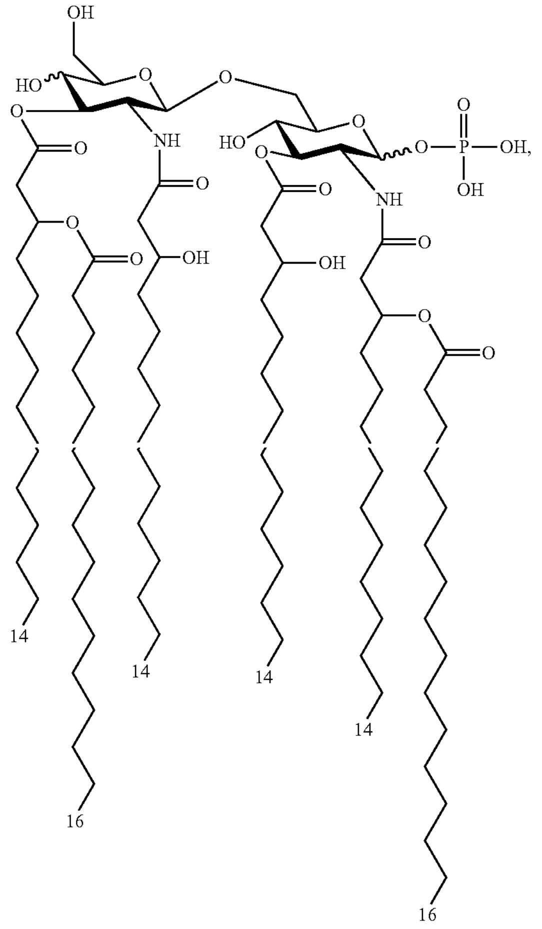
-continued
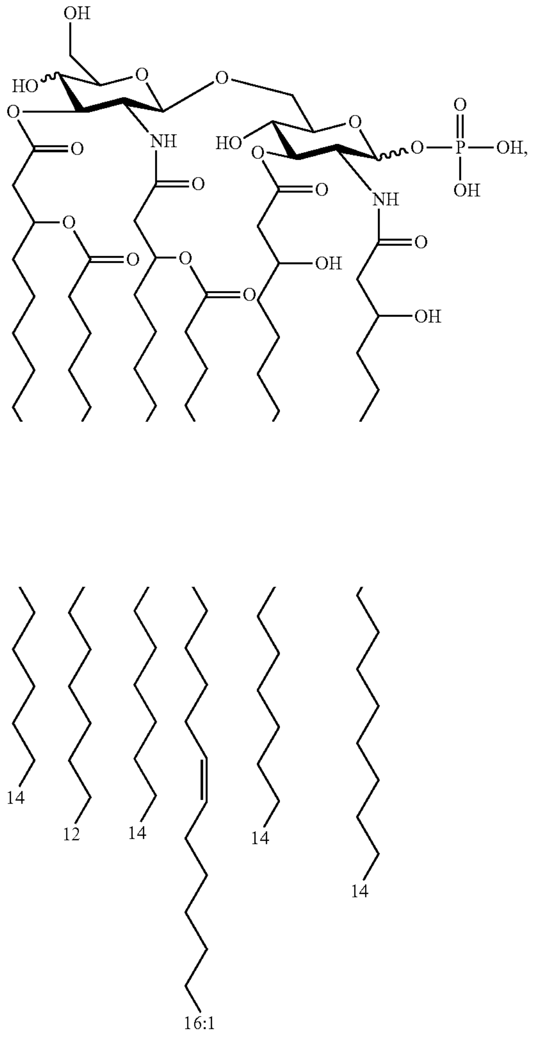
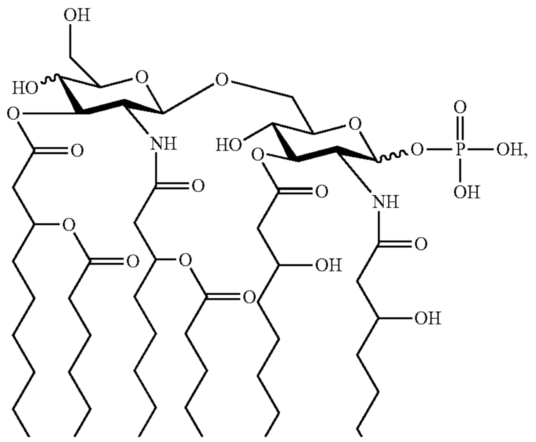

-continued
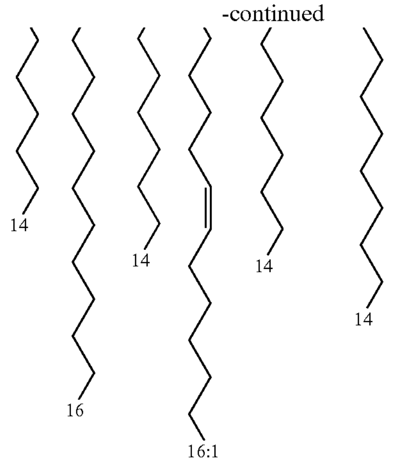
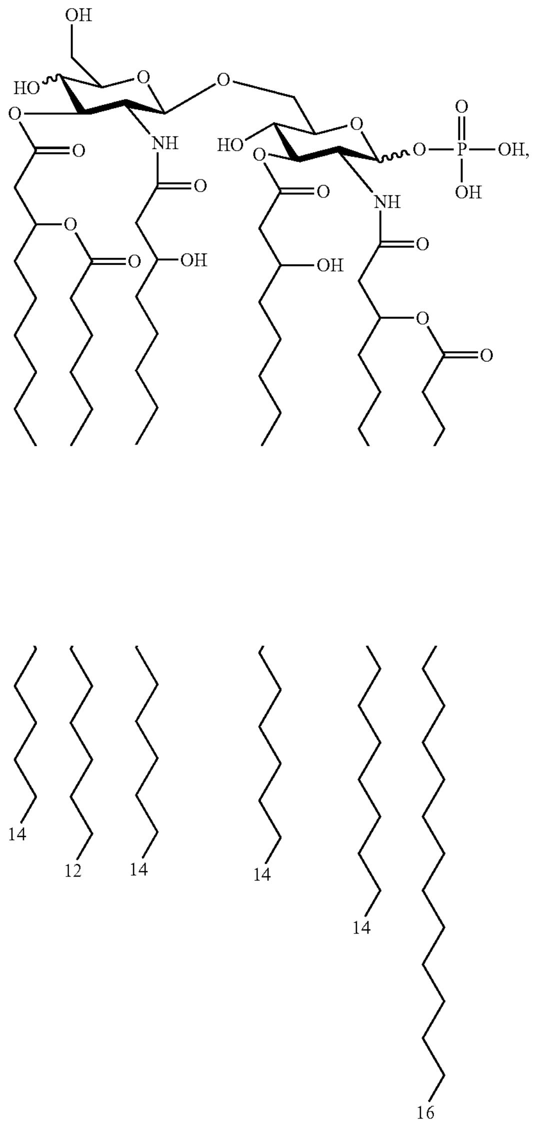
-continued
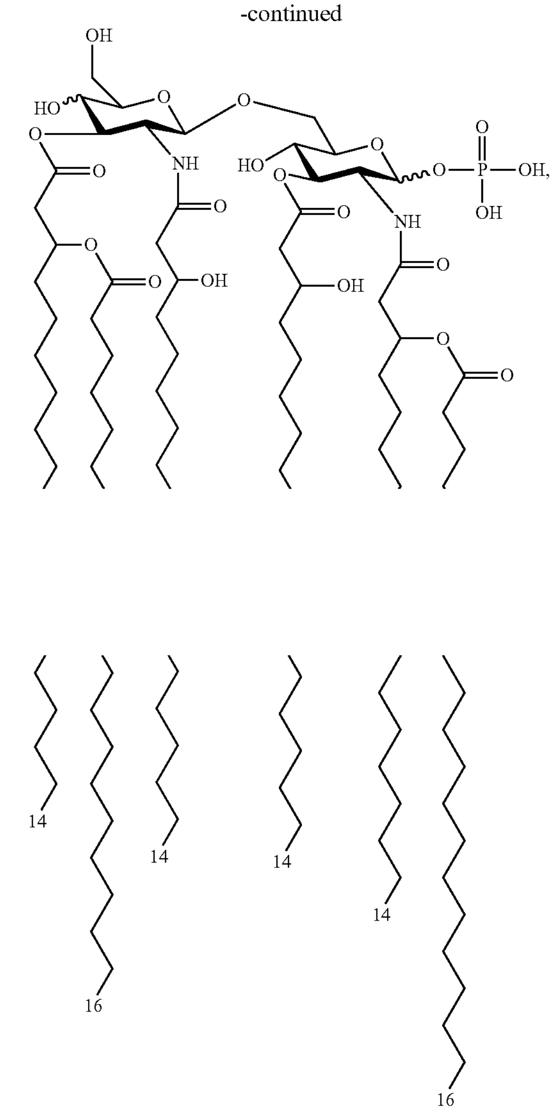
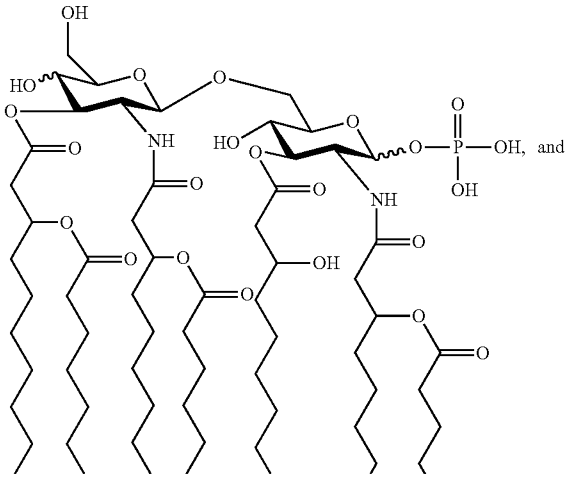
and

-continued
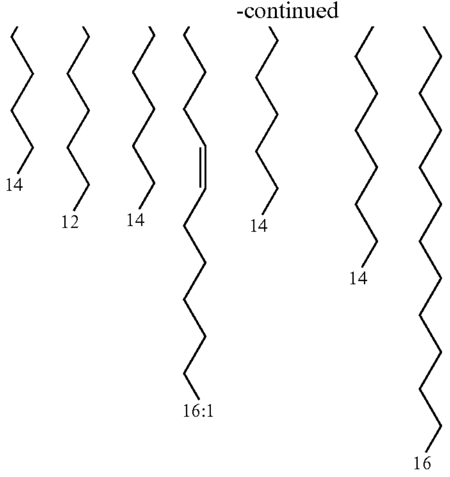
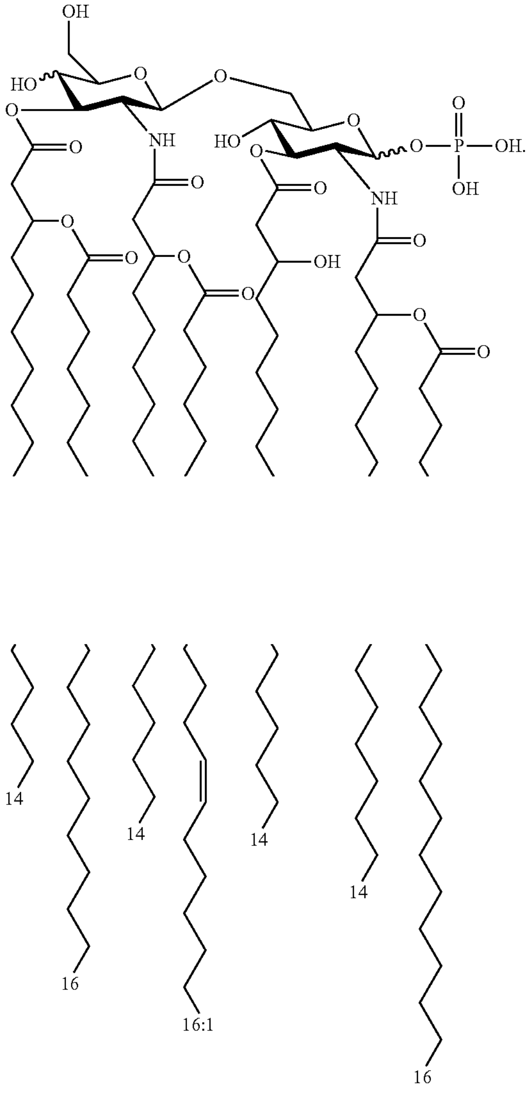
2. The compound of claim 1, wherein the compound has the formula:
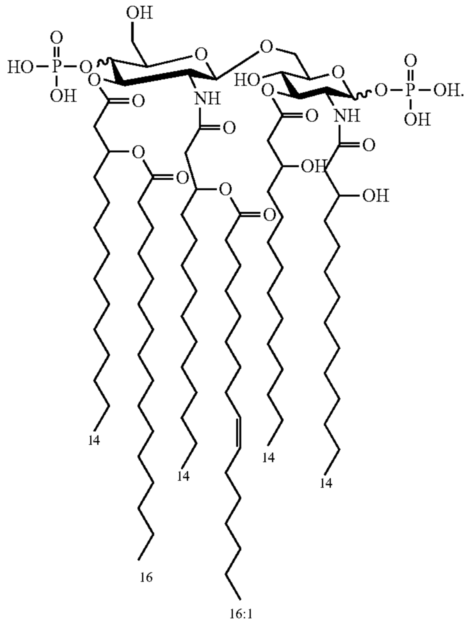
3. The compound of claim 1, wherein the compound has the formula:
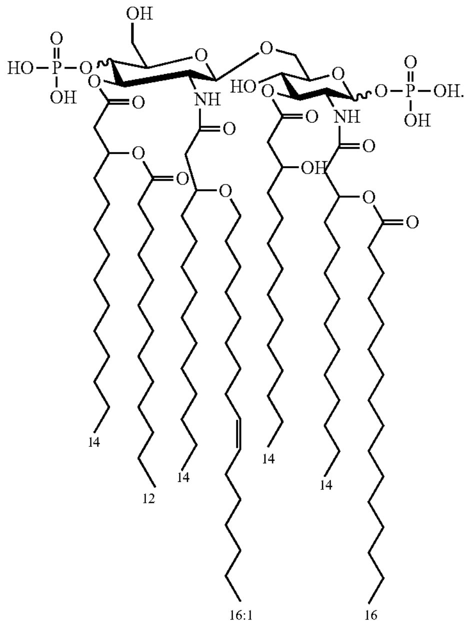

4. The compound of claim 1, wherein the compound has the formula:
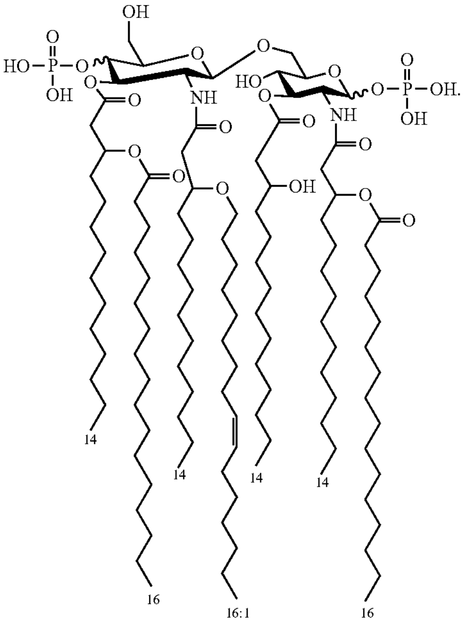
5. The compound of claim 1, wherein the compound has the formula:
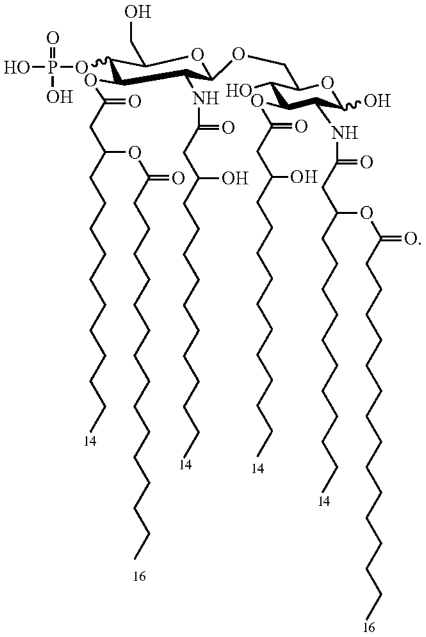
6. The compound of claim 1, wherein the compound has the formula:
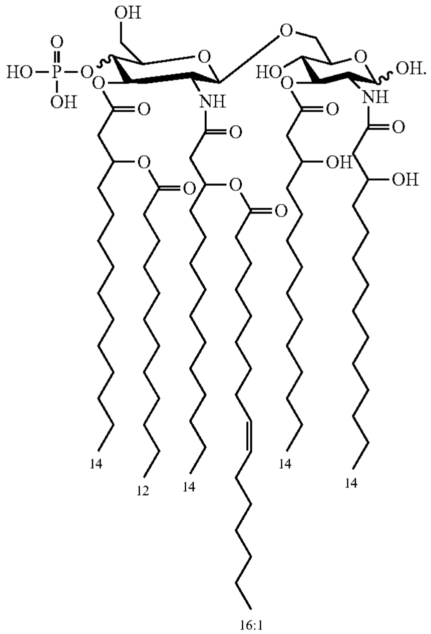
7. The compound of claim 1, wherein the compound has the formula:
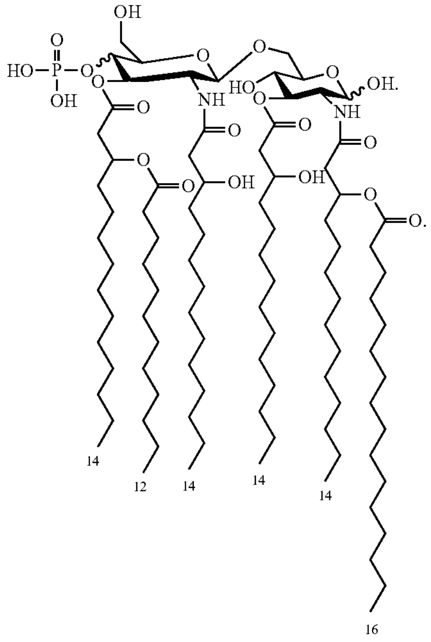

8. The compound of claim 1, wherein the compound has the formula:
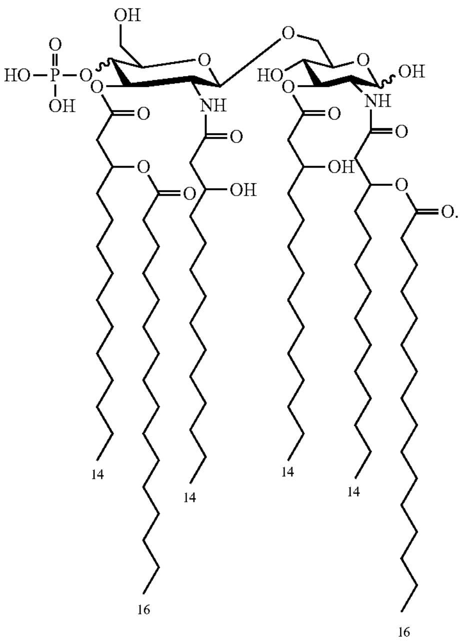
9. The compound of claim 1, wherein the compound has the formula:
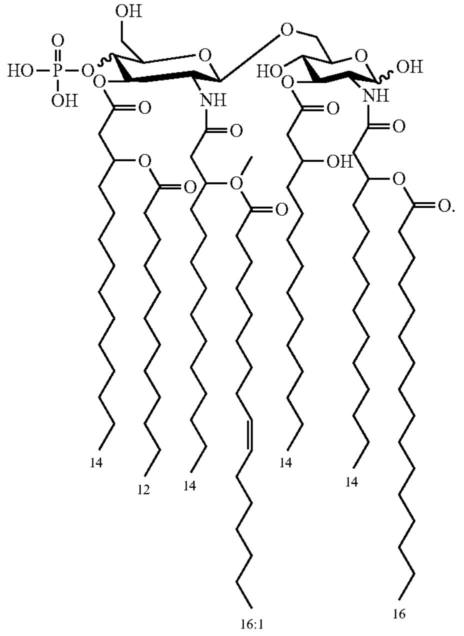
10. The compound of claim 1, wherein the compound has the formula:
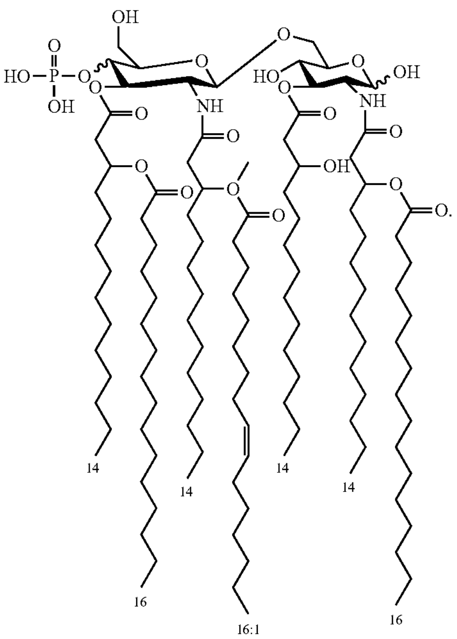
11. The compound of claim 1, wherein the compound has the formula:
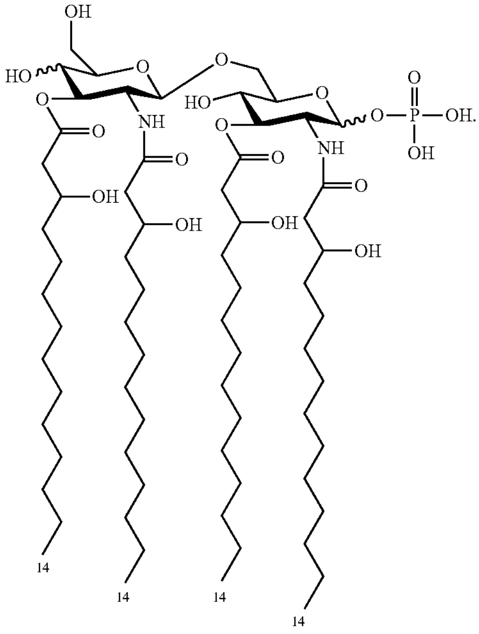

12. The compound of claim 1, wherein the compound has the formula:
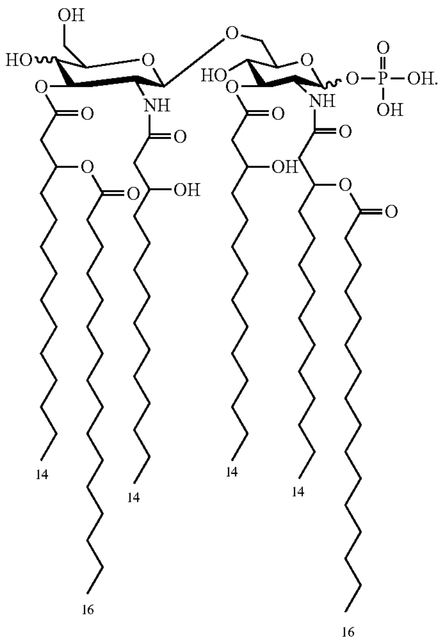
13. The compound of claim 1, wherein the compound has the formula:
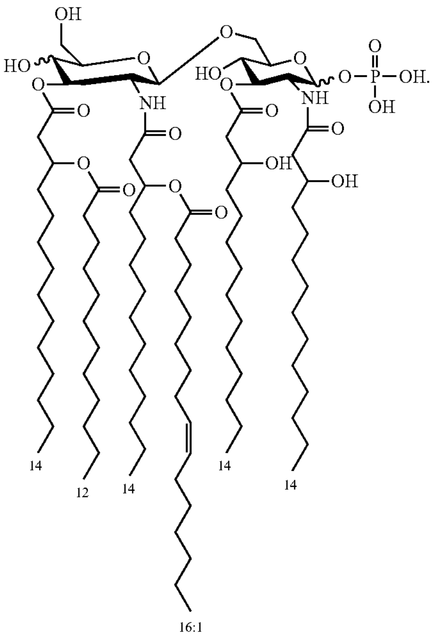
14. The compound of claim 1, wherein the compound has the formula:
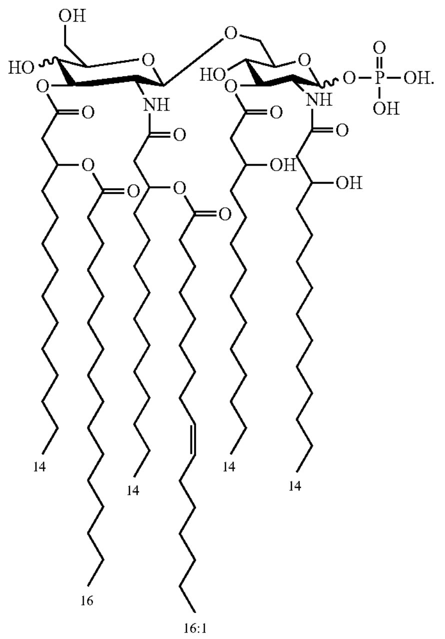
15. The compound of claim 1, wherein the compound has the formula:
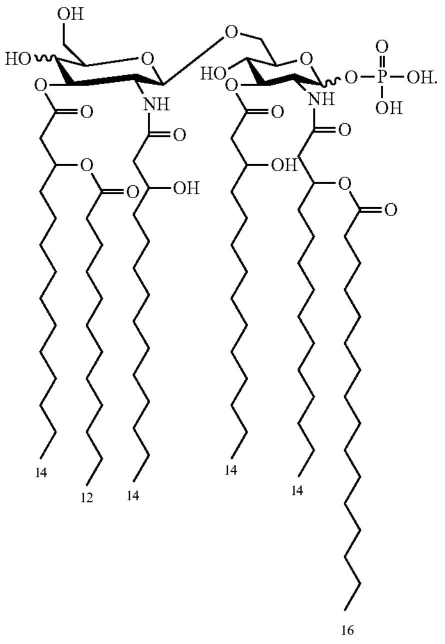

16. The compound of claim 1, wherein the compound has the formula:
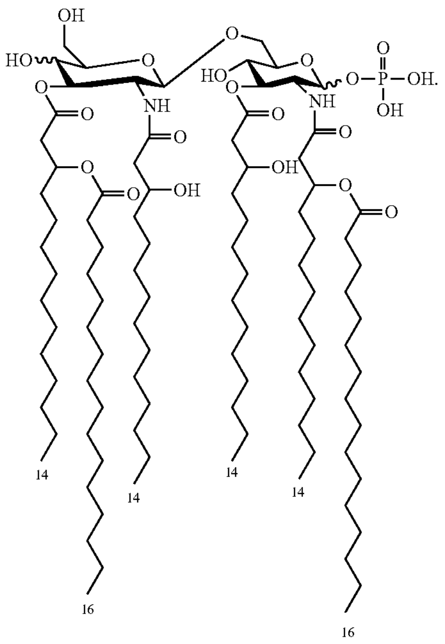
17. The compound of claim 1, wherein the compound has the formula:
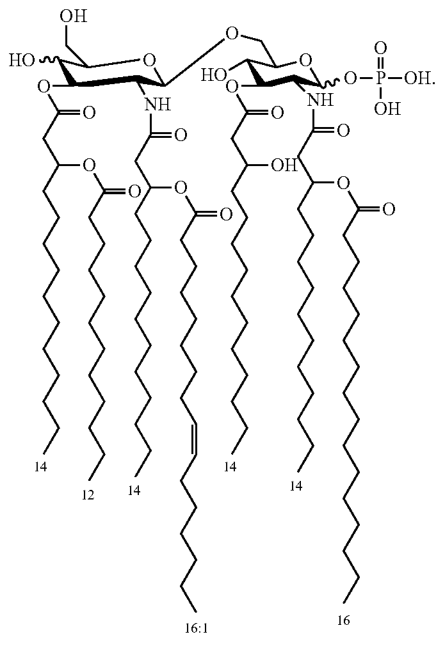
18. The compound of claim 1, wherein the compound has the formula:
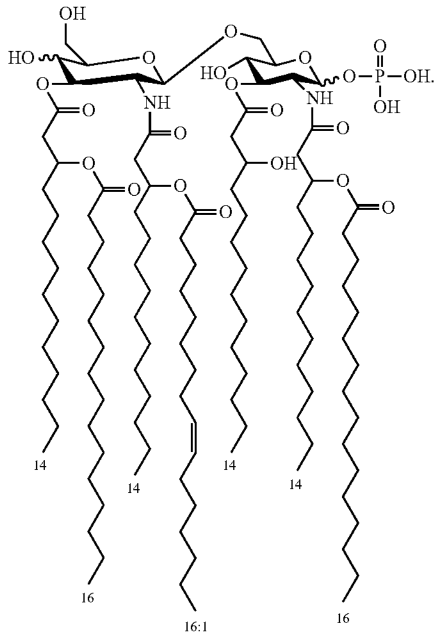
19. The compound of claim 1, wherein the compound has the formula:
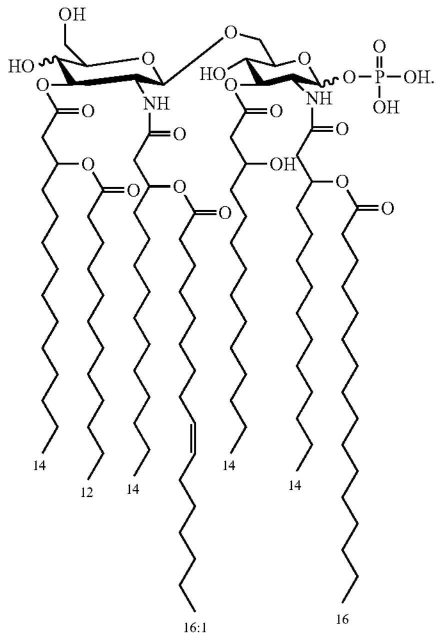
* * * * *